United States Patent [19]
Danishefsky et al.

[11] Patent Number: 6,147,076
[45] Date of Patent: *Nov. 14, 2000

[54] ANALOGUES OF N-ACETYLARDEEMIN, METHOD OF PREPARATION AND USES THEREOF

[75] Inventors: Samuel J. Danishefsky, Englewood, N.J.; Kristopher Depew, New York, N.Y.; Stephen P. Marsden, London, United Kingdom; William Bornmann, New York, N.Y.; Ting Chao Chou, Paramus, N.J.; Andrej Zatorski, New York, N.Y.

[73] Assignees: Sloan-Kettering Institute for Cancer Research; The Trustees of Columbia University in the City of New York, both of New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/749,908

[22] Filed: Nov. 15, 1996

Related U.S. Application Data

[60] Provisional application No. 60/006,750, Nov. 15, 1995.
[51] Int. Cl.$^7$ .................. A61K 31/495; C07D 487/22
[52] U.S. Cl. ............... 514/250; 549/245; 549/338; 549/343
[58] Field of Search ............... 544/245; 514/250

[56] References Cited

U.S. PATENT DOCUMENTS

| | | | |
|---|---|---|---|
| 5,284,947 | 2/1994 | Kadam et al. | 544/245 |
| 5,338,726 | 8/1994 | Shiosaki et al. | 514/17 |
| 5,338,845 | 8/1994 | Barrow et al. | 544/343 |

FOREIGN PATENT DOCUMENTS

WO 93/01718  2/1993  WIPO.

OTHER PUBLICATIONS

Chemical Abstracts, 100:33257, Jan. 30, 1984, Fujisawa Pharmaceutical Co.
Chemical Abstracts, 103:87904, Sep. 16, 1985., Fujisawa Pharmaceutical Co.
Chemical Abstracts, 103:101553, Sep. 3, 1985, Laws et al.
Chemical Abstracts, 108:164470, May 9, 1988, Hodge et al.
Bellamy et al, *Cancer Investigation* 8(5), pp. 547–562 (1990).
Advanced Organic Chemistry (2nd Ed.) by Jerry March, pp. 485–489, 1977.
Takase, S., et al., *J. Antibiot*, 37, 1320 (1984.
Takase, S., et al., *Tetrahedron*, 42, 5887 (1986).
Karwowski, H.P., et al., *J. Antibiot*, 46, 374 (1993).
Hochlowski, J.E., et al., *J. Antibiot*, 46, 380 (1993).
Shinohara, C., et al., *J. Antibiot*, 47, 163 (1994).
Hino, T., et al., *Chem Pharm Bull*, 33, 5202 (1985).
Massden, S.P., et al. *J. Am. Chem. Soc.*, 116, 11143 (1994).
Parsons, R.L., et al., *J. Org. Chem.*, 58 7482 (1993).
Arai et al., *Chem. Pharm. Bull.*, 37:2937–2939, 1989.
Takase et al., *Tetrahedron Letters*, 25:4673–4676, 1984.

*Primary Examiner*—Emily Bernhardt
*Attorney, Agent, or Firm*—Kramer Levin Naftalis & Frankel, LLP

[57] ABSTRACT

The present invention provides a compound having the structure:

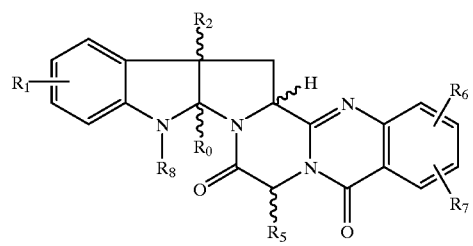

wherein $R_1$ $R_6$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, etc.; wherein $R_0$ and $R_2$ are independently hydrogen, OH, linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, etc.; wherein $R_5$ is hydrogen, $C_1$–$C_9$ linear or branched chain alkyl, phenyl, etc.; and wherein $R_8$ is hydrogen, $C_1$–$C_9$ linear or branched chain acyl, benzoyl, etc.; with the proviso that (a) when $R_2$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$, then $R_2$ is hydrogen; (b) when $R_0$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$, then $R_2$ is OH; and (c) when (i) $R_0$ or $R_2$ is —$CR_3R_3$—CH=$CHR_4$, (ii) $R_3$ and $R_5$ are $CH_3$ and (iii) $R_4$ is hydrogen, then $R_1$, $R_6$ and $R_7$ are not all hydrogen. Also provided are related compounds and compositions, and methods of inhibiting the growth of multidrug resistant cells by means of MDR reversal, collateral sensitivity and quantitative synergism.

38 Claims, 23 Drawing Sheets

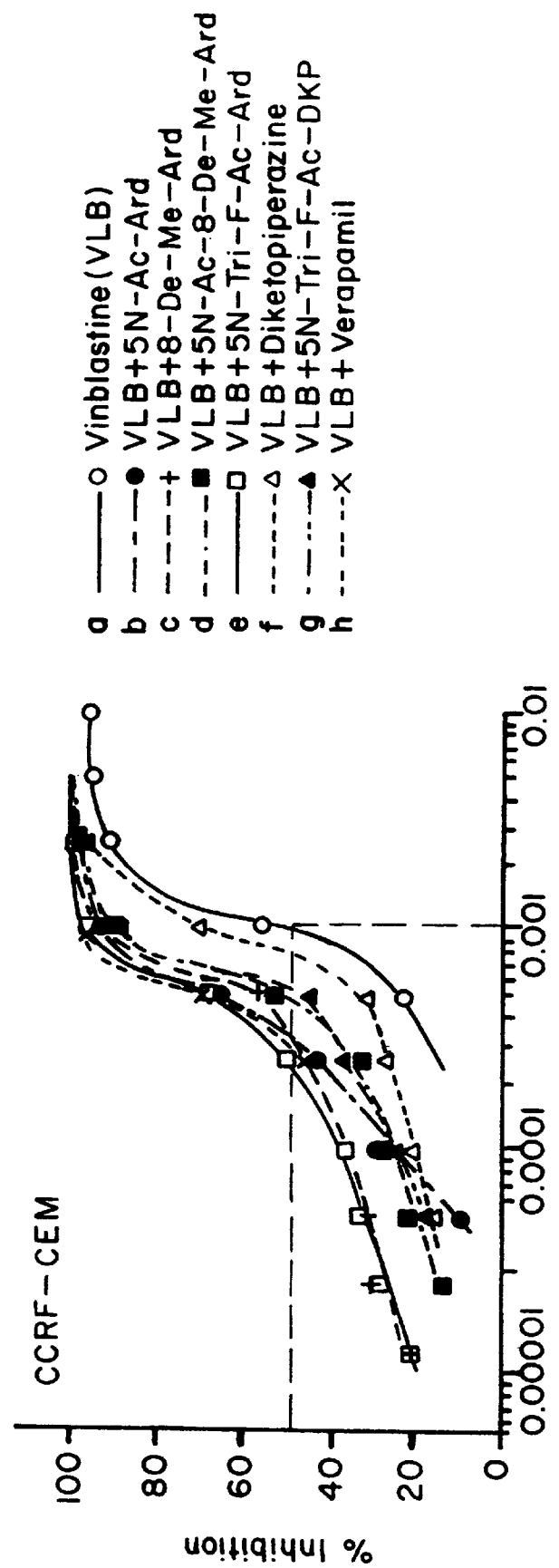

ANALOGUES OF N-ACETYLARDEEMIN, METHOD OF PREPARATION AND USES THEREOF

This application claims the benefit of U.S. Provisional Application Ser. No. 60/006,750 filed Nov. 15, 1995.

This invention was made with government support under grants HL25848, CA28824, CA18856 and HL09187 from the National Institutes of Health. Accordingly, the U.S. Government has certain rights in the invention.

BACKGROUND OF THE INVENTION

Throughout this application, citations for various Publications are provided within parentheses in the text. The disclosures of these publications are hereby incorporated in their entirety by reference into this application in order to more fully describe the state of the art to which this invention pertains.

The development of resistance to cytotoxic agents is a significant problem in cancer therapy. In multiple drug resistance (MDR), cells become cross-resistant to unrelated chemotherapeutic agents. The MDR phenotype is associated with decreased drug retention and over-expression of P-glycoprotein (Pgp), a membrane protein which mediates drug efflux. Pgp expression and chemotherapeutic resistance has also been functionally associated in leukemias and breast cancer, ovarian cancer and neuroblastoma.

Methods of overcoming multidrug resistance have primarily utilized agents which "reverse" the phenotype by increasing intracellular drug concentrations in resistant cells. The reversal agents act presumably by inhibiting P-glycoprotein-mediated drug efflux. However, reversal agents now in clinical trials, such as verapamil and cyclosporin A, have limited utility due to toxic effects. More active agents with fewer toxic effects are needed.

MDR reversal agents include various calcium channel blockers, such as verapamil, calmodulin Inhibitors, steroid hormones and nonionic detergents. The present invention provides compounds which are selectively toxic to drug-resistant cells in the absence of resistant drugs. The present invention demonstrates "synergism" and "collateral sensitivity" of MDR cells toward certain compounds related to ardeemin. Since drug concentrations needed to mediate collateral sensitivity often exceed that for MDR reversal, more efficient methods of preparation are necessary to provide adequate supplies of material. The selective cytotoxicity of these agents to MDR cells may then be exploited clinically.

The present invention provides new compounds and new methods for the treatment of cancer cells, not only through MDR reversal but also through collateral sensitivity and "quantitated synergism." The new compounds include analogues of amauromine (1; Takase, S.; Iwami, M.; Ando, T.; Okamoto, M.; Yoshida, K.; Horiai, H.; Kohsaka, M.; Aoki, H.; Imanaka, H., *J. Antibiot.,* 1984, 37, 1320; Takase, S.; Kawai, Y.; Uchida, I.; Tanaka, H.; Aoki, H., *Tetrahedron,* 1985, 41, 3037; Takase, S.: Itoh, Y.: Uchida, I.; Tanaka, H.; Aoki, H., *Tetrahedron,* 1986, 42, 5887), ardeemin (2; Karwowski, J. P.; Jackson, M.; Rasmussen, R. R.; Humphrey, P. E.; Poddig, J. B.; Kohl, W. L.; Scherr, M. H.; Kadam, S.; McAlpine, J. B., *J. Antibiot.,* 1993, 46, 374; Hochlowski, J. E.; Mullally, M. M.; Spanton, S. G.; Whittern, D. N.; Hill, P.; McAlpine, J. B., *J. Antibiot.,* 1993, 46, 380) and 5-N-acetylardeemin (3). All of these analogues are members of a burgeoning class of biologically active indole alkaloids (including aszonalenin (Kimura, Y.; Hamasaki, T.; Nakajima, H.; Isogai, A., *Tetrahedron Lett.,* 1982, 23, 225) roquefortine (Scott, P. M.; Merrien, M. -A.; Polonsky, J., *Experientia,* 1976, 32, 140; Scott, P. M.; Polonsky, J.; Merrien, M. -A., *J. Agric. Food Chem.,* 1979, 27, 201) and the flustramines (see, for example, Carle, J. S.; Christophersen, C., *J. Am. Chem. Soc.,* 1979, 101, 4012; Carlé, J. S.; Christophersen, C., *J. Org. Chem.,* 1981, 46, 3440) featuring a hexahydropyrrolo[2,3-b]indole nucleus, substituted at the benzylic ring junction with a 1,1-dimethylallyl ("reverse-prenyl") group. In a complementary family of alkaloids (gypsetin), the reverse-prenyl group is found at the 2-position of the indoline. (Shinohara, C.; Hasumi, K.; Takei, Y.; Endo, A., *J. Antibiot.,* 1994, 47, 163; Brevianamide, E.; Birch, A. J.; Wright, J. J., *Tetrahedron,* 1970, 26, 2329.)

Amauromine is a vasodilator, apparently operating through calcium antagonism. (Takase, S.; Iwami, M.; Ando, T.; Okamoto, M.; Yoshida, K.; Horiai, H.; Kohsaka, M.; Aoki, H.; Imanaka, H., *J. Antibiot.,* 1984, 37, 1320) Compound 3 (FIG. 1) is one of the most potent known agents for reversal of multidrug resistance, as measured against KBV-1 (vinblastine resistant) tumor cell lines. (Karwowski, J. P.; Jackson, M.; Rasmussen, R. R.; Humphrey, P. E.; Poddig, J. B.; Kohl, W. L.; Scherr, M. H.; Kadam, S.; McAlpine, J. B., *J. Antibiot.,* 1993, 46, 374; Hochlowski, J. E.; Mullally, M. M.; Spanton, S. G.; Whittern, D. N.; Hill, P.; McAlpine, J. B., *J. Antibiot.,* 1993, 46, 380) A different method of preparing amauromine via a thio-Claisen rearrangement has been disclosed (Takase, S.: Itoh, Y.: Uchida, I.; Tanaka, H.; Aoki, H., *Tetrahedron,* 1986, 42, 5887), but is low-yielding, lacks satisfactory stereocontrol, and is not applicable to preparing 3.

The present invention provides compounds, including analogues and hybrids of ardeemin, amauromine and gypsetin, and compositions thereof, which are useful, alone or in conjunction with anticancer drugs, as MDR reversal, collateral sensitive and quantitated synergistic agents, to treat cancer and prevent the emergence of the MDR phenotype. The invention also provides a method of preparation for N-acylardeemins, previously unavailable except by fermentation, and methods of inhibiting growth of conventional p-glycoprotein MDR and Topo II gene-mutated MDR cells using ardeemin analogues and hybrids.

SUMMARY OF THE INVENTION

The present invention provides a compound having the structure:

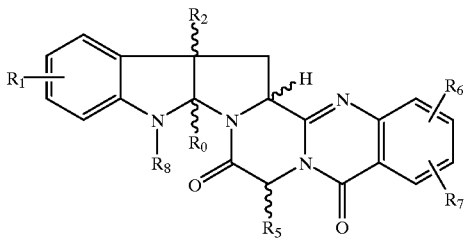

wherein $R_1$, $R_6$ and $R_7$ are independently hydrogen, OH, $NH_2$, SH, halogen, $C_1$-$C_9$ linear or branched chain alkyl, alkylmercapto, alkylamino, dialkylamino, alkoxy, phenyl, alkylphenyl, dialkylphenyl, alkoxyphenyl, hydroxyphenyl, halophenyl, benzyl, or hydroxybenzyl; wherein $R_0$ and $R_2$ are independently hydrogen, OH, $C_1$-$C_9$ linear or branched chain alkyl, $-CR_3R_3-CH(O)CH_2$, $-CR_3R_3-CH_2CH_3$, $-CR_3R_3-CH_2CH_2OH$, $-CR_3R_3-CH(OH)R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; with the proviso that (a) when $R_2$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$, then $R_0$ is hydrogen; (b) when $R_0$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R$—CH=$CHR_4$, then $R_2$ is OH; and (c) when (i) $R_0$ or $R_2$ is —$CR_3R_3$—CH=$CHR_4$, (ii) $R_3$ and $R_5$ are $CH_3$ and (iii) $R_4$ is hydrogen, then $R_1$, $R_6$ and $R_7$ are not all hydrogen.

The present invention also provides a compound having the structure:

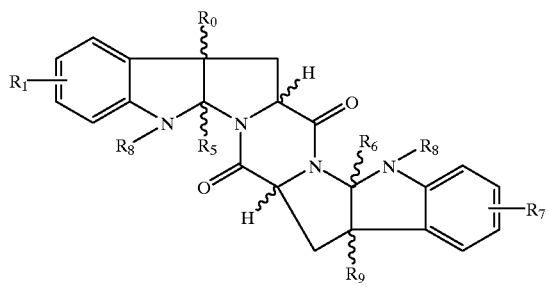

wherein $R_1$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_0$ and $R_5$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_6$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_8$ is $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; and wherein $R_9$ is hydrogen or OH; with the proviso that (a) when $R_0$ is —$CR_3R_3$—CH(O)$CH_2$, —$CR_3R_3$—$CH_2CH$ , —$CR_3R_3$—$CH_2CH_2OH$, —$CR_3R_3$—CH(OH)$R_4$ or —$CR_3R_3$—CH=$CHR_4$, then (i) $R_5$ is H, (ii) $R_6$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$ and (iii) $R_9$ is OH; and (b) when $R_5$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$, then (i) $R_0$ is hydrogen, (ii) $R_6$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=—$CHR_4$ and (iii) $R_9$ is OH; and (d) both $R_1$ and $R_7$ are not hydrogen.

The present invention further provides a compound having the structure:

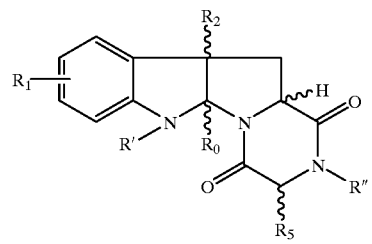

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R^0$ and $R^2$ are independently hydrogen, OH, $C_1$–$C_9$ linear or branched chain alkyl, —$CR_3R_3$—CH(O)$CH_2$, $CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein R' and R" are independently hydrogen, $C_1$–$C_9$ linear or branched chain alkyl, $C_1$–$C_9$ linear or branched chain acyl, benzoyl, alkylbenzoyl, dialkylbenzoyl, alkoxybenzoyl or benzyl; with the proviso that (a) when $R_2$ is —$CR_3R_3$—CH(O)$CH_2$, —$CR_3R_3$—$CH_2CH_3$, —$R_3R_3$—$CH_2CH_2OH$, —$CR_3R_3$—CH(OH)$R_4$ or —$CR_3R_3$—CH=$CHR_4$, then $R_0$ is hydrogen; and (b) when $R_0$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$, then $R_2$ is OH.

The present invention provides a process for synthesizing an N-acylardeemin having the structure:

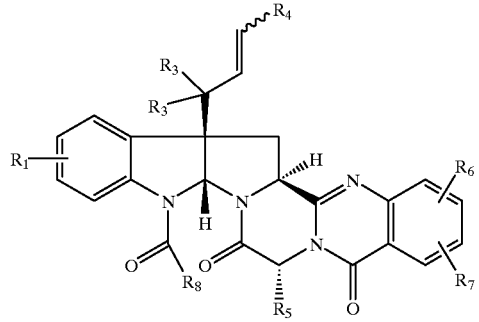

wherein $R_1$, $R_6$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, halophenyl, benzyl, or hydroxybenzyl; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is $C_1$–$C_9$ linear or branched chain alkyl, phenyl, alkylphenyl, dialkylphenyl, alkoxyphenyl or benzyl; which comprises:

(a) (i) reacting a compound having the structure:

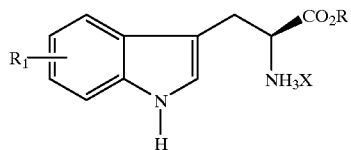

wherein X is Br, Cl, F, I, mesylate, triflate, tosylate, perchlorate, hydrogensulfate, carbonate, bicarbonate or tetrafluoroborate; and R is $C_1$–$C_9$ linear or branched chain alkyl, phenyl, alkylphenyl, dialkylphenyl, alkoxyphenyl, or benzyl, with an acyl halide having the structure $R_0$(C=O)—Z, wherein Z is F, Cl, Br or I, or an acyl anhydride having the structure $[R_0(C=O)]_2O$, wherein $R_0$ is $C_1$–$C_9$ linear or branched chain alkyl, phenyl, alkylphenyl, dialkylphenyl, alkoxyphenyl, benzyl, or 9-fluorenemethyl, to form a dicarbamate having the structure:

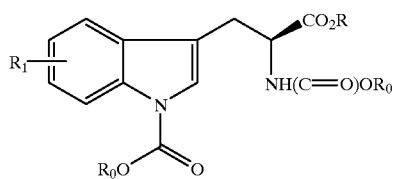

(ii) treating the dicarbamate formed in step (a)(i) with a suitable phenylselenide reagent to form a mixture of phenylselenide dicarbamates having the structures:

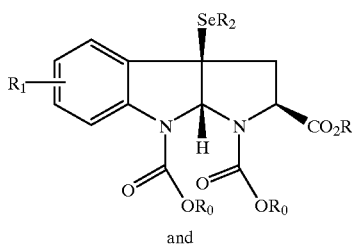

and

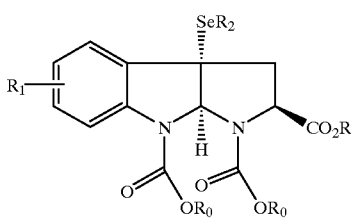

wherein $R_2$ is phenyl, $C_1$–$C_9$ alkylphenyl, dialkylphenyl or trialkylphenyl; and (iii) cross-coupling the mixture of phenylselenide dicarbamates formed in step (a)(ii) with (1) an organostannane having the structure $R_3R_3C$=CHCHR$_4$SnR'R"R'" wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; and wherein R', R" and R'" are independently a $C_1$–$C_9$ linear or branched chain alkyl, phenyl, alkylphenyl, dialkylphenyl, alkoxyphenyl or benzyl, or (2) a Grignard reagent having the structure $Z_0MgR_3R_3C$—CH=CHR$_4$ and an organometallic catalyst having the structure $NiQ_2(PR^{iv}_3)_2$ where Q and $Z_0$ are independently F, Cl, Br or I and $R^{iv}$ is linear or branched chain alkyl, phenyl, alkylphenyl, dialkylphenyl, alkoxyphenyl or benzyl, to form a mixture of cross-coupled dicarbamates respectively having the structure:

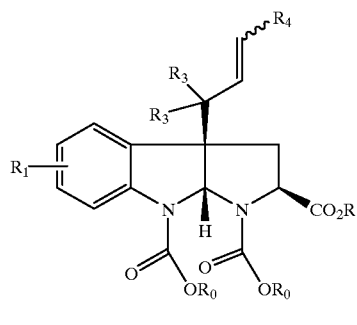

and

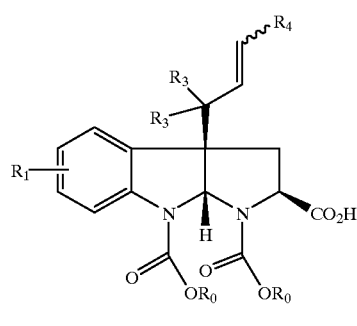

(b) (i) hydrolyzing the mixture of cross-coupled dicarbamates formed in step (a) (iii) to form a mixture of dicarbamate acids;

(ii) purifying the mixture of dicarbamate acids formed in step (b)(i); and (iii) isolating the dicarbamate acid having the structure:

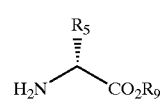

(c) coupling the dicarbamate acid with an amino acid ester having the structure:

$$H_2N-\overset{R_5}{\underset{}{C}}H-CO_2R_9$$

wherein $R_9$ is $C_1$–$C_9$ linear or branched chain alkyl, phenyl, alkylphenyl, dialkylphenyl, alkoxyphenyl, or benzyl; to form a peptide dicarbamate having the structure:

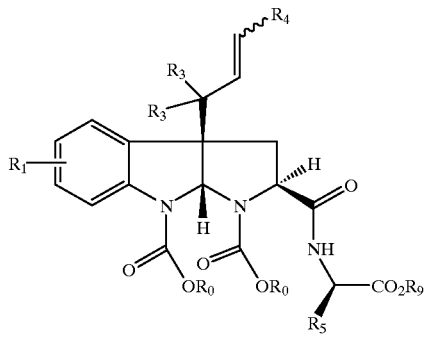

(d) (i) deprotecting and lactamizing the peptide dicarbamate formed in step (c) to form a diketopiperazine having the structure:

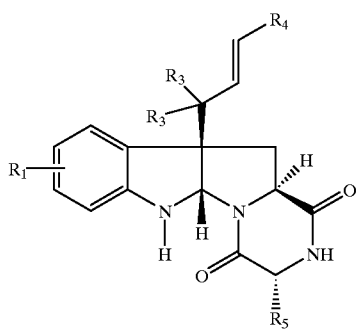

(ii) acylating the diketopiperazine formed in step (d)(i) with a compound having the structure:

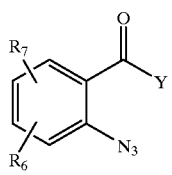

wherein Y is Cl, Br, F or I, to form an N-benzoylated diketopiperazine having the structure:

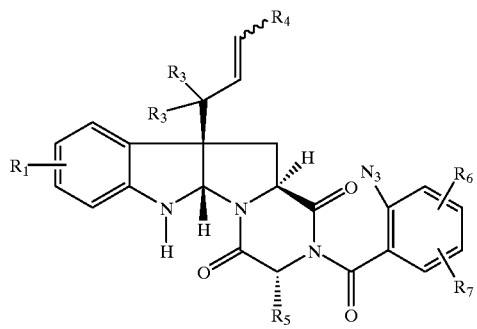

(iii) cyclizing the compound formed in step (d) (ii) to form an ardeemin having the structure:

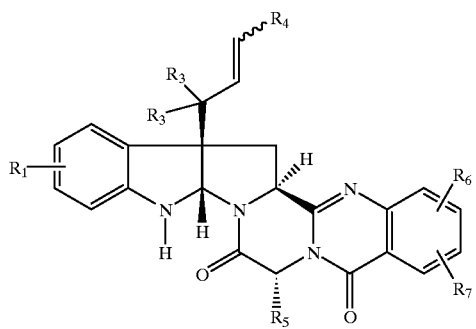

and (iv) acylating the ardeemin formed in step (d) (iii) with (A) an acyl halide having the structure $R_8$ (C=O)—Z' wherein (1) $R_8$ is hydrogen and Z' is OR where R is a linear or branch chain alkyl, phenyl, alkylphenyl, dialkylphenyl, alkoxyphenyl, hydroxyphenyl or benzyl; or (2) wherein $R_8$ is $C_1$–$C_9$ linear or branched chain alkyl, phenyl, alkylphenyl, dialkylphenyl, alkoxyphenyl or benzyl, and Z' is Cl, Br, F, I, or OR where R is a $C_1$–$C_9$ linear or branch chain alkyl, phenyl, alkylphenyl, dialkylphenyl, alkoxyphenyl, hydroxyphenyl or benzyl; or with (B) an acyl anhydride having the structure $[R_8(C=O)]_2O$, wherein $R_8$ is hydrogen, $C_1$–$C_9$ linear or branched chain alkyl, phenyl, alkylphenyl, dialkylphenyl, alkoxyphenyl or benzyl, to form an N-acylardeemin.

The present invention further provides a method of inhibiting the growth of multidrug resistant cells comprising contacting the multidrug resistant cells with an amount of an ardeemin effective to inhibit the growth of multidrug resistant c ells in combination with a pharmaceutically acceptable carrier wherein the ardeemin has the structure:

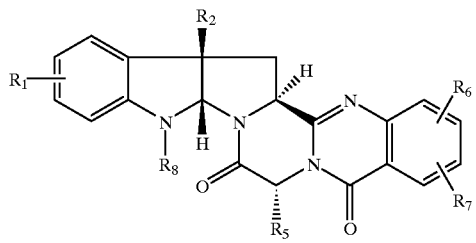

wherein $R_1$, $R_6$ and $R_7$ are independently hydrogen, OH, $NH_2$, SH, halogen, $C_1$–$C_9$ linear or branched chain alkyl, alkylmercapto, alkylamino, dialkylarnino, alkoxy, phenyl, alkylphenyl, dialkylphenyl, alkoxyphenyl, hydroxyphenyl, benzyl, or hydroxybenzyl; wherein $R_2$ is hydrogen, OH, $C_1$–$C_9$ linear or branched chain alkyl, —$CR_3R_3$—OH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=CH$R_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl or $C_1$–$C_9$ linear or branched chain alkyl.

The present invention also provides a method of inhibiting the growth of multidrug resistant cells comprising contacting the multidrug resistant cells with an amount of a compound effective to inhibit the growth of multidrug resistant cells in combination with a pharmaceutically acceptable carrier wherein the compound has the structure:

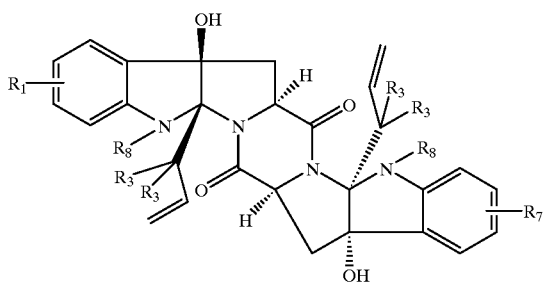

wherein $R_1$ and $R_7$ are independently hydrogen, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_3$ is hydrogen, halogen, $C_1$–$C_9$ linear or branched chain alkyl, phenyl, alkylphenyl, dialkylphenyl, alkoxyphenyl or benzyl; and wherein $R_8$ is hydrogen, $C_1$–$C_9$ linear or branched chain acyl, benzoyl, alkylbenzoyl, dialkylbenzoyl, alkoxybenzoyl, benzyl or $C_1$–$C_9$ linear or branched chain alkyl.

The present invention also provides a method of inhibiting the growth of multidrug resistant cells comprising contacting the multidrug resistant cells with an amount of an amauromine effective to inhibit the growth of multidrug resistant cells in combination with a pharmaceutically acceptable carrier wherein the amauromine has the structure:

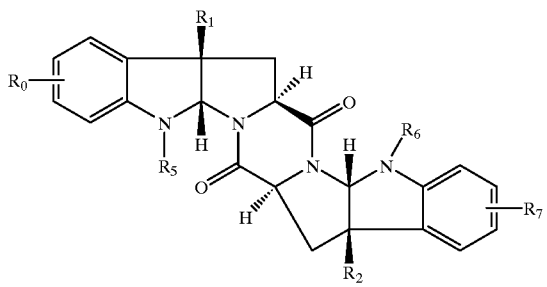

wherein $R_0$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R_1$ and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=CH$R_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; and wherein $R_5$ and $R_6$ are independently hydrogen, $C_1$–$C_9$ linear or branched chain alkyl, acyl, acylalkyl, phenyl, alkylphenyl, dialkylphenyl, alkoxyphenyl, benzyl, benzoyl, alkylbenzoyl and dialkylbenzoyl.

BRIEF DESCRIPTION OF THE FIGURES

FIGS. 19A–19B shows the inhibition of CCRF-CEM and CCRF-CEM/VLB cells treated with combinations of vinblastine and various ardeemin analogues or verapamil.

DETAILED DESCRIPTION OF THE INVENTION

Figure 1:
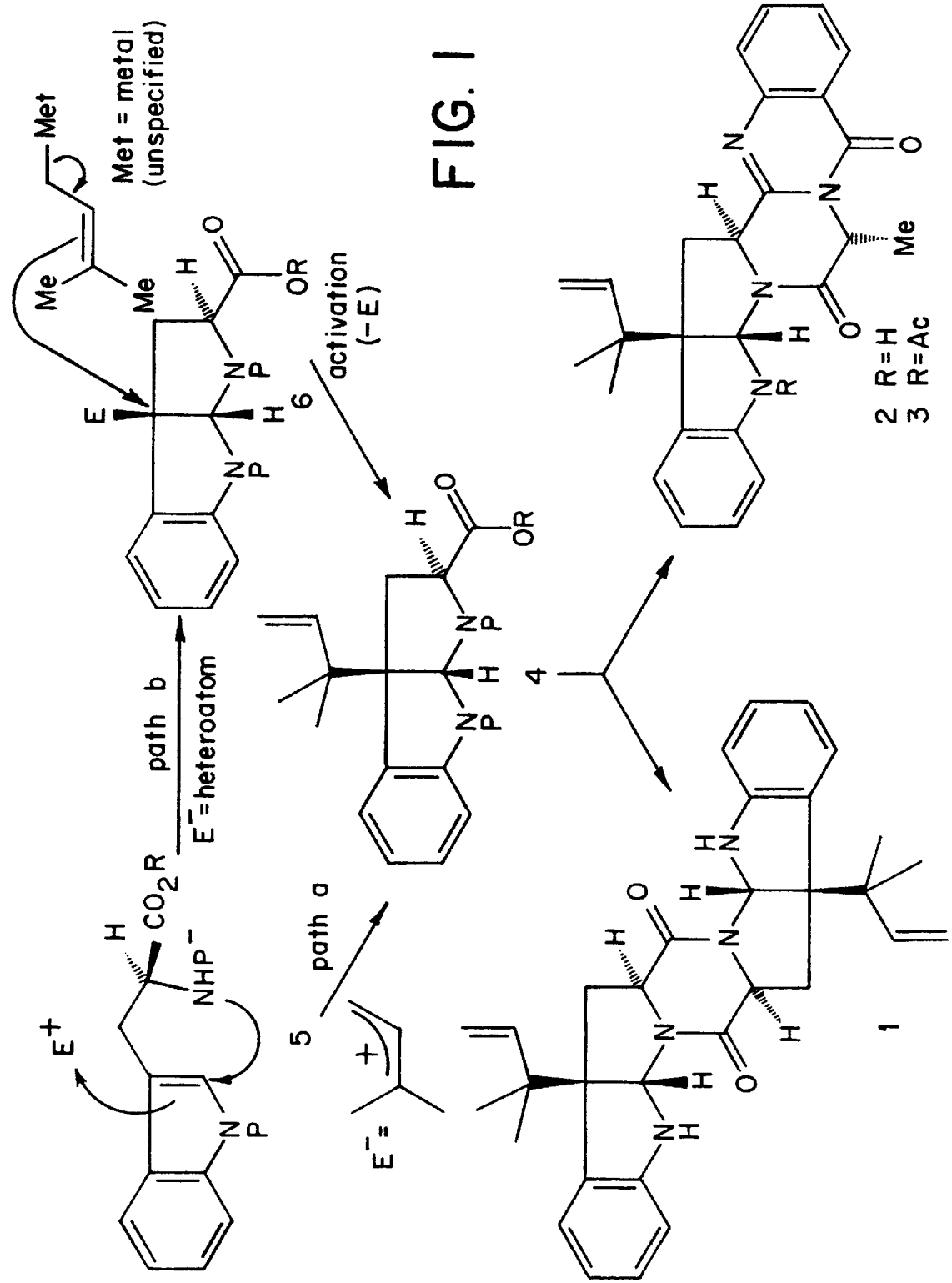
FIG. 1 shows elaboration of tricyclic amino acid 4 to compounds 1, 2 and 3.
Figure 2:
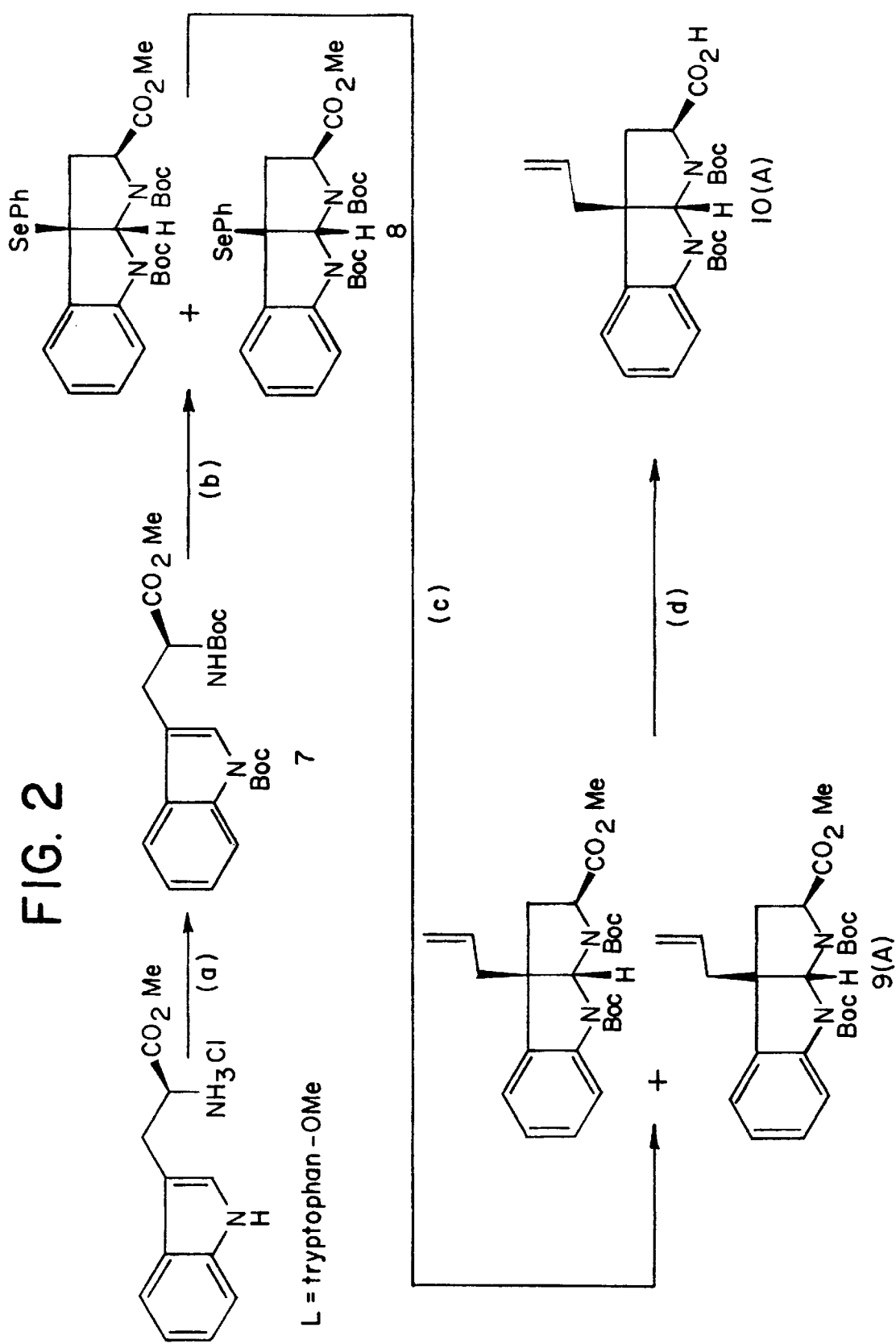
FIG. 2 shows the synthesis of an allyltricyclic intermediate. (a) NaOH, $BOC_2O$, $Bu_4NHSO_4$, $CH_2Cl_2$, 85%; (b) N-PSP, pTSA, $Na_2SO_4$, $CH_2Cl_2$, 78% (5:1, β:α); (c) allyl-$SnBu_3$, $Bu_6Sn_2$, TolH, hv, 95%, 5:1 β:α; (d) 1N NaOH, THF/MeOH, 98%, separate isomers.
Figure 3:
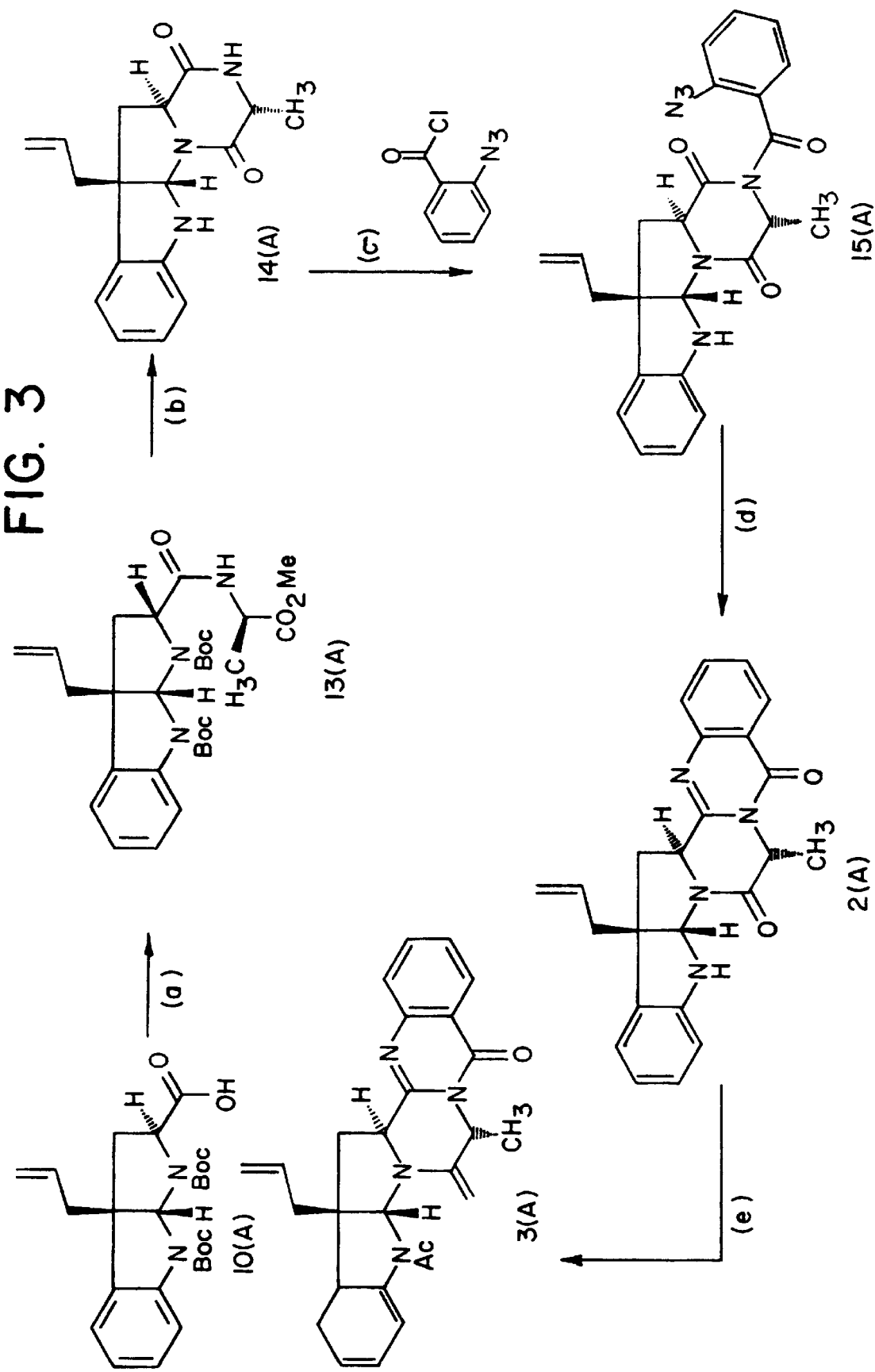
FIG. 3 shows the synthesis of "allyl" N-acetylardeemin. (a) cyanuric fluoride, pyridine, $CH_2Cl_2$, −15° C., D-Ala-OMe.HCl, $NaHCO_3$, $H_2O/CH_2Cl_2$; (b) 1. TMSI, MeCN, 0° C.; 2. $NH_3$, MeOH, DMAP; (c) KHMDS, THF, −78° C.; (d) $PBu_3$, PhH; (e) LDA, THF, −78° C. to RT, AcCl, reflux.

As used herein, the term "linear or branched alkyl group" encompasses, but is not limited to, methyl, ethyl, propyl, isopropyl, t-butyl, sec-butyl, cyclopentyl or cyclohexyl. The alkyl group may contain one carbon atom or as many as fourteen carbon atoms, but preferably contains one carbon atom or as many as nine carbon atoms, and may be substituted by various groups, which include, but are not limited to, acyl, aryl, alkoxy, aryloxy, carboxy, hydroxy, carboxamido or N-acylamino moieties.

As used herein, the terms "alkoxycarbonyl," "acyl," and "alkoxy group" encompass, but are not limited to, a similar range of alkyl groups bonded to the functional group or moiety denoted by each respective term. Examples of alkoxycarbonyl groups include, but are not limited to, methoxycarbonyl, ethoxycarbonyl, propoxycarbonyl, n-butoxycarbonyl, benzyloxycarbonyl, hydroxypropyloxy carbonyl, aminoethoxycarbonyl, sec-butoxycarbonyl, and cyclopentyloxycarbonyl. Examples of acyl groups include, but are not limited to, formyl, acetyl, propionyl, butyryl, and pentanoyl. Examples of alkoxy groups include, but are not limited to, methoxy, ethoxy, propoxy, n-butoxy, sec-butoxy, and cyclopentyloxy.

As used herein, an "aryl group" encompasses, but is not limited to, a phenyl, pyridyl, pyrryl, indolyl, naphthyl, thiophenyl or furyl group, each of which may be substituted by various groups, which include, but are not limited to, acyl, aryl, alkoxy, aryloxy, carboxy, hydroxy, carboxamido or N-acylamino moieties. Examples of aryloxy groups include, but are not limited to, a phenoxy, 2-methylphenoxy, 3-methylphenoxy and 2-naphthyloxy. Examples of acyloxy groups include, but are not limited to, acetoxy, propanoyloxy, butyryloxy, pentanoyloxy and hexanoyloxy.

The present invention provides a compound having the structure:

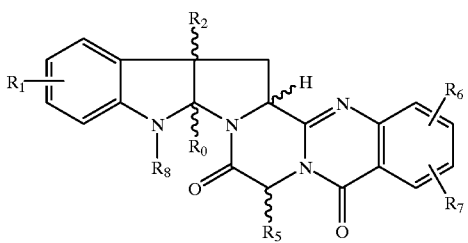

wherein $R_1$, $R_6$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, halophenyl, benzyl, or hydroxybenzyl; wherein $R_0$ and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; with the proviso that (a) when $R_2$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$, then $R_0$ is hydrogen; (b) when $R_0$ is —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$, then $R_2$ is OH; and (c) when (i) $R_0$ or $R_2$ is —$CR_3R_3$—CH=$CHR_4$, (ii) $R_3$ and $R_5$ are $CH_3$ and (iii) $R_4$ is hydrogen, then $R_1$, $R_6$ and $R_7$ are not all hydrogen.

In one embodiment, the present invention provides a compound, wherein $R_0$, $R_1$, $R_3$, $R_4$, $R_6$ and $R_7$ are hydrogen; wherein $R_2$ is —$CR_3R_3$—CH=$CHR_4$; wherein $R_5$ is $CH_3$; and wherein $R_8$ is —(C=O)$CH_3$.

In another embodiment, the present invention provides a compound having the structure:

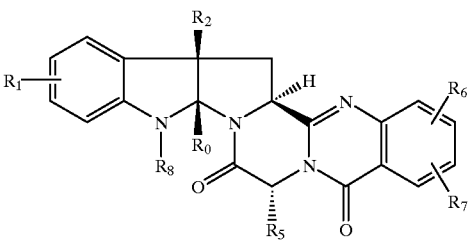

In a certain embodiment, the present invention provides a compound having the structure shown above wherein $R_0$ is hydrogen.

The present invention also provides a composition comprising an amount of a compound having the generic structure shown above effective to inhibit the growth of multidrug resistant cells and a pharmaceutically acceptable carrier.

In one embodiment, the present invention provides the above composition, further comprising a cytotoxic agent. In an additional embodiment, the present invention provides a composition, wherein the cytotoxic agent is an anticancer agent. In another embodiment, the present invention provides the composition, as disclosed above, wherein the anticancer agent is adriamycin. In another embodiment, the present invention provides the composition, as disclosed above, wherein the anticancer agent is vinblastine. In another embodiment, the present invention provides the composition, as disclosed above, wherein the anticancer agent is paclitaxel. In a further embodiment, the present invention provides the composition, as disclosed above, wherein $R_2$ is $—CR_3R_3—CH=CHR_4$; wherein $R_1$, $R_4$, $R_6$ and $R_7$ are hydrogen; wherein $R_3$ and $R_5$ are $CH_3$; and wherein $R_8$ is $—(C=O)CH_3$.

In a certain embodiment, the present invention provides the composition, as disclosed above, wherein the effective amount of the compound is between about 0.01 mg/kg to about 25 mg/kg of body weight. In another embodiment, the present invention provides the composition, as disclosed above, wherein the effective amount is between about 0.1 mg/kg to about 10 mg/kg of body weight.

The present invention provides a compound having the structure:

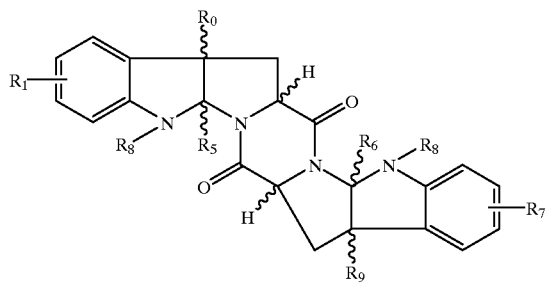

wherein $R_1$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_0$ and $R_5$ are independently hydrogen, OH, $C_1$–$C_9$ linear or branched chain alkyl, $—CR_3R_3—CH(O)CH_2$, $—CR_3R_3—CH_2CH_3$, $—CR_3R_3—CH_2CH_2OH$, $—CR_3R_3—CH(OH)R_4$ or $—CR_3R_3—CH=CHR_4$; wherein $R_6$ is $—CR_3R_3—CH(O)CH_2$, $—CR_3R_3—CH_2CH_3$, $—CR_3R_3—CH_2CH_2OH$, $—CR_3R_3—CH(OH)R_4$ or $—CR_3R_3—CH=CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_8$ is hydrogen, $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; and wherein $R_9$ is hydrogen or OH; with the proviso that (a) when $R_0$ is $—CR_3R_3—CH(O)CH_2$, $—CR_3R_3—CH_2CH_3$, $—CR_3R_3—CH_2CH_2OH$, $—CR_3R_3—CH(OH)R_4$ or $—CR_3R_3—CH=CHR_4$, then (i) $R_5$ is H, (ii) $R_6$ is $—CR_3R_3—CH(O)CH_2$, $—CR_3R_3—CH_2CH_3$, $—CR_3R_3—CH_2CH_2OH$, $—CR_3R_3—CH(OH)R_4$ or $—CR_3R_3—CH=CHR_4$ and (iii) $R_9$ is OH; and (b) when $R_5$ is $—CR_3R_3—CH(O)CH_2$, $—CR_3R_3—CH_2CH_3$, $—CR_3R_3—CH_2CH_2OH$, $—CR_3R_3—CH(OH)R_4$ or $—CR_3R_3—CH=CHR_4$ then (i) $R_0$ is hydrogen, (ii) $R_6$ is $—CR_3R_3—CH(O)CH_2$, $—CR_3R_3—CH_2CH_3$, $—CR_3R_3—CH_2CH_2OH$, $—CR_3R_3—CH(OH)R_4$ or $—CR_3R_3—CH=CHR_4$ and (iii) $R_9$ is OH; and (c) both $R_1$ and $R_7$ are not hydrogen.

In one embodiment, the present invention provides a compound having the structure:

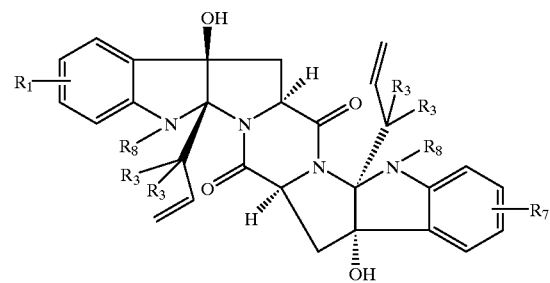

The present invention also provides a composition comprising an amount of the compound having the structure shown above effective to inhibit the growth of multidrug resistant cells and a pharmaceutically acceptable carrier. In one embodiment, the present invention provides the composition, as disclosed above, further comprising an amount of a cytotoxic agent. In another embodiment, the present invention provides the composition, as disclosed above, wherein the cytotoxic agent is an anticancer agent. In another embodiment, the present invention provides the composition, as disclosed above, wherein the anticancer agent is adriamycin. In another embodiment, the present invention provides the composition, as dislosed above, wherein the anticancer agent is vinblastine. In yet another embodiment, the present invention provides the composition, as dislosed above, wherein the anticancer agent is paclitaxel.

In a certain embodiment, the present invention provides the composition, as disclosed above, wherein the effective amount of the compound is between about 0.01 mg/kg to about 25 mg/kg of body weight. In another embodiment, the present invention provides the composition, as disclosed above, wherein the effective amount of the compound is between about 0.1 mg/kg to about 10 mg/kg of body weight.

The present invention also provides a compound having the structure:

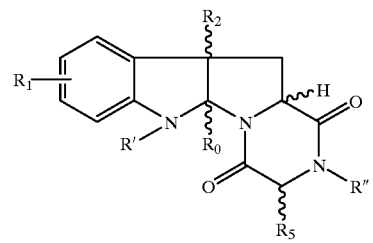

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R^0$ and $R^2$ are independently hydrogen, OH, $C_1$–$C_9$ linear or branched chain alkyl, $—CR_3R_3—CH(O)CH_2$, $—CR_3R_3—CH_2CH_1$, $—CR_3R_3—CH_2CH_2OH$, $—CR_3R_3—CH(OH)R_4$ or $—CR_3R_3—CH=CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein R' and R" are independently hydrogen, $C_1$–$C_9$ linear or branched chain alkyl, $C_1$–$C_9$ linear or branched chain acyl, benzoyl, alkylbenzoyl, dialkylbenzoyl, alkoxybenzoyl or benzyl; with the proviso that (a) when $R_2$ is $-CR_3R_3-CH(O)CH_2$, $-CR_3R_3-CH_2CH_3$, $-CR_3R_3-CH_2CH_2OH$, $-CR_3R_3-CH(OH)R_4$ or $-CR_3R_3-CH=CHR_4$, then $R_0$ is hydrogen; and (b) when $R_0$ is $-CR_3R_3-CH(O)CH_2$, $-CR_3R_3-CH_2CH_3$, $-CR_3R_3-CH_2CH_2OH$, $-CR_3R_3-CH(OH)R_4$ or $-CR_3R_3-CH=CHR_4$, then $R_2$ is OH.

In one embodiment, the present invention provides a compound having the structure:

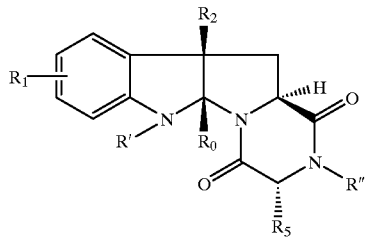

In one embodiment, the present invention provides a composition comprising an amount of the compound having the above structure effective to inhibit the growth of multidrug resistant cells and a pharmaceutically acceptable carrier. In another embodiment, the present invention provides a composition, as above, further comprising an amount of a cytotoxic agent. In an additional embodiment, the present invention provides the composition, as above, wherein the cytotoxic agent is an anti-cancer agent. In a further embodiment, the present invention provides the composition, as above, wherein the anticancer agent is adriamycin. In yet another embodiment, the present invention provides the composition, as above, wherein the anticancer agent is vinblastine. In another embodiment, the present invention provides the composition, as above, wherein the anticancer agent is paclitaxel.

In one embodiment, the present invention provides the composition, as above, wherein the effective amount of the compound is between about 0.01 mg/kg to about 25 mg/kg of body weight. In another embodiment, the present invention provides the composition, as above, wherein the effective amount of the compound is between about 0.1 mg/kg to about 10 mg/kg of body weight.

The present invention also provides a method of inhibiting the growth of multidrug resistant cells comprising contacting the multidrug resistant cells with an amount of the compound having the structure:

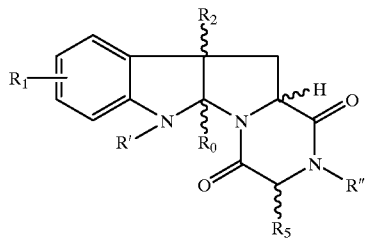

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R^0$ and $R^2$ are independently hydrogen, OH, $C_1$–$C_9$ linear or branched chain alkyl, $-CR_3R_3-CH(O)CH_2$, $-CR_3R_3-CH_2CH_3$, $-CR_3R_3-CH_2CH_2OH$, $-CR_3R_3-CH(OH)R_4$ or $-CR_3R_3-CH=CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein R' and R" are independently hydrogen, $C_1$–$C_9$ linear or branched chain alkyl, $C_1$–$C_9$ linear or branched chain acyl, benzoyl, alkylbenzoyl, dialkylbenzoyl, alkoxybenzoyl or benzyl; with the proviso that (a) when $R_2$ is $-CR_3R_3-CH(O)CH_2$, $-CR_3R_3-CH_2CH_3$, $-CR_3R_3-CH_2CH_2OH$, $-CR_3R_3-CH(OH)R_4$ or $-CR_3R_3-CH=CHR_4$, then $R_0$ is hydrogen; and (b) when $R_0$ is $-CR_3R_3-CH(O)CH_2$, $-CR_3R_3-CH_2CH_3$, $-CR_3R_3-CH_2CH_2OH$, $-CR_3R_3-CH(OH)R_4$ or $-CR_3R_3-CH=CHR_4$, then $R_2$ is OH; effective to inhibit the growth of multidrug resistant cells in combination with a pharmaceutically acceptable carrier.

In one embodiment, the present invention provides a method, as disclosed above, further comprising administering an amount of a cytotoxic agent. In another embodiment, the present invention provides a method, as disclosed above, wherein the cytotoxic agent is an anticancer agent. In yet another embodiment, the present invention provides a method, as disclosed above, wherein the anticancer agent is adriamycin. In another embodiment, the present invention provides a method, as disclosed above, wherein the anticancer agent is vinblastine. In another embodiment, the present invention provides a method, as disclosed above, wherein the anticancer agent is paclitaxel.

In a certain embodiment, the present invention provides the method, as disclosed above, wherein $R_2$ is $-CR_3R_3-CH=CHR_4$; wherein $R_0$, R' and R" are hydrogen; and wherein $R_3$ is $CH_3$. In another embodiment, the present invention provides the method, as disclosed above, wherein the compound has the structure:

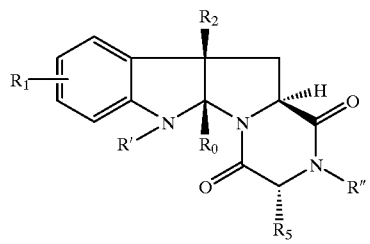

and wherein $R_2$ is $-CR_3R_3-CH=CHR_4$; wherein $R_0$, $R_1$, $R_4$, R' and R" are hydrogen; and wherein $R_3$ and $R_5$ are $CH_3$.

In another embodiment, the present invention further provides the method, as disclosed above, wherein the effective amount of the compound is between about 0.01 mg/kg to about 25 mg/kg of body weight. In another embodiment, the present invention provides the method, as disclosed above, wherein the effective amount of the compound is between about 0.1 mg/kg to about 10 mg/kg of body weight.

The present invention also provides a process for synhnesizing an N-acylardeemin having the structure:

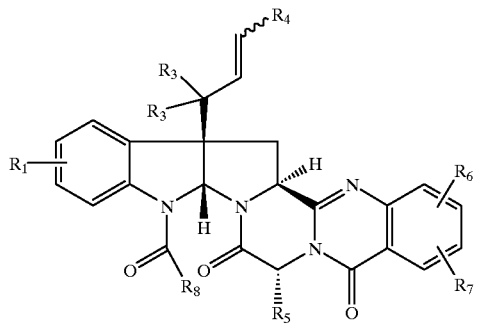

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, halophenyl, benzyl, or hydroxybenzyl; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; wherein $R_6$ and $R_7$ are independently hydrogen, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; and wherein $R_8$ is hydrogen, $C_1$–$C_9$ linear or branched chain alkyl, phenyl, alkylphenyl, dialkylphenyl, alkoxyphenyl or benzyl; which comprises:

(a) (i) reacting a compound having the structure:

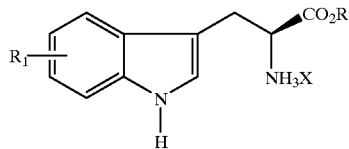

wherein X is Br, Cl, F, I, mesylate, triflate, tosylate, perchlorate, hydrogensulfate, carbonate, bicarbonate or tetrafluoroborate; and R is $C_1$–$C_9$ linear or branched chain alkyl, phenyl, alkylphenyl, dialkylphenyl, alkoxyphenyl, bezyl or alkoxybenzyl, with an acyl halide having the structure $R_0(C=O)$—Z, wherein Z is F, Cl, Br or I, or an acyl anhydride having the structure $[R_0(C=O)]_2O$, wherein $R_0$ is $C_1$–$C_9$ linear or branched chain alkyl, phenyl, alkylphenyl, dialkylphenyl, alkoxyphenyl, benzyl, or 9-fluorenemethyl, to form a dicarbamate having the structure:

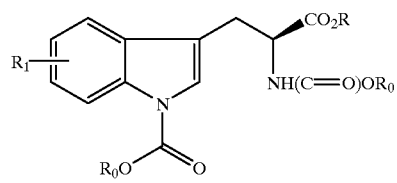

(ii) treating the dicarbamate formed in step (a)(i) with a suitable phenylselenide reagent to form a mixture of phenylselenide dicarbamates having the structures:

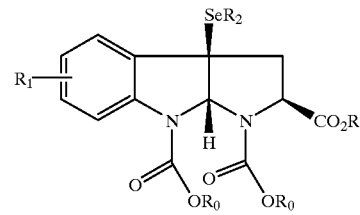

and

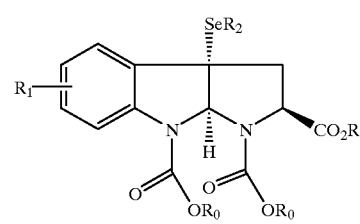

wherein $R_2$ is phenyl, $C_1$–$C_9$ alkylphenyl, dialkylphenyl or trialkylphenyl; and (iii) cross-coupling the mixture of phenylselenide dicarbamates formed in step (a)(ii) with (1) an organostannane having the structure $R_3R_3C=CHCHR_4SnR'R''R'''$ wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; and wherein R', R" and R'" are independently a $C_1$–$C_9$ linear or branched chain alkyl, phenyl, alkylphenyl, dialkylphenyl, alkoxyphenyl or benzyl, or (2) a Grignard reagent having the structure $Z_0MgR_3R_3C—CH=CHR_4$ and an organometallic catalyst having the structure $NiQ_2(PR^{iv}_3)_2$ where Q and $Z_0$ are independently F, Cl, Br or I and $R^{iv}$ is linear or branched chain alkyl, phenyl, alkylphenyl, dialkylphenyl, alkoxyphenyl, furyl, thiophenyl or benzyl, to form a mixture of cross-coupled dicarbamates respectively having The structure:

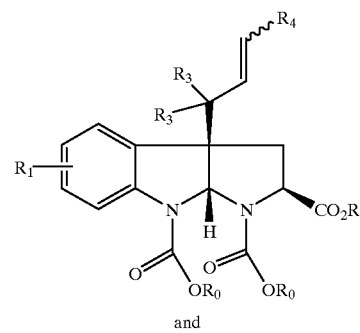

and

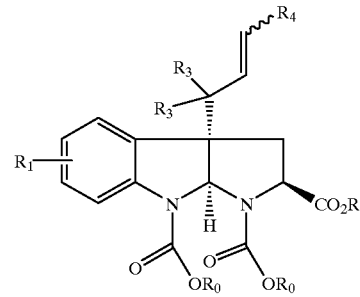

(b) (i) hydrolyzing the mixture of cross-coupled dicarbamates formed in step (a) (iii) to form a mixture of dicarbamate acids;

(ii) purifying the mixture of dicarbamate acids formed in step (b)(i); and (iii) isolating the dicarbamate acid having the structure:

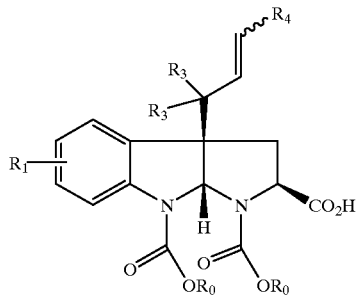

(c) coupling the dicarbamate acid with an amino acid ester having the structure:

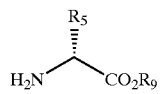

wherein $R_9$ is $C_1$–$C_9$ linear or branched chain alkyl, phenyl, alkylphenyl, dialkylphenyl, alkoxyphenyl, or benzyl; to form a peptide dicarbamate having the structure:

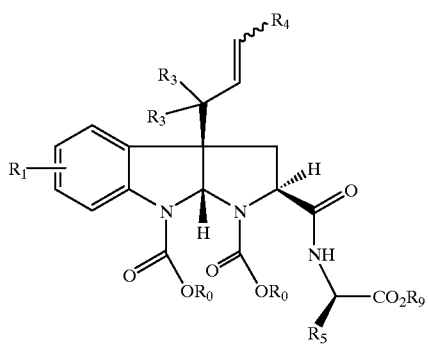

(d) (i) deprotecting and lactamizing the peptide dicarbamate formed in step (c) to form a diketopiperazine having the structure:

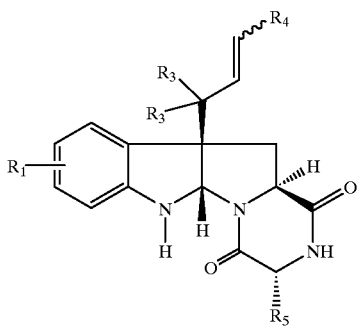

(ii) acylating the diketopiperazine formed in step (d) (i) with a compound having the structure:

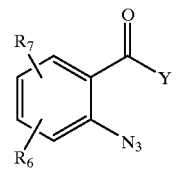

wherein Y is Cl, Br, F or I, to form an N-benzoylated diketopiperazine having the structure:

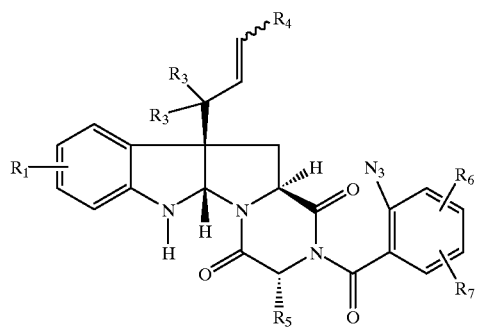

(iii) cyclizing the compound formed in step (d)(ii) to form an ardeemin having the structure:

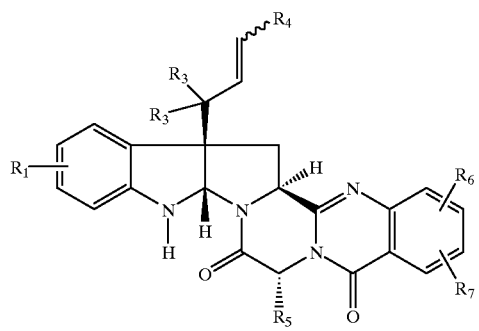

and (iv) acylating the ardeemin formed in step (d) (iii) with (A) an acyl halide having the structure $R_8(C=O)$—Z' wherein (1) $R_8$ is hydrogen and Z' is OR where R is a linear or branch chain alkyl, phenyl, alkylphenyl, dialkylphenyl, alkoxyphenyl, hydroxyphenyl or benzyl; or (2) wherein $R_8$ is $C_1$–$C_9$ linear or branched chain alkyl, phenyl, alkylphenyl, dialkylphenyl, alkoxyphenyl or benzyl, and Z' is Cl, Br, F, I, or OR where R is a $C_1$–$C_9$ linear or branch chain alkyl, phenyl, alkylphenyl, dialkylphenyl, alkoxyphenyl, hydroxyphenyl or benzyl; or with (B) an acyl anhydride having the structure $[R_8(C=O)]_2O$, wherein $R_8$ is hydrogen, $C_1$–$C_9$ linear or branched chain alkyl, phenyl, alkylphenyl, dialkylphenyl, alkoxyphenyl or benzyl, to form an N-acylardeemin.

In one embodiment, the present invention provides the process, as disclosed above, wherein $R_1$, $R_6$ and $R_7$ are hydrogen. In another embodiment, the present invention provides the process, as disclosed above, wherein $R_0$ is t-Bu, R and $R_5$ are $CH_3$, and X, Y and Z are Cl. In a further embodiment, the present invention provides the process, as disclosed above, wherein $R_8$ is $CH_3$. In another embodiment, the present invention provides the process, as disclosed above, wherein R$_3$ is CH$_3$ and R$_4$ is hydrogen. In another embodiment, the present invention provides the process, as disclosed above, wherein R$_2$ is phenyl. In yet another embodiment, the present invention provides the process, as disclosed above, wherein R', R" and R'" are n-Bu.

Step (a)(i) is performed with an acyl halide or an acyl anhydride such as (BOC)$_2$O using a base such as sodium hydroxide under various reaction conditions known in the art to effect the transformation, preferably under phase transfer conditions using water and an immiscible organic solvent such as dichloromethane and a phase transfer catalyst such as tetrabutylammonium hydrogensulfate.

Step (a)(ii) is effected using a suitable selenation reagent such as N-phenylselenophthalimide in the presence of an organic acid, such as p-toluenesulfonic acid, and a dehydrating agent such as sodium sulfate, in an organic solvent such as dichloromethane.

Step (a)(iii) is performed under condition (1) using an organometallic reagent such as prenyl tributylstannane, and an alkyl triflate, such as methyl triflate, in the presence of a non-interacting base, such as 2,6-di-tert-butylpyridine, initially at low temperatures ranging from −100° C. to −50° C., but preferably at −78° C., and later at high temperatures, ranging from ambient temperatures to reflux temperature, but preferably at reflux, in an organic solvent, such as dichloromethane. Alternatively, step (a)(iii) may be carried out under condition (2) using a Grignard reagent with various organometallic catalysts, such as NiCl$_2$(PPh$_3$)$_2$. (Cf. Luh, T. -Y.; Ni, Z. -J., *Synthesis,* 1990, 89; Okamura, H.; Miura, M.; Kosugi, K.; Takei, H., *Tetrahedron,* 1980, 21, 87.) By using a Grignard reagent having the structure ZMgR wherein R is linear or branched alkyl or an aryl, the disclosed process is extended to prepare ardeemins with alkyl or aryl moieties in place of allyl moieties.

Step (b)(i) is effected using any of several satisfactory saponifying agents, including sodium hydroxide or potassium hydroxide, in a mixed aprotic and protic solvent system, such as THF and methanol, at high temperatures, ranging from ambient to reflux, but preferably at reflux.

Steps (b)(ii) and (iii) are accomplished by one or more method of chromatography known to one of skill in the art, such as flash chromatography or high pressure liquid chromatography, on a suitable adsorbant phase, including, but not limited to, spherical or irregular silica gel, reverse-phase silica gel, and aluminum oxide.

Step (c) is effected using a variety of peptide coupling conditions known in the art, for example, using cyanuric fluoride in excess in the presence of an organic base such as pyridine in a non-interacting solvent such as dichloromethane, at a temperature ranging from −45° C. to −5° C., but preferably at −15° C. Subsequent coupling of the preformd fluoride with a suitable amine ester in biphasic conditions, preferably including water containing a base such as sodium bicarbonate and an organic solvent such as dichloromethane. The invention also provides a process, as above, wherein the α-carbon of the amino acid ester has an R or S configuration.

Deprotecting step (d)(i) is performed using a selective electrophilic deprotecting agent such as trimethylsilyl iodide in a polar aprotic solvent such as acetonitrile, followed by lactamizing step (d)(i) involving treatment with a mild base such as ammonia and addition of a cyclization catalyst such as DMAP, or thermolysis.

Step (d)(ii) was effected using a non-nucleophilic base such as KHMDS in excess at low temperature, ranging from −100° C. to −50° C., but preferably at −78° C., in polar aprotic solvent such as THF.

Cyclizing step (d)(iii) proceeds on treatment with a condensing agent such as tributylphosphine in a non-interacting solvent such as benzene, xylenes or toluene, but preferably in benzene.

Step (d)(iv) by treatment with a non-nucleophilic base such as lithium diisopropylamide at low temperature, ranging from −100° C. to −50° C., preferably at −78° C., in a polar aprotic solvent such as THF, or with diisopropylamine from room temperature to reflux temperature. Other useful solvents include such ethereal solvents as dioxane, diethyl ether.

The present invention provides a method of inhibiting the growth of multidrug resistant cells comprising contacting the multidrug resistant cells with an amount of an ardeemin effective to inhibit the growth of multidrug resistant cells in combination with a pharmaceutically acceptable carrier wherein the ardeemin has the structure:

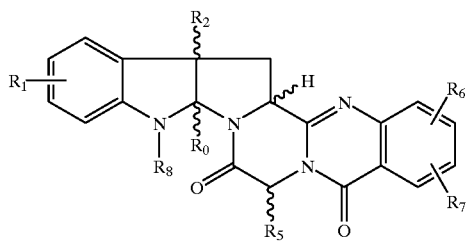

wherein R$_1$, R$_6$ and R$_7$ are independently hydrogen, OH, NH$_2$, SH, halogen, C$_1$–C$_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein R$_0$ and R$_2$ are independently hydrogen, OH, C$_1$–C$_9$ linear or branched chain alkyl, —CR$_3$R$_3$—CH(O)CH$_2$, —CR$_3$R$_3$—CH$_2$CH$_3$, —CR$_3$R$_3$—CH$_2$CH$_2$OH, —CR$_3$R$_3$—CH(OH)R$_4$ or —CR$_3$R$_3$—CH=CHR$_4$; wherein R$_3$ and R$_4$ are independently hydrogen, halogen, C$_1$–C$_9$ linear or branched chain alkyl, phenyl, alkylphenyl, dialkylphenyl, alkoxyphenyl or benzyl; wherein R$_5$ is hydrogen, C$_1$–C$_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein R$_8$ is hydrogen, C$_1$–C$_9$ linear or branched chain alkyl, C$_1$–C$_9$ linear or branched chain acyl, benzoyl, alkylbenzoyl, dialkylbenzoyl, alkoxybenzoyl or benzyl. In one embodiment, the present invention provides the method, as disclosed above, further comprising administering an amount of a cytotoxic agent. In another embodiment, the present invention provides the method, as disclosed above, wherein the cytotoxic agent is an anticancer agent. In another embodiment, the present invention provides the method, as disclosed above, wherein the anticancer agent is adriamycin. In another embodiment, the present invention provides the method, as disclosed above, wherein the anticancer agent is vinblastine. In another embodiment, the present invention provides the method, as disclosed above, wherein the anticancer agent is paclitaxel.

In one embodiment, the present invention provides the method, as disclosed above, wherein the ardeemin has the structure:

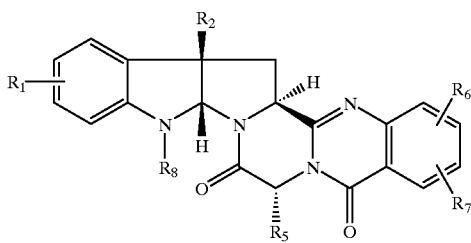

In another embodiment, the present invention provides the method, as disclosed above, wherein the ardeemin is N-acetylardeemin. In a certain embodiment, the present invention provides the method, as described above, wherein $R_2$ is —$CR_3R_3$—CH=$CHR_4$; wherein $R_1$, $R_3$, $R_4$, $R_6$ and $R_7$ are hydrogen; wherein $R_5$ is $CH_3$; and wherein $R_8$ is H.

In another embodiment, the present invention provides the method, as disclosed above, wherein the effective amount of the compound is between about 0.01 mg/kg to about 25 mg/kg of body weight. In another embodiment, the present invention provides the method, as disclosed above, wherein the effective amount of the compound is between about 0.1 mg/kg to about 10 mg/kg of body weight.

The present invention further provides a method of inhibiting the growth of multidrug resistant cells comprising contacting the multidrug resistant cells with an amount of a compound effective to inhibit the growth of multidrug resistant cells in combination with a pharmaceutically acceptable carrier wherein the compound has the structure:

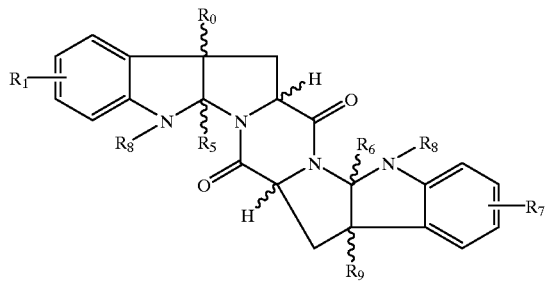

wherein $R_1$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_0$ and $R_5$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_6$ is hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_8$ is hydrogen, $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; and wherein $R_9$ is hydrogen or OH.

In one embodiment, the present invention provides the method, as disclosed above, wherein $R_1$, $R_7$ and $R_8$ are hydrogen; and wherein $R_3$ is $CH_3$.

In one embodiment, the present invention provides the method, as disclosed above, wherein the compound has the structure:

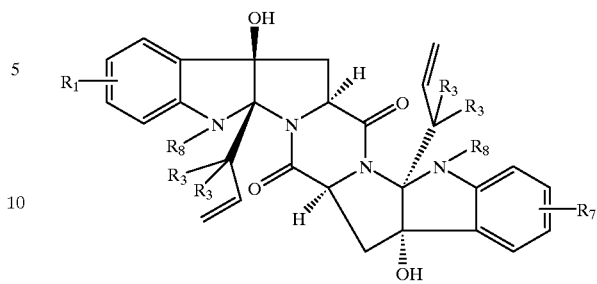

In another embodiment, the present invention provides the method, as disclosed above, further comprising administering a cytotoxic agent. In another embodiment, the present invention provides the method, as disclosed above, wherein the cytotoxic agent is an anticancer agent. In a certain embodiment, the present invention provides the method, as disclosed above, wherein the anticancer agent is adriamycin. In another embodiment, the present invention provides the method, as disclosed above, wherein the anticancer agent is vinblastine. In yet another embodiment, the present invention provides the method, as disclosed above, wherein the anticancer agent is paclitaxel.

In one embodiment, the present invention provides the method, as disclosed above, wherein $R_1$, $R_7$ and $R_8$ are hydrogen; and wherein $R_3$ is $CH_3$.

In a certain embodiment, the present invention provides the me,hod, as disclosed above, wherein the effective amount of the compound is between about 0.01 mg/kg to about 25 mg/kg of body weight. In another embodiment, the present invention provides the method, as disclosed above, wherein the effective amount of the compound is between about 0.1 mg/kg to about 10 mg/kg of body weight.

The present invention also provides a method of inhibiting the growth of multidrug resistant cells comprising contacting the multidrug resistant cells with an amount of an amauromine effective to inhibit the growth of multidrug resistant cells in combination with a pharmaceutically acceptable carrier wherein the amauromine has the structure:

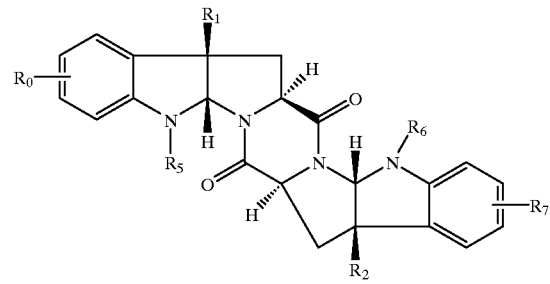

wherein $R_0$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R_1$ and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; and wherein $R_5$ and $R_6$ are independently hydrogen, $C_1$–$C_9$ linear or branched chain alkyl, acyl, acylalkyl, phenyl, alkylphenyl, dialkylphenyl, alkoxyphenyl, benzyl, benzoyl, alkylbenzoyl or dialkylbenzoyl.

In one embodiment, the present invention provides the method, as disclosed above, further comprising administering a cytotoxic agent. In another embodiment, the present invention provides the method, as disclosed above, wherein the cytotoxic agent is an anticancer agent. In a certain embodiment, the present invention provides the method, as disclosed above, wherein the anticancer agent is adriamycin. In another embodiment, the present invention provides the method, as disclosed above, wherein the anticancer agent is vinblastine In yet another embodiment, the present invention provides the method, as disclosed above, wherein the anticancer agent is paclitaxel.

In a certain embodiment, the present invention provides the method, as disclosed above, wherein $R_0$, $R_5$, $R_6$ and $R_7$ are hydrogen. In another embodiment, the present invention provides the method, as disclosed above, wherein $R_1$ and $R_2$ are —$CR_3R_3$—CH=$CHR_4$; wherein $R_3$ is $CH_3$; and wherein $R_4$ is hydrogen.

In one embodiment, the present invention provides the method, as disclosed above, wherein the effective amount of the compound is between about 0.01 mg/kg to about 25 mg/kg of body weight. In another embodiment, the present invention provides the method, as disclosed above, wherein the effective amount of the compound is between about 0.1 mg/kg to about 10 mg/kg of body weight.

As used herein, the term "pharmaceutically acceptable carrier" means any of the standard pharmaceutical carriers. Suitable carriers are well known in the art and may include, but are not limited to, any of the standard pharmaceutical carriers.

The compositions provided herein may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectible medium. Carriers are intended to include necessary and inert binders, suspending agents, lubricants, flavorants, sweeteners, preservatives, dyes, and coatings.

Optimal dosages to be administered may be determined by those skilled in the art, and will vary with the particular ardeemin, gypsetin or amauromine analogue in use, the strength of the preparation, the mode of administration, and the advancement of the disease condition. Additional factors depending on the particular patient being treated will result in a need to adjust dosages, including patient age, weight, gender, diet, and time of administration.

Experimental Details

General Procedures

All air- and moisture-sensitive reactions were performed in a flame-dried apparatus under an argon atmosphere unless otherwise noted. Air-sensitive liquids and solutions were transferred via syringe or canula. Wherever possible, reactions were monitored by thin-layer chromatography (TLC). Gross solvent removal was performed in vacuum under aspirator vacuum on a Buchi rotary evaporator, and trace solvent was removed on a high vacuum pump at 0.1–0.5 mmHg.

Melting points (mp) were uncorrected and performed in soft glass capillary tubes using an Electrothermal series IA9100 digital melting point apparatus.

Infrared spectra (IR) were recorded using a Perkin-Elmer 1600 series Fourier-Transform instrument. Samples were prepared as neat films on NaCl plates unless otherwise noted. Absorption bands are reported in wavenumbers ($cm^{-1}$). Only relevant, assignable bands are reported.

Proton nuclear magnetic resonance ($^1$H NMR) spectra were determined using a Varian 200, 300 or 400 MHz spectrometer, as indicated below. Chemical shifts are reported in parts per million (ppm) downfield from tetramethylsilane (TMS; $\delta$=0 ppm) using residual $CHCl_3$ as a lock reference ($\delta$=7.25 ppm). Multiplicities are abbreviated in the usual fashion: s=singlet; d=doublet; t=triplet; q=quartet; m=multiplet; br=broad.

Carbon nuclear magnetic resonance ($^{13}$C NMR) spectra were performed on a Varian 300 spectrometer at 75 MHz with composite pulse decoupling. Samples were prepared as with $^1$H NMR spectra, and chemical shifts are reported relative to TMS (0 ppm); residual $CHCl_3$ was used as an internal reference ($\delta$=77.0 ppm).

All high resolution mass spectral (HRMS) analyses were determined by Fast Atom Bombardment techniques or electron impact ionization (EI) on a JEOL JMS-DX 303HF mass spectrometer with perfluorokerosene (PFK) as an internal standard. Low resolution mass spectra (MS) were determined by either electron impact ionization (EI) or chemical ionization (CI) using the indicated carrier gas (ammonia or methane) on a Delsi-Nermag R-10-10 mass spectrometer. For gas chromatography/mass spectra (GCMS), a DB-5 fused capillary column (30 m, 0.25mm thickness) was used with helium as the carrier gas. Typical conditions used a temperature program from 60–250° C. at 40° C./min.

Thin layer chromatography (TLC) was performed using precoated glass plates (silica gel 60, 0.25 mm thickness). Visualization was done by illumination with a 254 nm UV lamp, or by immersion in anisaldehyde stain (9.2 mL p-anisaldehyde in 3.5 mL acetic acid, 12.5 mL conc. sulfuric acid and 338 mL 95% ethanol (EtOH)) and heating to colorization.

Flash silica gel chromatography was carried out according to the standard protocol.

Unless otherwise noted, all solvents and reagents were commercial grade and were used as received, except as indicated hereinbelow, where solvents were distilled under argon using the drying methods listed in paretheses: $CH_2Cl_2$ ($CaH_2$); benzene ($CaH_2$); THF (Na/ketyl); $Et_2O$ (Na/ketyl); diisopropylamine ($CaH_2$).

| Abbreviations | |
|---|---|
| Ac | acetate, acetyl |
| Bn | benzyl |
| BOC or Boc | t-butyloxycarbonyl |
| $CH_2Cl_2$ | dichloromethane |
| DMF | N,N-dimethylformamide |
| DMAP | 4-dimethylaminopyridine |
| DDQ | 2,3-dichloro-5,6-dicyano-1,4-benzoquinone |
| EtOAc | ethyl acetate |
| hex | hexane |
| LiHMDS | lithium hexamethyldisilazide |
| KHMDS | potassium hexamethyldisilazide |
| MDR | multiple drug resistance |
| MeCN | acetonitrile |
| OTf | triflate |
| PSP | phenylselenophthalimide |
| r.b. | round bottom flask |
| r.t. | room temperature |
| THF | tetrahydrofuran |
| TLC | thin layer chromatography |

-continued

| Definitions | |
|---|---|
| CI | combination index; CI < 1, =1, and >1 indicates synergism, additivity and antagonsims respectively, as defined by the combination index equation |
| collateral sensitive agent: | compound acting alone that kills or inhibits the growth of drug-resistant cancer cells even more than regular wild-type cancer cells |
| DRI | dose-reduction index; signifies how much the dose of each drug in a synergistic combination may be reduced at a given effect level compared with the dose of each drug alone (toxicity toward one host may be avoided or reduced when the dose is reduced) |
| $D_m$ | median-effect dose or concentration such as $ED_{50}$ or $IC_{50}$ |
| $F_a$ | fraction affected |
| m | slope of the median-effect plot, signifying the shape of the dose-effect curve |
| r | linear correlation coefficient |
| synergism | drug combinations that yield a combination index smaller than one, and yield an isobologram that shows combination data point(s) on the lower left of the graph |

EXAMPLE 1

Bis(tert-butyloxycarbonyl)-L-tryptophan (7): Powdered sodium hydroxide (80 mg, 2.0 mmol) was added to a solution of tryptophan methyl ester hydrochloride (100 mg, 0.39 mmol) and tetrabutylammonium hydrogen sulfate (14 mg, 0.04 mmol) in $CH_2Cl_2$ (4 mL), and the mixture was stirred for two hours at room temperature. Bis(t-butyloxy) carbonic anhydride (257 mg, 1.18 mmol) was then added and the mixture was stirred for 15 hours more, and then filtered through a pad of celite and evaporated in vacuo. The residue was purified by flash chromatography (30% EtOAc:hexane) to afford the title compound (150 mg, 91% yield) as a white waxy solid: $R_f$=0.60 (silica gel, 30% EtOAc in hexane): $[\alpha]^{20}_D$=+47.9° (c 1.0, $CHCl_3$); $^1H$ NMR (200 MHz, $CDCl_3$) δ8.08 (d, J=6.2 Hz, 1H, H-7), 7.46 (d, J=7.6 Hz, 1H, H-4), 7.37 (s, 1H, H-2), 7.30 (t, J=6.9 Hz, 1H, H-6), 7.21 (t, J=6.9 Hz, 1H, H=5), 5.10 (d, J=8.0 Hz, 1H, NH), 4.63 (dd, J=12.3, 5.5 Hz, 1H, H-2'), 3.67 (s, 3H, OMe), 3.24 (dd, J=14.55, 5.3 Hz, 1H, H-1'), 3.15 (dd, J=14.2 Hz, 5.3H, 1H, H-1'), 1.64 (s, 9H, t-butyl) ppm; $^{13}C$ NMR 75 MHz, $CDCl_3$) δ171.6, 154.2, 148.8, 134.7, 130.0, 123.8, 123.4, 121.8, 118.1, 114.5, 82.9, 79.1, 76.5, 53.0, 51.6, 27.5 ppm; IR (film) 3388, 2977, 1731, 1502, 1453, 1369, 1255, 1159, 1086 cm$^{-1}$; MS (CI) calc'd for $C_{22}H_{30}N_2O_6$; M/e 418.2104, found 418.2121; 436 ($M^+$ $NH_4$), 419 (M+H), 418 (M), 363, 236; Analysis calc'd for $C_{22}H_{30}N_2O_6$: C, 63.14; H, 7.23; N, 6.59; found: C, 63.45; H, 7.57; N, 6.54.

EXAMPLE 2

Selenide ester (8): To a stirring suspension of 7 (7.33 9, 17.5 mmol), N-phenylselenophthalimide (7.94 g, 26.3 mmol), and sodium sulfate (24.9 g, 175 mmol) in $CH_2Cl_2$ (35 mL, 0.5 M) was added p-toluenesulfonic acid (333 mg, 1.75 mmol). The milieu was stirred for 6–8 hours, filtered through a Celite pad over cotton, and the filtered solids rinsed with $CH_2Cl_2$. The filtrate was washed with 1 N NaOH (3 times), and the combined aqueous layers back-extracted with $CH_2Cl_2$. The combined organic layers were dried over $Na_2SO_4$, filtered, concentrated and chromatographed (silica gel, 10% ethyl acetate in hexane) to yield 7.48 g (74%) of an off-white solid as a 9:1 ratio of diastereomers. $R_f$=0.64 (silica gel, 306 EtOAc in hexane); $[\alpha]^{20}_D$=−41.4° (c 1.0, $CHCl_3$); $^1H$ NMR (400 MHz, $CDCl_3$) δ7.41–7.09 (m, 8H), 7.01 (t, J=7.95 Hz, 1H), 6.25 (s, 1H, H-1), 3.88 (dd, J=9.8, 6.6 Hz, 1H, H-2), 3.63 (s, 3H, OMe), 2.88 (dd, J=12.4, 6.7 Hz, 1H, H-3), 2.36 (dd, J=12.5, 10.0 Hz, 1H, H-3), 1.54 (s, 9H, t-butyl), 1.42 (s, 9H, t-butyl) ppm; $^{13}C$ NMR (75 MHz, $CHCl_3$) δ172.3, 152.1, 142.0, 137.5, 132.8, 129.3, 129.2, 128.9, 124.1, 123.9, 123.5, 123.4, 123.0, 117.7, 117.6, 83.0, 82.7, 81.6, 80.9, 59.1, 52.1, 38.6, 28.3, 28.2 ppm; IR (film) 2981, 1758, 1748, 1712, 1393, 1366, 1159 cm$^{-1}$; MS (CI) calc'd for $C_{28}H_{34}N_2O_6Se$ (Se80): m/e 575.1663, found 575.1669; 573 (M), 434 (M−SePh+$NH_4$); Analysis calc'd for $C_{28}H_{34}N_2O_6Se$: C, 58.64;

H, 5.97; N, 44.88; found: C, 58.80; H, 6.22; N, 4.58.

EXAMPLE 3

Prenyl Ester (9): To a −78° C. solution of 8 (1.51 g, 2.63 mmol) and 2,6-di-tert-butylpyridine (2.65 mL, 11.8 mmol) in $CH_2Cl_2$ (26 mL 0.1 M) was added methyl trifuoromethane-sulfonate (1.34 mL, 11.8 mmol) and then prenyl tributylstannane (3.86 mL, 11.8 mmol) under argon. The solution was allowed to warm to room temperature over 6 hours then was attached to a condenser and refluxed for 14 hours. The solution was cooled, quenched with an equal volume of sat. $NaHCO_3$ and the organic layer was separated. The aqueous layer was extracted with $CH_2Cl_2$ (2 times). The combined organic layers were washed with brine, dried over $Na_2SO_4$, filtered, concentrated and chromatographed (silica gel, 10–40% EtOAc in hexane) to give 770 mg (60%) of a white foam as a 9:1 mixture of diastereomers: $R_f$=0.63 (silica gel, 30% EtOAc in hexane); $[\alpha]^{20}_D$=−68.8° (c 1.0, $CHCl_3$); $^1H$ NMR (400 MHz, $CDCl_3$) δ7.23 (d, J=8.1 Hz, 1H), 7.18 (t, J=7.5 Hz, 1H), 7.14 (d, J=6.8 Hz, 1H), 7.02 (t, J=7.6 Hz, 1H), 6.13 (s, 1H, H-1), 5.84 (dd, J=17.4, 10.8 Hz, 1H), 5.05 (d, J=10.8 Hz, 1H), 4.98 (d, J=17.4 Hz, 1H), 3.78 (dd, J=10.2, 8.6 Hz, 1H, H-2), 3.69 (s, 3H, OMe), 2.36 (dd, J=12.3, 6.6 Hz, 1H, H-3), 2.25 (dd, J=12.4, 10.2 Hz, 1H, H-3), 1.54 (s, 9H, t-butyl), 1.43 (s, 9H, t-butyl), 1.00 (s, 3H, $CH_3$), 0.92 (s, 3H, $CH_3$) ppm; $^{13}C$ NMR (75 MHz, $CDCl_3$) δ172.8, 152.1, 143.2, 142.9, 133.5, 128.4, 125.3, 124.5, 123.0, 118.0, 114.1, 81.2, 81.0, 78.6, 61.3, 59.3, 51.9, 40.2, 34.8, 28.6, 28.2, 22.9, 22.1 ppm; IR (film) 2977, 2800, 1750, 1704, 1599, 1481, 1462, 1390, 1367, 1253, 1167, 1061, 1012, 918 cm$^{-1}$; MS (CI) calc'd for $C_{27}H_{38}N_2O_6$: m/e 486.2730, found 486.2744; 487 (MH), 431, 401, 387.

EXAMPLE 4

Prenyl acid (10): A solution of 9 (146 mg, 0.30 mmol) was heated under reflux in THF (2.5 mL), methanol (2.5 mL), 1N NaOH (1.5 mL) and water (1 mL) for 12 hours, then the mixture was allowed to cool to room temperature. The solution was carefully acidified to pH 4 with 5% citric acid solution. The solution was extracted with ethyl acetate (4×10 mL), the combined organic layers were washed with brine, dried over $Na_2SO_4$, filtered, concentrated and chromatographed (silica gel, 35:60:5 ethyl acetate:hexane:acetic acid) to yield 142 mg (98%) of a white solid as a 9:1 mixture of diastereomers. Repeated chromatography allows the separation of the diastereomers.: $[\alpha]^{20}_D$=−57.5° (c 1.0, $CHCl_3$); $^1H$ NMR (400 MHz, $CDCl_3$) δ7.37 (d, J=7.7 Hz, 1H), 7.25 (d, J=6.9 Hz, 1H), 7.14 (t, J=6.9 Hz, 1H), 7.04 (t, J=7.4 Hz, 1H), 6.14 (s, !H, H-1), 5.84 (dd, J=17.2, 10.7 Hz, 1H), 5.07

(d, J=10.6 Hz, 1H), 5.00 (d, J=17.2 Hz, 1H), 3.78 (dd, J=9.9, 6.9 Hz, 1H, H-2), 2.37 (m, 2H, 2×H-3), 1.53 (s, 9H, t-butyl), 1.40 (s, 9H, t-butyl), 1.01 (s, 3H, $CH_3$) 0.92 (s, 3H, $CH_3$) ppm; $^{13}C$ NMR (75 MHz, $CDCl_3$) δ178.4, 152.1, 143.1, 142.8, 133.3, 128.5, 128.2, 124.6, 123.2, 118.1, 114.3, 81.4, 81.2, 78.6, 61.7, 59.2, 40.3, 34.7, 28.3, 28.2, 22.9, 22.1 ppm; IR (film) 3500–2800, 2980, 1713, 1479, 1395, 1366, 1252, 1152, 1020 $cm^{-1}$; MS (CI) calc'd for $C_{26}H_{36}N_2O_6$: m/e 472.2573, found 472.2562; 473, 373.

EXAMPLE 5

Peptide (13): Acyl fluoride: To a −15 °C. solution of 10 (1.63 g, 3.45 mmol) and pyridine (0.275 mL, 3.45 mmol) in $CH_2Cl_2$ (30 mL) in a plastic test tube was added cyanuric fluoride (1.24 mL, 13.8 mmol) dropwise over a 2–3 min period. After one hour at −15° C., the solution was quenched with ice, and extracted with $CH_2Cl_2$ (3×25 mL). The combined extracts were dried over $Na_2SO_4$, filtered, and concentrated to give an off-white foam (1.53 g, 93%).

EXAMPLE 6

Peptide: The above acyl fluoride (1.53 g, 3.22 mmol) in $CH_2Cl_2$ (16 mL) was added via canula to a solution of D-Ala-OMe.HCl (450 mg, 3.22 mmol), $NaHCO_3$ (541 mg, 6.44 mmol), and water (16 mL). This biphasic solution was stirred vigorously for 45 min, then water was added, and the solution was extracted with $CH_2Cl_2$ (3×20 mL). The combined organic layers were washed with brine, dried over $Na_2SO_4$, filtered, concentrated, and chromatographed to yield 1.37 g (71% from 10) of a white foam: $R_f$=0.50 (silica gel, 50% EtOAc in hexane); $[\alpha]^{20}_D$=−73.3° (c=1.7, $CHCl_3$); $^1H$ NMR (400 MHz, $CDCl_3$) δ7.40 (br s, 1H, H-4) 7.24 (t, J=8.0 Hz, 1H), 7.17 (d, J=7.2 Hz, 1H), 7.0 (t, J=7.6 Hz, 1H), 6.23 (d, J=7.2 Hz, 1H, Ala-NH), 6.15 (s, 1H, H-5), 5.87 (dd, J=17.6, 10.8 Hz, 1H, H-19), 5.08 (d, J=10.8 Hz, 1H, H-20-cis), 5.01 (d, J=17.6 Hz, 1H, H-20-trans), 4.60 (q, J=7.2 Hz, 7.2H, H-8), 3.74 (s, 3H, OMe), 3.69 (dd, J=10.4, 6.8 Hz, 1H, H-15b), 2.43 (dd, J=12.8, 10.4 Hz, 1H, H-16), 2.32 (dd, J=12.8, 10.4 Hz, 1H, H-16) 1.55 (s, 9H, t-Bu), 1.39 (br s, 9H, t-Bu), 1.38 (d, J=7.2 Hz, 3H, H-17), 1.04 (s, 3H, Me), 0.95 (s, 3H, Me) ppm; $^{13}C$ NMR (300 MHz, $CDCl_3$) δ173.2, 171.7, 152.3, 143.2, 142.8, 133.6, 128.5, 124.8, 123.2, 118.0, 114.3, 114.2, 81.5, 81.0, 79.2, 61.5, 61.1, 52.3, 47.7, 40.3, 35.5, 28.4, 28.2, 22.9, 22.2, 18.4 ppm; IR (film, NaCl) 3412, 3327, 3080, 2979, 1710, 1602, 1532, 1478, 1455, 1370, 1161, 1022, 922, 736, $cm^{-1}$; MS calc'd for $C_{30}H_{43}N_3O_7$: m/e 557.3101, found 557.3093.

EXAMPLE 7

Diketopiperazine (14): Peptide 13 (1.464 g, 2.63 mmol) was azeotroped twice with benzene, dissolved in freshly distilled dry MeCN (26 mL), chilled to 0° C. under argon, and treated with TMSI (1.12 mL, 7.89 mmol) dropwise over a 2 min period. After 40 min, the reaction was dumped into sat. $NaHCO_3$ and extracted with $CH_2Cl_2$ (3×25 mL) The combined organic layers were washed with brine, dried over $Na_2SO_4$, filtered, concentrated and chromatographed (60–100% EtOAc in hexane) to give a white foam (810 mg, 86%); $R_f$=0.35 (silica gel, 100% EtOAc). To the above foam in a 0° C. solution of MeOH saturated with ammonia (11.3 mL) was added DMAP (111 mg, 0.91 mmol). The solution was stirred overnight with gradual warming to room temperature, concentrated, and chromatographed (silica gel, 60–100% EtOAc in hexane) to give a white foam (633 mg, 86%) in 74% overall yield from 13. $R_f$=0.30 (silica gel, 100% EtOAc); $[\alpha]^{20}_D$=−311° (c 0.09, $CHCl_3$) $^1H$ NMR (400 MHz, $CDCl_3$) δ7.16 (d, J=7.5 Hz, 1H), 7.11 (app t, J=7.5, 7.2 Hz, 1H), 6.76 (app t, J=8.1, 7.5 Hz, 1H), 6.60 (d, J=8.1 Hz, 1H), 5.95–6.60 (br s, 1H, variable, Ala-NH), 5.97 (dd, J=17.4, 10.8 Hz, 1H, H-19), 5.56 (s, 1H), 5.12 (d, 9.8 Hz, 1H, H-20-cis), 5.08 (d, 17.6 Hz, 1H, H-20-trans), 4.90–5.15 (br s, 1H, 5-NH), 4.00 (dq, J=7.2, 3.6 Hz, 1H, H-8), 3.92 (d, J=11.1, 6.3 Hz, 1H, H-15b), 2.54 (dd, J=12.6, 6.3 Hz, 1H, H-16), 2.42 (dd, J=12.6, 11.1 Hz, 1H, H-16), 1.39 (d, J=7.2 Hz, 3H, Ala-Me), 1.12 (s, 3H, Me), 1.00 (s, 3H, Me) ppm; $^{13}C$ NMR (300 MHz, $CDCl_3$) δ169.1, 166.7, 150.0, 143.5, 128.9, 128.8, 125.1, 118.8, 114.6, 109.1, 77.7, 61.3, 57.7, 53.3, 40.9, 36.8, 22.9, 22.4, 20.6 ppm; IR (film, NaCl) 3322, 3083, 2979, 2876, 1665, 1607, 1452, 1368, 1316, 1216, 1134, 1084, 922, 749, 666 $cm^{-1}$; MS calc'd for $C_3H_{23}N_3O_2$: m/e 325.1790, found 325.1808.

EXAMPLE 8

Benzoylated diketopiperazine (15): o-Azidobenzoyl chloride: To a 0° C. $CH_2Cl_2$ solution (16 mL) of o-azidobenzoic acid (1.26 g, 7.75 mmol) and oxalyl chloride (1.35 mL, 15.5 mmol) was added one drop of DMF. The solution was allowed to warm to room temperature for 1 hour, concentrated via a stream of argon and then in vacuo, redissolved in THF (7.75 mL, 1.0 M), and chilled to −78° C.

Separately, a −78° C. THF solution of 14 (315 mg, 0.968 mmol) under argon was treated with KHMDS (2.52 mL, 0.5M in toluene, 1.26 mmol) dropwise over a 2 min period. The resultant green solution was stirred at −78° C. for 30 min. Then 2.9 mL of the acid chloride solution prepared above was added via canula over a 3–5 min period. After 20 min, more KHMDS (0.97 mL, 0.48 mmol) was added at −78° C., and after 5 min more acid chloride (1.0 mL, 0.97 mmol) was added. The solution was allowed to warm to room temperature, quenched with sat. $NaHCO_3$, and extracted with EtOAc (3 times). The combined organic layers were washed with brine, dried over $Na_2SO_4$, filtered, concentrated, and chromatographed (silica gel, 10–50% EtOAc in hexane) to give 15 as a white foam (364 mg, 80%) then 100% EtOAc to recover unreacted 14 (10–15%). $R_f$=0.55 (silica gel, 50% EtOAc in hexane; $[\alpha]^{20}_D$=−143° (c 0.01, $CHCl_3$); $^1H$ NMR (300 MHz, $CDCl_3$) δ7.49 (ddd, J=7.8, 6.2, 1.5 Hz, 1H), 7.40 (dd, J=7.8, 1.5 Hz, 1H), 7.23 (t, J=7.6, 7.5 Hz, 1H), 7.15 (m, 3H), 6.78 (dd, J=7.5, 7.3 Hz, 1H), 6.63 (d, J=7.5 Hz, 1H), 5.98 (dd, J=17.3, 10.8 Hz, 1H), 5.62 (s, 1H, N—CH—N), 5.15 (d, J=11.1 Hz, 1H), 5.11 (d, J=17.3 Hz, 1H), 5.08 (s,1H, NH), 5.07 (q, J=7.2 Hz, 1H, Ala-CH), 4.05 (dd, J=9.8, 7.6 Hz, 1H, Trp-CH), 2.53 (m, 2H, Trp-$CH_2$), 1.50 (d, J=7.2 Hz, 3H, Ala-OCH), 1.12 (s, 3H), 1.00 (s, 2H) ppm; $^{13}C$ NMR (300 MHz, $CDCl_3$) δ169.0. 167.8, 166.6, 149.8, 143.2, 136.3, 131.8, 129.1, 128.5, 128.4, 125.2, 125.0, 118.9, 118.1, 114.8, 109.3, 77.5, 61.6, 59.1, 55.5, 40.9, 36.8, 22.8, 22.3, 17.7 ppm; IR (film, NaCl) 3356, 2973, 2129, 1722, 1674, 1598, 1580, 1485, 1467, 1448, 1383, 1301, 1219, 1150, 752 $cm^{-1}$; MS calc'd for $C_{26}H_{26}N_6O_3$: m/e 470.2066, found 470.2073.

EXAMPLE 9

Ardeemin (2): Tributylphosphine (0.171 mL, 0.69 mmol) was added to a solution of 15 (293 mg, 0.623 mol) in dry benzene (6.2 mL). The orange solution was stirred for 4 hours under argon, concentrated, triturated with 30% EtOAc in hexane to remove tributylphosphine oxide, and then chromatographed (silica gel, 10–50% EtOAc in hexane to recover ardeemin (191 mg, 72%) and then 100% EtOAc to recover 30 mg of 14) $R_f$=0.45 (silica gel, 50% EtOAc in hexane).

EXAMPLE 10

5-N-Acetylardeemin (3): 0.5 M LDA preparation: To a solution of disopropylamine (0.147 mL, 1.05 mmol) in THF (1.45 mL) at −78° C. was added BuLi (0.40 mL, 2.5M in hex; 1.00 mmol) under argon. After 3 min, the solution was warmed towards room temperature for 15 min and then recooled to −78° C.

EXAMPLE 11

5-N-Acetylardeemin:

Method A. A solution of ardeemin (68.0 mg, 0.159 mmol) in THF (1.6 mL) at −78° C. was treated with 0.5 M LDA (0.320 mL, 0.16 mmol). The green solution was warmed towards room temperature for 5 min, recooled to −78° C., and treated with acetyl chloride (0.028 mL, 0.35 mmol). The solution was warmed to room temperature and then warmed to reflux for 30 min, cooled, diluted with EtOAc and quenched with sat. NaHCO$_3$. The organic phase was separated and washed with sat. NaHCO$_3$ (2×5 mL) and brine (1×5 mL), dried over Na$_2$SO$_4$, filtered, concentrated and chromatographed (silica gel, 10–50% ethyl acetate in hexane) to give 59.7 mg (80%) of an off-white foam. Recrystallization from hot MeOH gave granular crystals: R$_f$=0.38 (silica gel, 50% EtOAc in hexane); [α]$^{20}_D$=−43° (c=0.45, CHCl$_3$); m.p. 229–31° (uncorr.); IR (film, NaCl) 3359, 2924, 2853, 1732, 1682, 1606, 1469, 1402, 1160, 756 cm$^-$; MS (CI) calc'd for C$_{28}$H$_{28}$N$_4$O$_3$: m/e 468.2162, found 468.2147; 425 (M−Ac), 399 (M−C$_5$H$_9$), 356 (M−(C$_5$H$_9$+Ac)).

Method B. To a solution of ardeemin (1.5 grams, 3.507 mmole) in 6 mL of acetic anhydride was added 0.6 mL of N,N-diisopropylethylamine. The reaction mixture was warmed to 60° C. for 24 hours. Progress of the reaction was monitored by TLC (EtOAc:Hexane, 3:4; R$_f$ 0.4 (acetate), R$_f$ 0.45 (ardeemin)). When the reaction was completed, the mixture was cooled to room temperature, diluted with 10 mL of chloroform and quenched by dropwise addition of sat. NaHCO, solution (added until all of the acetic anhydride was converted to sodium acetate). The organic phase was separated and washed with 5% citric acid (to remove N,N-diisopropylethylamine), dried over anhydrous sodium sulfate, filtered and concentrated. Chromatography (silica gel, 10 to 30% gradient, ethyl acetate in hexane) afforded 1.45 grams (88%) of product, m.p. 229.8–231.3° C., [α]$^{20}_D$= 51.1.

EXAMPLE 12

Allyl Ester (9(A)): A stream of argon was bubbled through a solution of the phenyl selenide (500 mg, 0.871 mmol, 5:1 mixture of diastereomers), allyl tributylstannane (0.543 mL, 1.74 mmol) and hexabutyldistannane (0.043 mL, 0.087 mmol) in toluene (8.7 mL, 0.1 M) for 40 minutes. The solution was then irradiated under argon for 9 hours using a medium pressure mercury lamp. Direct chromatography of the solution on silica gel (eluted with 5–30% ethyl acetate in hexane) gave 375 mg (94%) of a white foam as a 5:1 mixture of diastereomers.: R$_f$=0.60 (30% ethyl acetate in hexane).

The conditions as outlined for 10, 13, 14, 15, and 2 were followed to give 10(A), 13(A), 14(A), 15(A), and 2(A), respectively, with similar yields. $^1$H NMR data were obtained for 10(A), 13(A), 14(A), and 15(A),

EXAMPLE 13

"Allyl" 5-N-acetylardeemin (3(A)): Following Method A as outlined for 3 gave a 56% yield of a white solid. $^1$H NMR (400 MHz, CDCl$_3$): δ8.27 (d, J=8.1 Hz, 1H) 8.03 (b s, 1H), 7.79 (ddd, J=8.1, 7.0, 1.1 Hz, 1H) 7.72 (d, J=8.3 Hz, 1H) 7.52 (ddd, J=8,0, 7.0, 1.0 Hz, 1H) 7.35 (m, 2H) 7.21 (t, J=7.5 Hz, 1H) 5.93 (b s, 1H) 5.58 (m, 1H) 5.44 (q, J=7.2 Hz) 5.14 (d, J=17.0 Hz, 1H) 5.13 (d, 10.4 Hz, 1H) 4.57 (dd, J=10.7, 5.8 Hz, 1H) 3.25 (dd, J=13.2, 5.9 Hz, 1H) 2.65 (s, 3H) 2.61 (m, 3H) 1.48 (d, J=7.3 Hz, 3H) ppm; HRMS calculated for C$_{26}$H$_{24}$N$_4$O$_3$: m/e 440.1848, found 440.1852; 398 (M−Ac), 357 (M−Ac−C$_3$H$_5$).

Biological Results

1. Cytotoxicity

Relative cytotoxicity toward DC-3F hamster lung cells follows the ordering:

IC$_{50}$: 5-N-Ac-ardeemin (5.06 μM)<ardeemin (10.25 μM)<5-N-Ac "Allyl" ardeemin (17.39 μM)

In human leukemic CCRF-CEM cells, the relative ordering is as follows:

IC$_{50}$: Ardeemin (20.8 μM)<5-N-Ac-ardeemin (29.8 μM)<5-N-Ac "Allyl" ardeemin (53.3 μM)

Ardeemin derivatives are not particularly cytotoxic, and may be used as a modulator for a cytotoxic drug, or used directly against MDR cells.

II. Cross-Resistance

DC-3F/ADII p-glycoprotein MDR cells are 3 to 11 fold collaterally more sensitive to ardeemin derivatives than those of the parent DC-3F cells. Collateral sensitivity is also observed for verapamil. CCRF-CEM/VBL$_{100}$ human leukemic p-glycoprotein MDR cells are more sensitive to ardeemin derivatives than those of the parent CCRF-CEM cells.

Ardeemin derivatives are similarly effective against CCRF-CEM cells, but are less effective against cells resistant to VM-26 with mutated Topo II gene (CCRF-CEM/VM-1).

III. Transport of MDR Substrate

Ardeemin derivatives increase intracellular accumulation of antitumor agent VP-16 (a substrate for MDR), in CCRF-CEM human leukemic cells, as measured by the influx of [$^3$H]VP-16 during a 30 min period at 37° C.

5-N-Ac-Ardeemin (30 μM) and ardeemin (20 μM) increased VP-16 accumulation 66% and 33%, respectively. Verapamil (100 μM) also increased VP-16 accumulation. For MDR cells resistant to topo II inhibitor, VM-26 (CCRF/VM-1) ardeemin derivatives increased intracellular accumulation of VP-16. 5-N-Ac-ardeemin (30 μM) and ardeemin (20 μM) increased VP-16 accumulation 1.95-fold and 1.51-fold, respectively, whereas verapamil (100 μM) increased VP-16 accumulation 2.05-fold.

When CCRF-CEM cells are preloaded with [$^3$H] VP-16 for 30 min and then, without washing, treated with ardeemin derivatives for 30 min, the intracellular accumulation of VP-16 increased 3.9-fold by 30 μM of 5-N-Ac-ardeemin, 3.1-fold by 20 μM of ardeemin, and 4.2-fold by 100 μM of verapamil.

IV. Drug Combinations and the Reversal of MDR

For CCRF-CEM cells, vinblastine (VBL) and 5-N-acetylardeemin (5NAc-Adm) showed moderate synergism with regular tumnr cells with maximal synergy. (Combination index CI <1, =1, and >1 indicates synergism, additive effect, and antagonism, respectively.)

For CCRF-CEM/VBL$_{100}$ cells resistant to VBL (220-fold resistant) and to many other drugs compared with CCRF-CEM cells, VBL+5NAc-Adm (at 1:2000 combination ratio) showed marked synergism with CI=0.04, which allowed a 41-fold dose reduction for VBL, and a 55-fold dose reduction for 5NAc-Adm to achieve 98.4% inhibition of cell growth. Combination ratios from 1:2000 to 1:10,000 all showed synergism. This is apparently the strongest synergism among over 100 anticancer drug combinations examined so far using the quantitative combination index method.

Vinblastine very effectively kills wild type cancer cells (e.g. CCRF-CEM) Smith IC$_{50}$ of 0.0017 μM. In combination with 5NAc-Adm, it also kills drug resistant MDR cells (CCRF-CEM/VBL$_{100}$) with extremely strong synergism, which by far exceeded (>10-fold) activity against wild type parent tumor cells (CCRF-CEM).

TABLE 1

Cytotoxic Effects of 5-N-Acetylardeemin Analogs and Verapamil in Wild Type and MDR cells Cytototoxic Concentration in M

| Compounds | Hamster Lung Cells (DC-3F) | | | Hamster Lung Cells resistant to Actinomycin D IDC-3F/AD111 | | | Human CCRF-CEM | | | Human CCRF-CEM Resistant to Vinblastine (CCRF-CEM/VBL$_{100}$) | | | Human CCRF-CEM Resistant to VM-26 (CCRF-CEM/VM-26) | | |
|---|---|---|---|---|---|---|---|---|---|---|---|---|---|---|---|
| | $IC_{80}$ | $IC_{90}$ | $IC_{95}$ | $IC_{50}$ | $IC_{90}$ | $IC_{95}$ | $IC_{50}$ | $IC_{90}$ | $IC_{95}$ | $IC_{50}$ | $IC_{90}$ | $IC_{95}$ | $IC_{50}$ | $IC_{90}$ | $IC_{95}$ |
| 5-N-Acetyl-ardeemin | 5.08 | 50.96 | 111.8 | 1.59 | 91.38 | 362.6 | 29.8 | 351.2 | 812.6 | 25.42 | 64.42 | 88.37 | 49.09 | 4445.3 | $6 \times 10_5$ |
| 5-N-Acetyl-"allyl"-ardeemin | 17.39 | 56.2 | 83.74 | 5.21 | 34.7 | 66.13 | 53.28 | 888.0 | 2242.0 | 35.77 | 81.08 | 107.1 | 45.04 | 915.83 | $2.5 \times 10_4$ |
| Ardeemin | 10.25 | 30.89 | 44.56 | 2.01 | 24.56 | 57.54 | 20.76 | 65.66 | 97.14 | 10.85 | 27.93 | 38.52 | 29.19 | 88.82 | 299.15 |
| Verapamil | 45.13 | 84.36 | 104.4 | 4.06 | 25.31 | 47.17 | 189.8 | 1211.7 | 2276.0 | 145.0 | 811.93 | 1458.5 | 177.6 | 1483.2 | $1.5 \times 10_4$ |
| Adriamycin | 0.364 | 0.647 | 0.786 | 2.14 | 5.06 | 6.78 | 0.546 | 1.14 | 1.46 | 3.31 | 12.57 | 19.79 | 1.42 | 5.64 | 25.43 |
| M-AMSA | 0.002 | 0.012 | 0.0206 | 0.032 | 0.150 | 0.253 | 0.184 | 1.41 | 2.81 | 0.656 | 1.89 | 2.72 | 2.55 | 7.57 | 24.86 |

TABLE 1A

Cytotoxicity of Ardeemin Derivatives

| Compound | DC-3F (A) | DC-3F/ ADII (B) | DC-3F/ ADX (C) | (B)/(A) | (C)/(A) |
|---|---|---|---|---|---|
| | ($IC_{50}$ in μm) | | | | |
| Actinomycin D | 0.00021<br>0.00031<br>(0.00026 ±<br>0.00005) | 0.0909 | 1.232 | 349.6X Resistant | 4738.5X Very Resistant |
| 5-N-Ac-Ardeemin | 10.09<br>4.93<br>(7.51 ± 2.58) | 16.76 | 3.69 | 2.2X | 0.49X* |
| 8-Desmethyl-Ardeemin | 10.86<br>8.29<br>(9.58 ± 1.29) | 26.50 | 4.70 | 3.5X | 0.49X* |
| 5-N-Ac-8-desmethyl-Ardeemin | 37.70<br>20.94<br>(29.32 ± 8.38) | 14.63 | 3.98 | 0.50X* | 0.14X* |
| Desmethyl-DKP | 115.94<br>145.36<br>(130.7 ± 14.7) | 103.1 | 198.8 | 1.3X | 1.5X |
| Open ring-DKP | 384.70<br>425.56<br>(405.1 ± 20.4) | 1361.9 | 487.5 | 3.4X | 1.2X |

*Collaterally sensitive

TABLE 2

Two Drug Combination Study of Vinblastine and 5-N-Acetylardeemin on CCRF-CEM Cell Line at 72-HR Exposure Time. Based on XTT Assay.

Drug A: VINBLASTINE (uM)
Drug B: 5-N-ACETYLARDEEMIN (uM)

| Drug | Parameters | | |
|---|---|---|---|
| | Dm | M | r |
| A | .00168 | 2.53519 | .99212 |
| B | 18.79205 | .78648 | .98793 |

TABLE 2-continued

Two Drug Combination Study of Vinblastine and 5-N-Acetylardeemin on CCRF-CEM Cell Line at 72-HR Exposure Time. Based on XTT Assay.

CI values for actual experimental points of mixture of A and B at a non-constant ratio Mutually Exlusive Case

| Dose A | Dose B | Fa | CI Value |
|---|---|---|---|
| .005 | 10 | .98 | .64359 |
| .0025 | 10 | .9607 | .43001 |
| .001 | 10 | .6669 | .67184 |
| .0005 | 10 | .4236 | .12261 |
| .00025 | 10 | .2982 | 1.78808 |

TABLE 2-continued

Two Drug Combination Study of Vinblastine and 5-N-Acetylardeemin on CCRF-CEM Cell Line at 72-HR Exposure Time. Based on XTT Assay.

CI values for actual experimental points of mixture of A and B at a non-constant ratio
Mutually Non-exclusive Case

| Dose A | Dose B | Fa | CI value |
|---|---|---|---|
| .005 | 10 | .98 | .646 |
| .0025 | 10 | .9607 | .43386 |
| .001 | 10 | .6669 | .77128 |
| .0005 | 10 | .4236 | 1.38662 |
| .00025 | 10 | .2982 | 2.11692 |

For P388 leukemic cells, the $IC_{50}$ for Adr was reduced from 0.228 µM to 0.084 µM (2.7-fold reduction) in the presence of 0.42 µM of 5N-Ac-Ard-m ($IC_{50}$:43.7 µM). (See Table 2A.)

For P388/Dx leukemic cells (9.4-fold resistance to Adr), the $IC_{50}$ for Adr was reduced from 2.14 µM to 0.42 µM (5.1-fold reduction) in the presence of 2.80 µM of 5N-Ac-Ardm ($IC_{50}$: 65.9 EM). (See Table 2B.)

TABLE 3

Two Drug Combination Study of Vinblastine and 5-N-Acetylardeemin on Vinblastine-resistant CCRF-CEM Cell Line at 72-HR Exposure Time. Based on XTT Assay.

| Drug | $D_m$ | m | r |
|---|---|---|---|
| A | .37101 | 2.39234 | .99677 |
| B | 19.36733 | 1.23325 | .99592 |

CI values for actual experimental points of mixture of A and B at a non-constant ratio
Mutually Exclusive Case

| Dose A | Dose B | Fa | CI value |
|---|---|---|---|
| .25 | 10 | .9898 | .11217 |
| .1 | 10 | .9861 | .06167 |
| .05 | 10 | .9843 | .04189 |

TABLE 2A

Drug Combination of Adriamycin and 5-N-Acetyl-Ardeemin against P388 Cell Growth[a]

| Drug | Combination Index Value at | | | | | Parameters | |
|---|---|---|---|---|---|---|---|
| | ED50 | ED75 | ED90 | ED95 | $1C_{50}$ (µM) | m | r |
| Adriamycin | | | | | 0.228 ± 0.034 | 1.465 ± 0.053 | 0.990 ± 0.005 |
| 5-N-Ac-Ard. | | | | | 43.728 ± 19.514 | 0.866 ± 0.451 | 0.994 ± 0.015 |
| Combination (ratio = 1:5) | 0.409 ± 0.025 | 0.355 ± 0.095 | 0.306 ± 0.162 | 0.277 ± 0.204 | 0.084 + 0.419 (2.71X) (104.3X) | 1.882 ± 0.561 | 0.914 ± 0.079 |

[a]Cells (sensitive to adriamycin) were obtained from ATCC; 96 well microplate, 15,000 cell/well, N = 2. Platting cells on day 1, add drugs on day 2 and XTT assay on day 5.

TABLE 2B

Drug Combination of Adriamycin and 5-N-Acetyl-Ardeemin against P388/DX Cell Growth[a]

| Drug | Combination Index Value at | | | | | Parameters | |
|---|---|---|---|---|---|---|---|
| | ED50 | ED75 | ED90 | ED95 | $1C_{50}$ (µM) | m | r |
| Adriamycin | | | | | 2.139 ± 0.089 | 0.998 ± 0.017 | 0.971 ± 0.013 |
| 5-N-Ac-Ard. | | | | | 65.904 ± 1.102 | 0.875 ± 0.059 | 0.952 ± 0.005 |
| Combination (Ratio = 1:5) | 0.226 ± 0.068 | 0.166 ± 0.056 | 0.122 ± 0.046 | 0.0994 ± 0.040 | 0.416 + 2.078 (5.14X) (31.7X) | 1.355 ± 0.085 | 0.989 ± 0.004 |

[a]Cells resistant to adriamycin were obtained from Gleney; 96 well microplate, 25,000 cell/well, N = 2. Platting cells on day 1, add drugs on day 2 and XTT assay on day 5.

TABLE 3-continued

Two Drug Combination Study of Vinblastine and 5-N-Acetylardeemin on Vinblastine-resistant CCRF-CEM Cell Line at 72-HR Exposure Time. Based on XTT Assay.

CI values for actual experimental points of mixture of A and B at a non-constant ratio Mutually Non-exclusive Case

| Dose A | Dose B | Fa | CI value |
|---|---|---|---|
| .25 | 10 | .9898 | .11343 |
| .1 | 10 | .9861 | .06241 |
| .05 | 10 | .9843 | .04232 |

Dose reduction index values for actual experimental points of mixture of A and B at a non-constant ratio

| FA | Dose A | Dose B | Dose reduction Index | |
|---|---|---|---|---|
| .9898 | 2.51151 | 791.8969 | 10.04606 | 79.18968 |
| .9861 | 2.20329 | 614.2689 | 22.03287 | 61.42689 |
| .9843 | 2.09235 | 555.6899 | 41.84691 | 55.56899 |

TABLE 4

Two Drug Combination Study of Vinblastine and 5-N-Acetytardeemin on Vinblastine-resistant CCRF-CEM Cell Line at 72-HR Exposure Time. Based on XTT Assay. (large-scale study)

Drug A: VINBLASTINE ($\mu$M)
Drug B: 5-N-ACETYLARDEEMIN ($\mu$M)
Parameters

| Drug | ED50 | ED75 | ED90 | ED95 | Dm ($\mu$M) | m | r |
|---|---|---|---|---|---|---|---|
| A | | | | | .39341 | 1.73041 | .98506 |
| B | | | | | 29.78891 | 1.10066 | .98101 |

CI values for actual experimental points of mixture of A and B at a non-constant ratio Mutually Exclusive Case

| Dose A | Dose B | Fa | CI value |
|---|---|---|---|
| .05 | 10 | .9852 | .01864 |
| .025 | 10 | .9696 | .02304 |
| .01 | 10 | .9493 | .02811 |
| .005 | 10 | .817 | .09157 |
| .0025 | 10 | .4961 | .3469 |
| .001 | 10 | .3315 | .63871 |

CI values for actual experimental points of mixture of A and B at a non-constant ratio Mutually Non-exclusive Case

| Dose A | Dose B | Fa | CI value |
|---|---|---|---|
| .05 | 10 1:200 | .9852 | .01872 |
| .025 | 10 1:400 | .9696 | 02316 |
| .01 | 10 1:100 | .9493 | .02822 |
| .005 | 10 1:200 | .817 | .09203 |
| .0025 | 10 1:400 | .4961 | .34908 |
| .001 | 10 1:10,00 | .3315 | .64113 |

TABLE 4A

COMBINATION THERAPY OF ADRIAMYCIN & 5-N-ACETYL-ARDEEMIN OR VERAPAMIL IN B6D2F1 MICE BEARING P388/O TUMOR[a]

| Dose (mg/Kg)[b] | | | AWC (g)[c] | | | | | | | Days survived[d] Mouse number | | | | | MST[e] | % ILS[f] |
|---|---|---|---|---|---|---|---|---|---|---|---|---|---|---|---|---|
| Adr | 5NAc-Ardm | VPML[g] | D 0 | D 4 | D 6 | D 8 | D 14 | D 16 | D 18 | 1 | 2 | 3 | 4 | 5 | | |
| — | — | — | 23.6 | +1.2 | +2.6 | +5.1 | — | — | — | 6.25 | 7.26 | 8.0 | 8.0 | 9.0 | 7.58 | 0 |
| — | — | — | 23.6 | +1.9 | +4.9 | +4.4 | — | — | — | 6.6 | 6.5 | 7.25 | 8.5 | 8.6 | | |
| 0.5 | — | — | 23.4 | +0.1 | +0.8 | +1.9 | +4.6 | +5.9 | +6.4 | 15.5 | 16.0 | 17.0 | 18.0 | 20.0 | 17.3 | +128 |
| 1.0 | — | — | 23.2 | −0.8 | +0.5 | +0.9 | +4.0 | +6.4 | +5.7 | 16.0 | 19.0 | 19.0 | 20.5 | 21.0 | 19.1 | +152 |
| 2.0 | — | — | 24.0 | −1.0 | −1.0 | −0.9 | −1.6 | −0.5 | +2.4 | 19.0 | 20.5 | 21.0 | 22.5 | 22.5 | 21.1 | +178 |
| 3.0 | — | — | 24.0 | −0.8 | −1.3 | −1.9 | −4.8 | −3.8 | −2.2 | 12.5[h] | 16.0[h] | 20.5 | 24.6 | 26.5 | 19.8 | +181 |
| — | 70 | — | 23.8 | +1.6 | +3.7 | +5.2 | — | — | — | 8.5 | 7.0 | 8.25 | 6.5 | 8.5 | 7.75 | +2 |
| 0.5 | 70 | — | 23.6 | −0.3 | +0.1 | +0.4 | +5.4 | +6.4 | +5.8 | 16.6 | 18.0 | 18.6 | 19.0 | 20.5 | 18.5 | +144 |
| 1.0 | 70 | — | 23.7 | −0.6 | −0.2 | +0.1 | +1.8 | +5.0 | | 18.5 | 19.0 | 20.5 | 21.0 | 25.0 | 20.8 | +174 |
| 2.0 | 70 | — | 23.5 | −0.7 | −1.6 | −2.0 | +0.2 | +0.9 | +2.5 | 19.5 | 20.5 | 21.0 | 23.6 | 25.0 | 21.9 | +189 |
| — | — | 70 | 23.6 | −0.9 | +1.6 | +3.5 | — | — | — | 7.0 | 7.0 | 8.0 | 8.0 | 8.6 | 7.7 | +1 |
| 0.5 | — | 70 | 23.0 | −1.3 | −0.4 | −0.3 | +1.5 | +4.2 | +4.5 | 17.0 | 18.0 | 18.0 | 19.0 | 20.5 | 18.6 | +144 |
| 1.0 | — | 70 | 23.7 | −1.9 | −2.0 | −1.2 | −0.8 | +0.5 | +2.0 | 13.25[i] | 13.26[i] | 18.5 | 20.5 | 22.0 | 17.6 | +131 |
| 2.0 | — | 70 | 23.4 | −1.5 | −1.8 | −2.3 | −3.8 | −2.7 | −2.1 | 4.5[j] | 14.5[j] | 15.5[j] | 23.0 | 26.5 | 16.8 | +122 |

[a]Male BDF mice were inoculated P388/O, 10[6] cells/mouse, i.p. at day 0, and treated by adriamycin, 5-N-acetyl-ardeemin and verapamil starting day 1, QDX4, QWX2. There were five mice every dose and ten mice in control.
[b]Adr., adriamycin; 5NAcArd., 5-N-acetyl-ardeemin; VPML, verapamil
[c]AWC, average weight change
[d]Survival time were recorded based on the time of death with the following decimal values: 8AM (0.0), 1PM (0.26), 5PM (0.5).
[e]% ILS, % Increase in lifespan.
[g]Verapamil: 70 mg/kg/day was for initial three doses, and 35 mg/kg/day for the last five doses.
[h]Two mice died of toxicity of drugs on day 12.5 and 15 respectively.
[i]Two mice died of toxicity of drugs on day 13.25.
[j]Three mice died of toxicity of drugs on day 4.5, 14.5, and 15.5 respectively.

TABLE 4B

COMBINATION THERAPY OF ADRIAMYCIN & 5-N-ACETYL-ARDEEMIN OR VERAPAMIL IN $B_6D_2F_1$ MICE BEARING P388/DX TUMOR[a]

| Dose (mg/Kg)[b] | | | AWC (g)[c] | | | | | | | Mouse number / Days survived[d] | | | | | MST[e] | % ILS[f] |
|---|---|---|---|---|---|---|---|---|---|---|---|---|---|---|---|---|
| Adr. | 5NAc-Ard. | VPML[g] | D 0 | D 4 | D 6 | D 8 | D 10 | D 12 | D 14 | 1 | 2 | 3 | 4 | 5 | | |
| — | — | — | 24.0 | +1.3 | +3.3 | +4.0 | — | — | — | 6.5 | 7.0 | 8.0 | 8.0 | 8.5 | 7.55 | 0 |
| — | — | — | 23.2 | +1.1 | +2.9 | +4.3 | — | — | — | 6.25 | 7.25 | 7.5 | 7.5 | 9.0 | | |
| 0.5 | — | — | 23.4 | +0.1 | +2.1 | +3.8 | +4.8 | +4.9 | — | 7.5 | 10.5 | 12.25 | 12.25 | 14.0 | 11.3 | +49 |
| 1.0 | — | — | 23.6 | −0.5 | +0.4 | +1.7 | +4.6 | +5.4 | — | 11.5 | 12.25 | 13.25 | 13.25 | 16.0 | 13.25 | +75 |
| 2.0 | — | — | 23.5 | −1.0 | −0.6 | −0.5 | +1.0 | +1.4 | +2.2 | 14.0 | 15.0 | 15.25 | 16.5 | 17.0 | 15.55 | +106 |
| 3.0 | — | — | 23.7 | −0.9 | −1.3 | −1.2 | −1.7 | −2.3 | −2.6 | 14.0[h] | 14.0[h] | 17.5 | 21.0 | 21.0 | 17.4 | +130 |
| — | 70 | — | 23.4 | +1.0 | +2.4 | +5.6 | — | — | — | 6.5 | 7.25 | 8.0 | 8.0 | 8.0 | 7.55 | 0 |
| 0.5 | 70 | — | 23.5 | −0.2 | +0.4 | +1.9 | +3.4 | +3.2 | +5.5 | 10.25 | 11.5 | 13.25 | 14.0 | 15.0 | 12.8 | +69 |
| 1.0 | 70 | — | 23.2 | −1.2 | −1.3 | +0.9 | +0.5 | +0.6 | +2.4 | 13.25 | 15.0 | 15.0 | 16.25 | 16.25 | 15.15 | +101 |
| 2.0 | 70 | — | 23.4 | −1.3 | −1.7 | −1.6 | −2.1 | −1.4 | +0.3 | 16.5 | 18.0 | 19.0 | 20.5 | 21.0 | 19.0 | +151 |
| — | — | 70 | 23.6 | −1.2 | +2.5 | +5.1 | — | — | — | 6.5 | 7.25 | 8.25 | 8.25 | 9.25 | 7.9 | +5 |
| 0.5 | — | 70 | 22.8 | −1.9 | +0.1 | +1.7 | +2.8 | +4.9 | +5.7 | 7.5 | 12.5 | 13.25 | 14.0 | 15.25 | 12.5 | +66 |
| 1.0 | — | 70 | 23.6 | −1.9 | −1.2 | −1.2 | −1.0 | +0.1 | +4.4 | 13.25 | 14.0 | 15.0 | 16.0 | 16.0 | 14.85 | +97 |
| 2.0 | — | 70 | 23.2 | −2.6 | −2.4 | −2.1 | −2.3 | −2.5 | −1.6 | 4.0[i] | 17.25 | 18.0 | 20.5 | 21.0 | 16.15 | +114 |

[a]Male BDF mice were inoculated P388/DX, $10^6$ cells/mouse, i.p. at day 0, and treated by adriamycin, 5-N-acetyl-ardeemin and verapamil starting day 1, QDX4, QWX2. There were five mice at every dose and ten mice in the control.
[b]Adr., adriamycin; 5NAcArd., 5-N-acetyl-ardeemin; VPML, verapamil
[c]AWC, average weight change
[d]Survival times were recorded based on the time of death with the following decimal values: 8AM (0.0), 1PM (0.25), 5PM (0.5).
[e]MST, Mean survival time.
[f]% ILS, % increase in lifespan.
[g]Verapamil: 70 mg/kg/day was for initial three doses, and 35 mg/kg/day for the last five doses.
[h]Two mice died of toxicity of drugs on day 14.
[i]One mouse died of toxicity of drugs on day 4.

TABLE 4C

COMBINATION THERAPY OF ADRIAMYCIN, VINBLASTINE AND DES-ME-N-ACETYL-ARDEEMIN IN $B_6D_2F_1$ MICE BEARING P388/0 TUMOR[a]

| Dose (mg/kg)[b] | | | AWC (g)[c] | | | | | Mouse number (Days survived[d]) | | | | | MST[e] | % ILS[f] |
|---|---|---|---|---|---|---|---|---|---|---|---|---|---|---|
| Adr. | VBL | DMNAA | D 0 | D 3 | D 6 | D 9 | D 12 | 1 | 2 | 3 | 4 | 5 | | |
| — | — | — | 18.2 | +0.6 | +2.6 | — | — | 7.25 | 8.0 | 8.0 | 8.5 | 9.0 | | |
| — | — | — | 17.6 | +1.0 | +1.9 | +4.2 | — | 7.5 | 8.0 | 8.0 | 9.25 | 10.25 | 8.33 | 0 |
| — | — | 50.0 | 17.8 | +0.8 | +1.8 | — | — | 7.0 | 8.5 | 8.5 | 9.0 | 9.0 | 8.40 | +1 |
| 3.0 | — | — | 18.2 | −0.4 | +0.6 | +1.9 | +4.6 | 10.5 | 13.5 | 14.5 | 14.5 | 15.0 | 13.60 | +63 |
| 5.0 | — | — | 17.8 | −0.6 | +0.2 | +0.8 | +1.0 | 10.5 | 14.0 | 16.0 | 17.0 | 18.0 | 15.10 | +81 |
| 3.0 | — | 50.0 | 18.3 | −0.8 | −0.1 | +0.7 | +2.3 | 9.0 | 13.5 | 15.5 | 16.0 | 16.0 | 14.00 | +68 |
| 5.0 | — | 50.0 | 18.2 | −1.8 | −1.0 | −2.2 | −2.7 | 15.0 | 18.0 | 22.25 | 23.0 | 25.5 | 20.75 | +149 |
| — | 1.5 | — | 18.0 | −0.7 | +0.6 | −0.1 | +3.0 | 9.5 | 13.0 | 13.0 | 13.0 | 14.0 | 13.25[g] | +59 |
| — | 3.0 | — | 18.2 | −1.7 | −0.9 | +1.0 | +1.8 | 5.0 | 6.0 | 9.5 | 15.5 | 16.0 | 13.67[h] | +64 |
| — | 1.5 | 50.0 | 18.2 | −1.9 | +0.3 | −2.2 | −1.7 | 4.0 | 14.0 | 14.0 | 14.0 | 16.0 | 14.50[i] | +74 |
| — | 3.0 | 50.0 | 18.1 | −2.3 | −3.1 | −0.8 | +0.4 | 4.5 | 5.0 | 5.0 | 12.0 | 19.0 | 15.50[j] | +80 |

[a]Male BDF mice were inoculated with P388/O, $10^6$ cell/mouse, i.p. on day 0; and started treatment on day 1, i.p., Q5Dx5, besides mice with dose VBL 3.0 and VBL 3.0 mg/kg + DMNAA 50 mg/kg, only one injection i.p., on day 1. There were five mice at every dose and ten in the control.
[b]Adr.: adriamycin; VBL; vinblastine; DMNAA; 8-Des-Me-5-N-acetyl-ardeemin.
[c]AWC; average weight change.
[d]Survived days were recorded based on the time of death with the following decimal values: 9:00 am (0.0), 1:00 pm (0.25), 5:00 pm (0.5).
[e]MST: mean survival time
[f]% increase in lifespan
[g]One mouse died of toxicity of drug on day 9, and was excluded from calculation.
[h]Two mice died of toxicity of drug on day 5 and 6, and were excluded from calculation.
[i]One mouse died of toxicity of drugs on day 4, and was excluded from calculation.
[j]Three mice died of toxicity of drugs on day 4, 5 and 5 respectively, and were excluded from calculation.

N-Acetylardeemin is non-toxic to HCT116 cells at concentrations up to 2.2 $\mu$M. At higher concentrations the material has diminished solubility. N-Ac-adm at 2.2 $\mu$M was co-incubated with paclitaxel for 72 hr with HCT116 cells or the multidrug resistant (MDR) cell line HCT116(VM)46. The results are summarized in the table below. All drug exposures were for 72 hr and cytotoxicity was measured by XTT tetrazolium dye assay.

TABLE 5

In Vitro Cytotoxicity Results for N-Acetylardeemin

| | IC$_{50}$ (nM) | | |
|---|---|---|---|
| | HCT116 | HCT116 (VM) 46 | R/S ratio |
| paclitaxel | 2.0 × 10$^3$ | 258 | 132 |
| paclitaxel + N-Ac-adm | 1.6 × 10$^3$ | 14 | 9 |

These results suggest that a non-toxic concentration of 2.2 μM N-Ac-adm is able to substantially reverse paclitaxel resistance mediated by the P-glycoprotein efflux pump. This would be consistent with results seen with adriamycin in animals assuming resistance in them was due to P-glycoprotein. The degree of paclitaxel resistance observed in the presence of N-Ac-adm is comparable to the resistance observed with paclitaxel and 15 μM verapamil or 0.03% cremophor EL in HCT116(VM)46 cells (R/S ratio=4).

TABLE 6

Inhibition of Cell Growth by Ardeemin Derivatives

| | Human Acute Lymphoplastic T Cells | |
|---|---|---|
| | CCRF-CEM | CCRF-CEM/VBL |
| Compounds | (IC$_{50}$ in μM) | |
| Diketopiperazine 14(B) | 147.9 | 147.2 |
| N-Aceyl-Diketopiperazine 14(E) | 225.1 | 540.9 |
| 5-N-Acetylardeemin | 17.18 | 6.99 |
| Imide-Acetate 14(A) | 48.11 | 39.66 |
| Imide-BOC 14(C) | 88.73 | 65.37 |
| Imide-Diacetate 14(D) | 62.53 | 37.14 |

TABLE 5A

Structure Activity Relationship of Reverse Prenyl Compounds: Comparison of IC$_{50}$ Values (in μm) in CCRF-CEM Subcell Lines

| Compound | CCRF-CEM | CCRF-CEM/VLB | CCRF-CZM/VM-1 |
|---|---|---|---|
| 5N-formyl-8-desMe-DKP | 199.7 μm | 372.2 μm | NA |
| 5N-Ac-8-desMe-DKP | 21.4 μm<br>22.7 μm<br>(22.1 ± 0.7) | 6.9 μm*<br>32.9 μm<br>(19.9 ± 13.0) | 35.8 μm |
| 5N-Bn-8-desMe-DKP | 19.2 μm | 12.5 μm* | NA |
| DKP 14(B) | 142.9 μm<br>120.0 μm<br>(131.5 ± 11.5) | 135.4 μm<br>53.8 μm*<br>(94.6 ± 40.8) | 178.5 μm |
| 5N-F$_3$-Ac-DKP 14F(E) | 32.8 μm<br>31.5 μm<br>(32.2 ± 0.7) | 24.6 μm* | 41.0 μm |
| 5N F$_3$-Ac-Ard  3F | 37.5 μm | 17.2 μm* | 52.6 μm |
| 5N F$_3$-Amide-Ac-DKP | 26.8 μm<br>32.6 μm<br>(29.7 ± 2.9) | 23.7 μm* | 33.0 μm |
| Imide Di-Ac-DKP Amide 14(D) | 102.8 μm<br>64 μm<br>(83.4 ± 23.4) | 51.4 μm*<br>58 μm*<br>(54.7 ± 3.3) | 81.4 μm<br>89 μm<br>(85.2 ± 4.0) |
| 5N-Ac-DKP 14(E) | 225.1 μm<br>568 μm<br>(396.6 ± 171.5) | 540.9 μm<br>147 μm<br>(344.0 ± 197) | 32.4 μm |
| Imide-Ac-DKP 14(A) | 48.1<br>47.9<br>87.0<br>(61.0 ± 13.1) | 39.7 μm*<br>36.2 μm<br>(38.0 ± 1.8) | 50.0 μm |
| Imide-BOC-DKP 14(C) | 88.3 μm<br>32.0 μm<br>(204.2 ± 115.9) | 65.4 μm*<br>120 μm<br>(92.9 ± 27.3) | 205 μm |

*Collaterally sensitive when compared with the parent cell line

TABLE 6A

Effects of reverse prenyl compounds on intracellular accumulation
of [$^3$H] Vinblastine in CCRF-CEM and CCRF-CEM/VLB-100 cells*

| | CCRF-CEM | | | | CCRF-CEM/VLB-100 | | | |
|---|---|---|---|---|---|---|---|---|
| | Without wash | | Washed | | Without wash | | Washed | |
| Compounds (30 μM) | fmole/ 10³ cells | % Increased | fmole/ 10³ cells | % Increased | fmole/ 10³ cells | % Increased | fmole/ 10³ cells | % Increased |
| DMSO (Control) | 31.13 ± .693 | — | 26.98 ± .343 | — | 7.90 ± 1.0 | — | 2.32 ± .090 | — |
| | 34.67 | 11.35 | 28.80 | 6.72 | 28.09 | 220.33 | 6.85 | 195.22 |
| Diketopiperazine (DKP) | 35.84 | 15.12 | 28.51 | 5.67 | 10.81 | 34.38 | 3.33 | 43.52 |
| DKP-Amide Acetate | 35.08 | 12.80 | 29.54 | 9.49 | 12.88 | 60.55 | 3.59 | 54.59 |
| DKP-Imide Acetate | 34.87 | 12.00 | 30.18 | 11.77 | 18.93 | 114.30 | 4.52 | 94.52 |
| DKP-Imide tert-Butyl Carbonate | 35.56 | 14.22 | 30.29 | 12.26 | 25.44 | 222.07 | 6.10 | 182.62 |
| DKP-Imide Acetate Amide Acetate | 34.54 | 10.93 | 28.36 | 5.10 | 15.92 | 101.58 | 4.01 | 72.89 |
| DKP-Imide Acetate Amide Tri-F Acetate | 34.49 | 10.77 | 28.83 | 7.21 | 18.55 | 134.83 | 4.89 | 110.57 |
| DKP-Amide-Trifluoro Acetate | 33.34 | 7.09 | 28.75 | 6.55 | 23.34 | 195.45 | 5.77 | 148.58 |
| Gypsetin (cis/cis) | 34.22 | 9.90 | 28.99 | 7.43 | 30.11 | 281.24 | 6.75 | 190.75 |
| Gypsetin (cis/trans) | 34.36 | 10.38 | 29.15 | 8.02 | 18.32 | 108.58 | 4.57 | 96.79 |
| Gypsetin (trans/trans) | 32.68 | 14.97 | 29.77 | 10.32 | 27.38 | 248.44 | 5.88 | 157.71 |
| Ardeemin | 34.68 | 11.38 | 29.94 | 10.96 | 22.84 | 189.18 | 5.42 | 133.32 |
| 5N-Acetyl Ardeemin | 37.45 | 20.29 | 32.73 | 21.29 | 35.44 | 348.63 | 12.78 | 450.36 |
| "Allyl" 5N-Acetyl Ardeemin | 33.35 | 7.10 | 28.88 | 8.97 | 27.21 | 244.53 | 6.18 | 188.27 |
| 5N-Acetyl-8-Desmethyl Ardeemin | 33.13 | 8.41 | 29.33 | 8.70 | 33.53 | 324.47 | 7.66 | 230.02 |
| 5N-Tri-F Acetyl Ardeemin | 34.01 | 8.23 | 28.44 | 5.38 | 32.68 | 313.76 | 7.28 | 213.44 |

*Cells were preloaded with [$^3$H] Vinblastine for 15 min, washed 2 times (or without wash) with 100 ml cold medium to remove extracellular [$^3$H] Vinblastine followed by 30 min incubation at 37° C., with or without a reverse prenyl compound or an MDR-reversing agent. Cells were then separated from radioactive medium by microfuge oil-layer method. Extracellular space counts carried down by cells ($^3$H-Inulin space) were subtracted from the total radioactive counts.

TABLE 6B

IC$_{50}$ of Vinblastine in CCRF-CEM, CCRF-CEM/VBL, CCRF-CEM/VM-1 Cells
in the Presence and Absence of MDR Reversing Agents

| | IC$_{50}$ Values of Reversing Agent (μM) | | | Concentration of Reversing Agent Added (μM) | | | IC$_{50}$ Values of VBL in the Presence of Reversing Agent (nM) | | | | |
|---|---|---|---|---|---|---|---|---|---|---|---|
| MDR Reversing Agents | CCRF-CEM | CCRF-CEM/VBL | CCRF-CEM/VM-1 | CCRF-CEM | CCRF-CEM/VBL | CCRF-CEM/VM-1 | CCRF-CEM (A) | CCRF-CEM/VBL (B) | CCRF-CEM/VM-1 (C) | (b)/(a) | (C)/(A) |
| VBL alone | — | — | — | — | — | — | 0.83 | 832 | 0.45 | 761 | 0.54 |
| VBL + 5N-Ac-Ard | 29.17 | 18.1 | 39.4 | 15 | 16 | 20 | 0.21 | 0.11 | 0.04 | 0.53 | 0.19 |
| + 5N-tri-F-Ac-Ard | 37.6 | 17.2 | 528 | 12 | 16 | 20 | 0.09 | 0.02 | 0.08 | 0.22 | 0.87 |
| + 5N-Ac-B-Desmethyl-Ard | 22.7 | 32.9 | 35.8 | 17 | 17 | 20 | 0.35 | 0.17 | 0.02 | 0.49 | 0.06 |
| + 8-Desmethyl-Ard | 14.3 | 18.8 | 18.1 | 10 | 10 | 10 | 0.19 | 0.15 | 0.13 | 0.83 | 0.70 |
| VBL + DKP | 142.8 | 135.4 | 178.5 | 50 | 50 | 50 | 0.35 | 81.2 | 0.29 | 232.5 | 0.83 |
| + 5N-tri-F-Ac-DKP | 32.8 | 24.8 | 40.89 | 15 | 15 | 20 | 0.32 | 102.4 | 0.29 | 320.0 | 0.91 |
| VBL + Verapamil | 295.8 | 117.7 | 117.8 | 75 | 80 | 100 | 0.15 | 0.10 | 0.18 | 0.87 | 1.07 |

Discussion

In principle, compounds 1, 2, and 3 could be obtained from the hypothetical tricyclic amino acid 4 which is formally derived from tryptophan precursor 5 by alkylative cyclization (FIG. 1; protection states of 4 and 5 are unspecified). No method for achieving a transformation of the type 5 to 4 was known in the tryptophan series prior to the present invention. The introduction of a 1,1-dimethallyl moiety at the gem-dimethyl carbon is unexpected in the art to afford a practical yield via direct alkylative cyclization (path a). In the corresponding tryptamine series where the issue of stereochemical information transfer does not exist, two methods for the direct introduction of a 1,1-diethylpropynyl group have been reported to give a modest yield. (Hino, T.; Hasumi, K.; Yamaguchi, H.; Taniguchi, M.; Nakagawa, M., Chem. Pharm. Bull., 1985, 33, 5202; Nakagawa, M.; Ma, J.; Hino, T., Heterocycles, 1990, 30, 451) Direct alkylative cyclization of tryptamine derivatives with prenyl halides occurs exclusively at the primary carbon to give the undesired 3,3-dimethylallyl regioisomer. (Bocchi, V.; Casnati, G.; Marchelli, R., Tetrahedron, 1978, 34, 929) The present inventors expected path b to be more useful wherein a heteroatom-mediated oxidative cyclization of 5 leads to 6. Numerous examples of protonic or oxidative cyclizations of the type 5 to 6 are known in both the tryptamine and tryptophan series. However, these methods did not provide efficient stereocontrol during cyclization (5 to 6) nor for subsequent activation in the substitution by the reverse-prenyl nucleophile (6 to 4). (Hino, T.; Nakagawa, M., in The Alkaloids; Brossi, A., ed.; Academic Press, Inc., New York, 1988, 34, 1; Bruncko, M.; Crich, D., J. Org. Chem., 1994, 59, 4239) Following suitable activation, a resultant cationoid species would serve to alkylate a reverse-prenyl nucleophile. This strategy relies on an expected strong preference for a cis-interlocked 5,5-ring system to enforce cis stereochemistry in both the oxidative cyclization and alkylation steps. Furthermore, this approach requires that efficient transmission of stereochemical information from the tryptophan stereogenic center to the emerging junction in the heteroatom-mediated cyclization. The present invention implements these concepts in the total syntheses of 1, 2, and 3.

Figure 4:
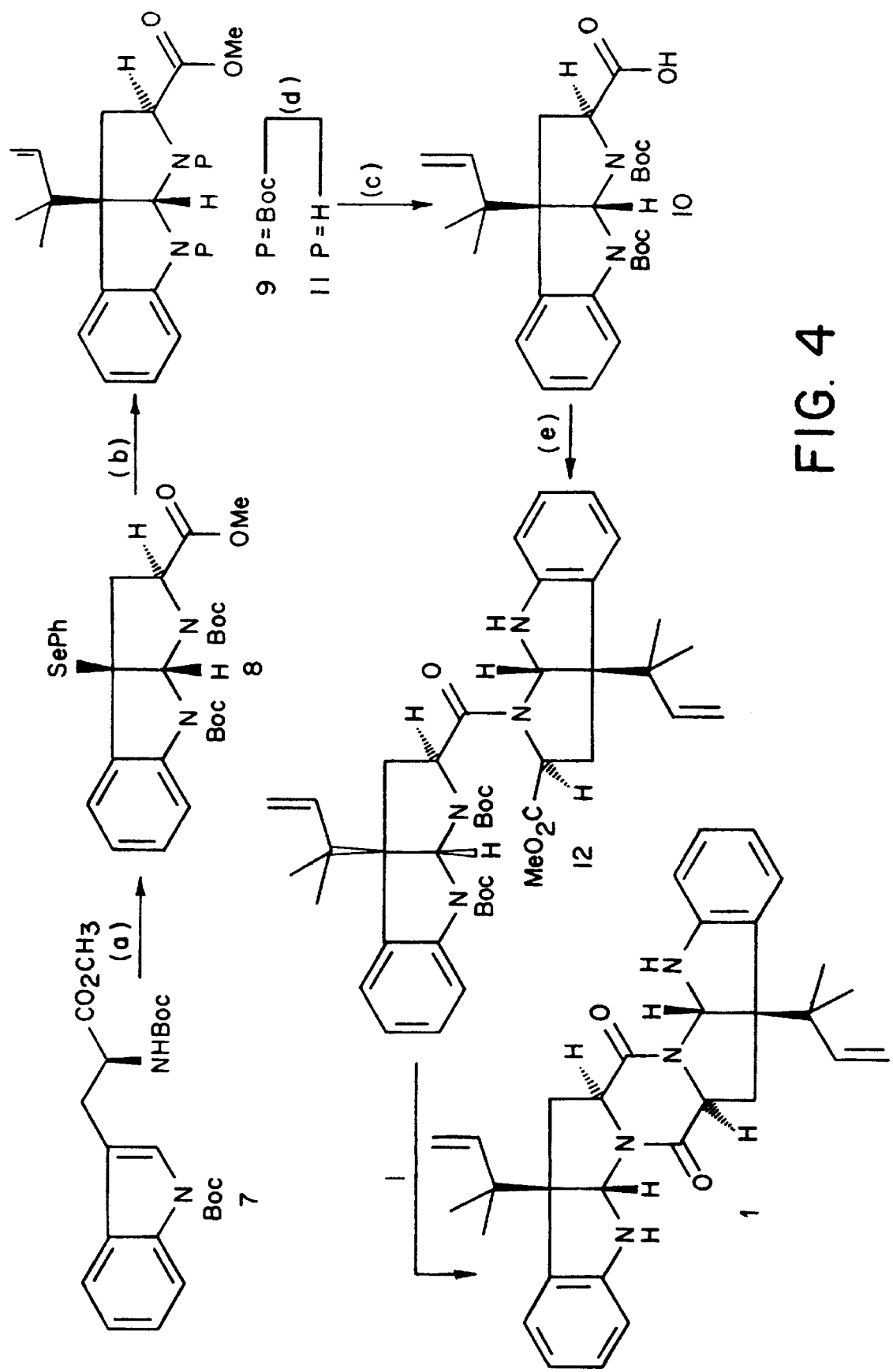
FIG. 4 shows the synthesis of amauromine 1. (a) N-PSP, PTSA, $Na_2SO_4$, $CH_2Cl_2$, 78% (9:1, β:α); (b) MeOTf, (prenyl)$SnBu_3$, 2,6-di(t-Bu)-pyridine, $CH_2Cl_2$, 60%; (c) 1 N NaOH, THF/MeOH, 98%, separate isomers; (d) TMSI (2.4 equiv), MeCN, 0° C. to room temperature; (e) 11 (1.1 equiv), 10 (1 equiv), BOP—Cl (1.1 equiv), $Et_3N$ (2.3 equiv); $CH_2Cl_2$, 78%; (f) TMSI (4 equiv), MeCN, 0° C. to room temperature, 58%.

The starting material used in the present method of preparing 1 was bis(Boc)tryptophan methyl ester 7 (FIG. 4; prepared in two steps from L-tryptophan: Franzen, H.; Grehn, L.; Ragnarsson, U., J. Chem. Soc., Chem. Commun., 1984, 1699. However, as used herein, 7 was preferably prepared from L-tryptophan methyl ester by treatment with $BOC_2O$ (3 equiv), NaOH (5 equiv), and $NBu_4HSO_4$ (10 mol %) in $CH_2Cl_2$ (91i yield). This compound reacted with N-phenylselenophthalimide (Nicolaou, K. C.; Claremon, D. A.; Barnette, W. E.; Seitz, S. P. J. Am. Chem. Soc., 1979, 101, 3704) and catalytic p-toluenesulfonic acid to give a 78% yield of 3-selenylated pyrroloindole 8 as an inseparable 9:1 mixture of diastereomers, following the equilibration of an initial 1:1 mixture. Treatment of 8 with methyl triflate and prenyl tributylstannane in the presence of 2, 6-di-tert-butylpyridine (Naruta, Y.; Nishigaichi, Y.; Maruyama, K., Chem. Lett. 1986, 1857) gave a 60% yield of 9, bearing the reverse prenyl group at the desired position as an unchanged 9:1 diastereomeric mixture. Unexpectedly, no products due to simple proton loss in the presumed benzylic cation intermediate were observed. (Without intending to be bound to any mechanism, applicants suggest that this stability arises from the reluctance of the ring system to approach planarity, wherein the bulky Boc groups would be forced into close proximity.) After saponification of 9 to acid 10, chromatographic separation of the diastereomers was possible. In addition, the Boo groups could be simultaneously removed to give aminal 11, which was again isolated as a single diastereomer.

Regarding the total synthesis of 1, BOP chloride-mediated coupling of 10 and the hindered amine 11 proceeded in 78% yield to give peptide 12. (Attempted couplings with other reagents were uniformly unsuccessful. For an additional example of a BOP chloride-mediated coupling of a hindered secondary amine where other reagents failed, see: Danishefsky, S. J.; Harrison, P. J.; Webb, R. R., II; O'Neil, B. T., J. Am. Chem. Soc., 1985, 107, 1421.) Removal of the remaining Boc groups with iodotrimethylsilane was accompanied by spontaneous cyclization to furnish directly, amauromine (1) in five linear steps from bis (Boc) -tryptophan methyl ester and an overall yield of 16%. The amauromine so produced was identical in all respects with an authentic sample of the natural material.

Figure 5:
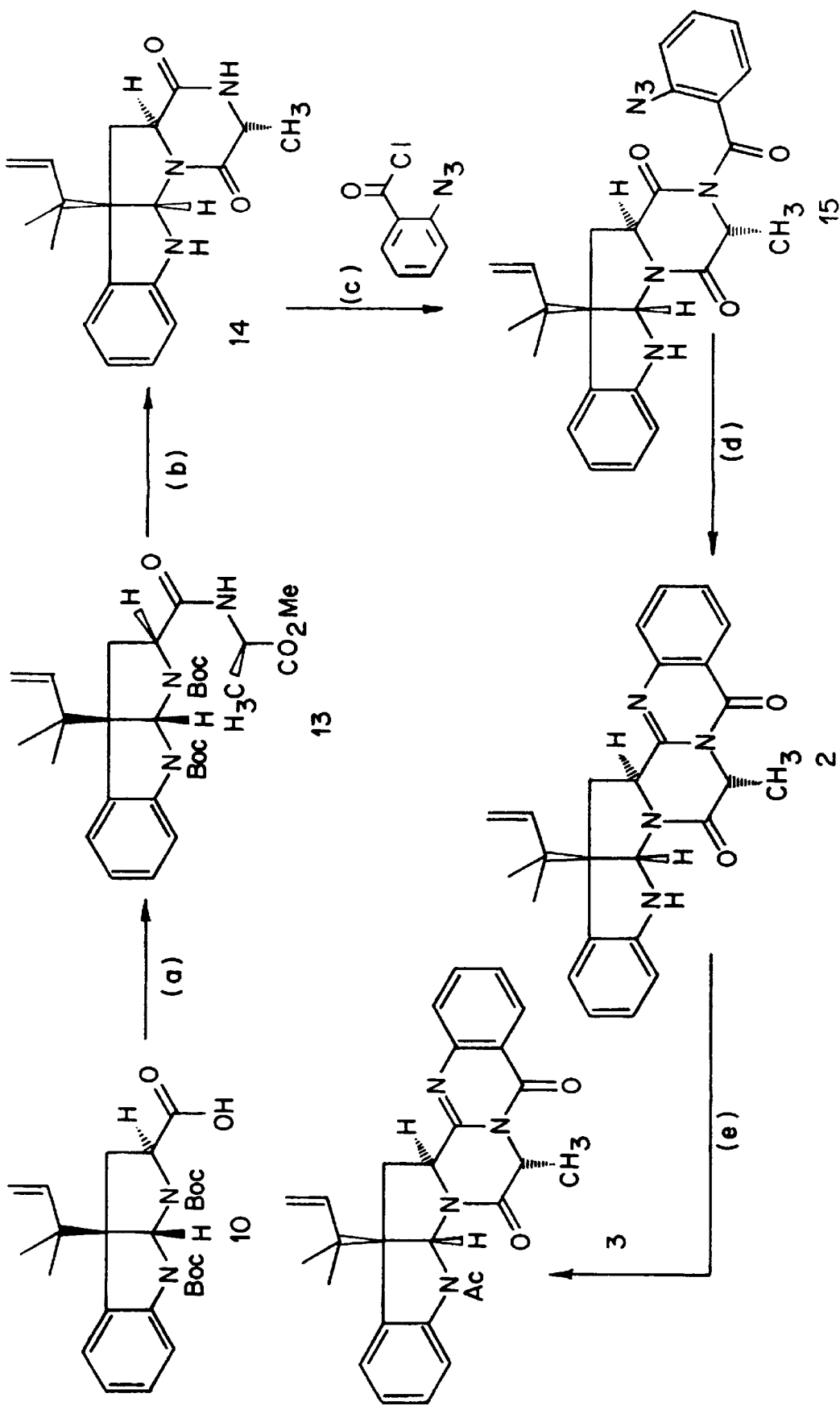
FIG. 5 shows the synthesis of N-acetylardeemin starting from tricyclic intermediate 10. (a) cyanuric fluoride, pyridine, $CH_2Cl_2$ −15° C., D-Ala-OMe.HCl, $NaHCO_3$, $H_2O/CH_2Cl_2$, 71%; (b) 1. TMSI, MeCN; 0° C.; 2. $NH_3$, MeOH, DMAP, 76% overall; (c) KHMDS, THF, −78° C., 80%; (d) $PBu_3$, PhH, 72%; (e) LDA, THF, −78° C. to RT, AcCl, reflux, 82%.
Figure 6:
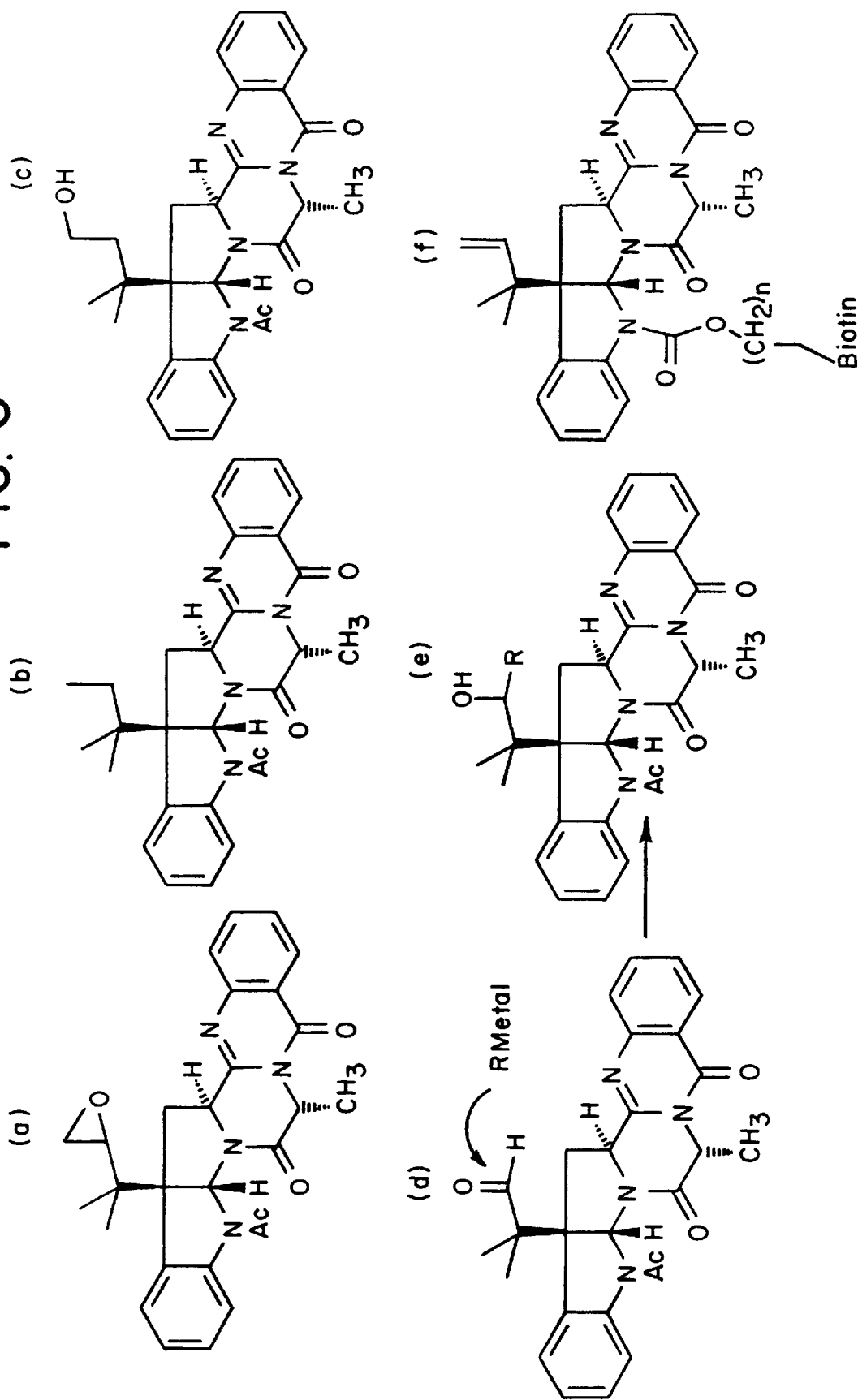
FIG. 6 shows various analogues of N-acetylardeemin and methods of preparation thereof. (a) N-acetylardeemin epoxide (useful for attachment to a polymer support and as a suicide inhibitor), prepared by epoxidation of N-acetylardeemin; (b) dihydro-N-acetylardeemin, prepared by hydrogenation of N-acetylardeemin; (c) hydroxy-dihydro-N-acetylardeemin, prepared by hydroboration/oxidation or by epoxidation, followed by reductive ring cleavage with lithium/ammonia; (d) aldehyde analogue of N-acetylardeemin (active site alkylator), prepared by ozonolysis or osmolysis, followed by periodate oxidation; (e) organometallic addition to N-acetylardeemin aldehyde (d) or hydride reduction thereof; (f) biotinylated N-acetylardeemin for use in affinity chromatography, prepared from polymethylene ester carbamte derivative of N-acetylardeemin.

Coupling of 10 with D-alanine methyl ester (FIG. 5) using standard agents afforded, in addition to the expected 13, considerable amounts of a minor product presumably arising through epimerization of the "i-tryptophan" stereogenic center. Other attempted activating agents include DCC/DMAP, DCC/HOBT, isobutyl chloroformate, and BOP chloride. However, in situ generation of the acyl fluoride of 10 followed by its condensation with D-alanine methyl ester resulted in clean conversion (71%) to peptide 13. (Carpino, L. A.; Mansour, E. -S. M. E.; Sadat-Aalaee, D., J. Org. Chem., 1991, 56, 2611) The diketopiperazine 14 was obtained in 76% yield upon deprotection of 13 and ammonia-DMAP-induced cyclization.

An intramolecular variant of the aza-Wittig reaction (Takeuchi, H.; Hagiwara, S.; Eguchi, S., Tetrahedron, 1989, 45, 6375) was used for efficient fusion of the (3H)-quinazolin-4-one sector. Following acylation of 14 with o-azidobenzoyl chloride, the resultant 15 reacted with tributylphosphine in benzene to afford ardeemin (2) in 56% yield from 14. Finally, acylation of 2 provided 5-N-acetylardeemin (3) in 11% overall yield for the total synthesis. The 5-N-acetylardeemin so provided was identical in all respects with an authentic sample of the natural material.

The core structure of the three reverse-prenylated hexahydropyrroloindole alkaloids was assembled rapidly and stereoselectively (through thermodynamic control) from a suitably presented tryptophan in two steps. The value of this approach was demonstrated by concise and efficient syntheses of 1, 2, and 3.

Gypsetin

The present invention also provides new analogues of gypsetin, as well as new compositions, methods of preparation of gypsetin and methods of pharmaceutical administration to inhibit the growth of MDR cells. However, the known use of gypsetin is to control cholesterol levels in vivo. The gypsetin analogues provided herein are useful for treating subjects with elevated cholesterol levels.

The regulation of cholesterol metabolism in humans is a major focus of drug development. Correlation between excess cholesterol and susceptibility to coronary heart disease is now generally accepted. (Brown, M. S.; Goldstein, J. L., Angew. Chem., Int. Ed. Engl., 1986, 25, 583) Interference either with the dietary absorption of cholesterol-containing foodstuffs or with the de novo biosynthesis of cholesterol has been used to lower plasma cholesterol content. Early strategies for containing hypercholesterolemia utilized the bile acid sequestrant cholestyramine resin. (Lipid Research Clinics Procram, J. Am. Med. Assoc., 1984, 251, 351) However, the difficulties associated with this form of medication prompted a search for other approaches. A milestone the contemporary management of cholesterol levels arose from the discovery of lovastatin, a powerful inhibitor of HMG-CoA reductase. (Grundy, S. M., Cholesterol and Atherosclerois, Diagnosis and Treatment; Tower Medical: New York, 1990; p 4; Grundy, S. M., New Engl. J. Med., 1988, 319, 24) This enzyme mediates the rate-limiting enzymatic step in cholesterol biosynthesis. Agents based on the concept of HMG-CoA inhibition have proven to be effective in lowering both LDL and total cholesterol levels in primary hypercholestemic patients. Inhibitors of squalene synthase such as the zaragozic acids have also been been identified as possible therapeutic agents but have not yet found clinical application. (Abe, I.; Tomesch, J. C.; Wattanasin, S.; Prestwich, G. D., Nat. Prod. Rep., 1994, 11, 279.)

Progression from abnormally high cholesterol levels to myocardial infarction presumably begins with the accumulation of intracellular esterified cholesterol in macrophages. This is followed by subsequent foam cell formation and, ultimately, by the appearance of atherosclerotic plaques in arteries. (Sliskovic, D. R.; Whige, A. D., Trends Pharama-

*col. Sci.,* 1991, 12, 194.) The enzyme acyl CoA:cholesterol acyltransferase (ACAT) nas been identified as the rate-limiting enzyme in the absorption of cholesterol. Thus, the inhibition of ACAT has received much attention due to its potential in moderating the effect of elevated cholesterol levels. (Sliskovic, D. R.; White, A. D., *Trends Pharmacol. Sci.,* 1991, 12, 194; Kumura, T.; Takase, Y.; Hayashi, K.; Tanaka, H.; Ohtsuka, I.; Takao, S.; Kogushi, M.; Yamada, T.; Fujimori, T.; Saitou, I.; Akasaka, K., *J. Med. Chem.,* 1993, 36, 1630.)

Gypsetin (21), recently isolated from *Nannizzia gypsea* var. incurvata IFO 9228, was found to be a comz-et-t—.e inhibitor of ACAT with respect to oleoyl-CoA with a $K_i$ value of 5.5 µM. Inhibition of cholesterol ester formation in cultured macrophages with an $IC_{50}$ of 0.65 µM was observed. (Shinohara, C.; Hasumi, K.; Takei, Y.; Endo, A., *J. Antibiot.,* 1994, 47, 163; Nuber, B.; Hansske, F.; Shinohara, C.; Miura, S.; Hasumi, K.; Endo, A., *J. Antibiot.,* 1994, 47, 168.)

Figure 7:
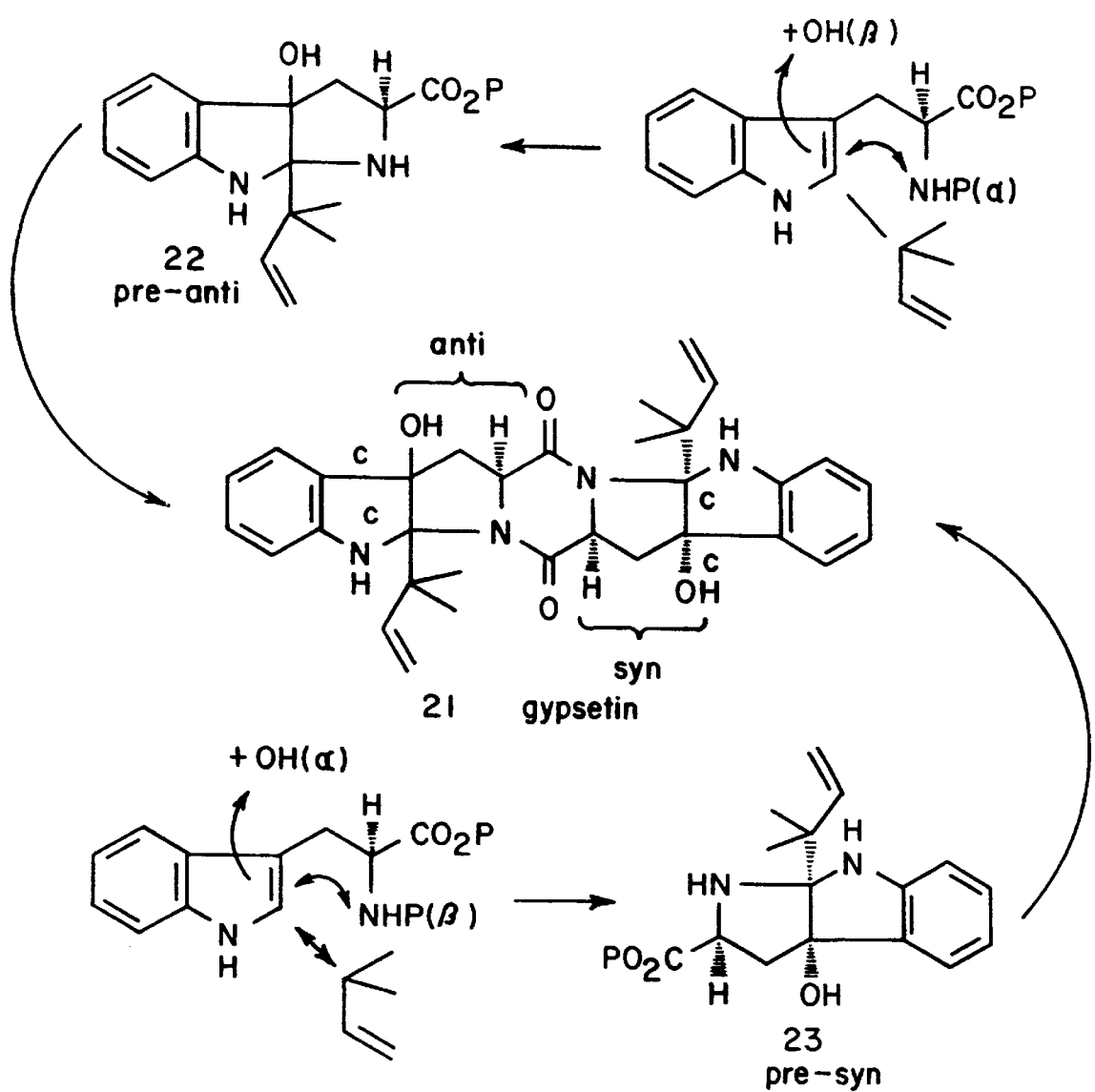
FIG. 7 illustrates a synthetic strategy for preparing gypsetin.

An important structural aspect of gypsetin is the diketopiperazine moiety which is formally composed of two hypothetical amino acids 22 and 23, differing only in the relationship of the cis-fused [2,3-b]hexahydropyrroloindole chirality at $C_{3a}$ and $C_{8a}$ to the S-configured amino acid center ($C_2$) (FIG. 7). For the sake of convenience, 22 is referred to as the "pre-anti" system and 23 as the "pre-syn" moiety, anticipating the backbone relationship of the full heptacyclic ensemble of gypsetin itself. Constructs 22 and 23 share an obvious "L-tryptophan connection" provided that methodology could be developed for the introduction of a 1,1-dimethlyallyl (reverse prenyl) function at $C_2$. In addition, cyclization of $N_b$ of the amino acid side chain to $C_2$ of the indole and hydroxylation at $C_3$ of the indole through the agency of formal $^+$OH would be necessary.

Provided hereinabove, in connection with the synthesis of N-acetylardeemin, is a method for the introduction of such a reverse prenyl group into the $C_{3a}$ of a prebuilt [2,3-b] hexahydropyrroloindole moiety. (Marsden, S. P.; Depew, K. M.; Danishefsky S. J., *J. Am. Chem. Soc.,* 1994, 116, 11143.) This transformation was accomplished via a $C_{3a}$ phenylseieno precursor. The present invention provides a method of introducing the reverse prenyl groups at $C_{5a}$ and $C_{13a}$ and the hydroxyl functions at $C_{8a}$ and $C_{16a}$ of a gypsetin (21), thus enabling a concise total synthesis of gypsetin and analogues thereof.

Figure 8:
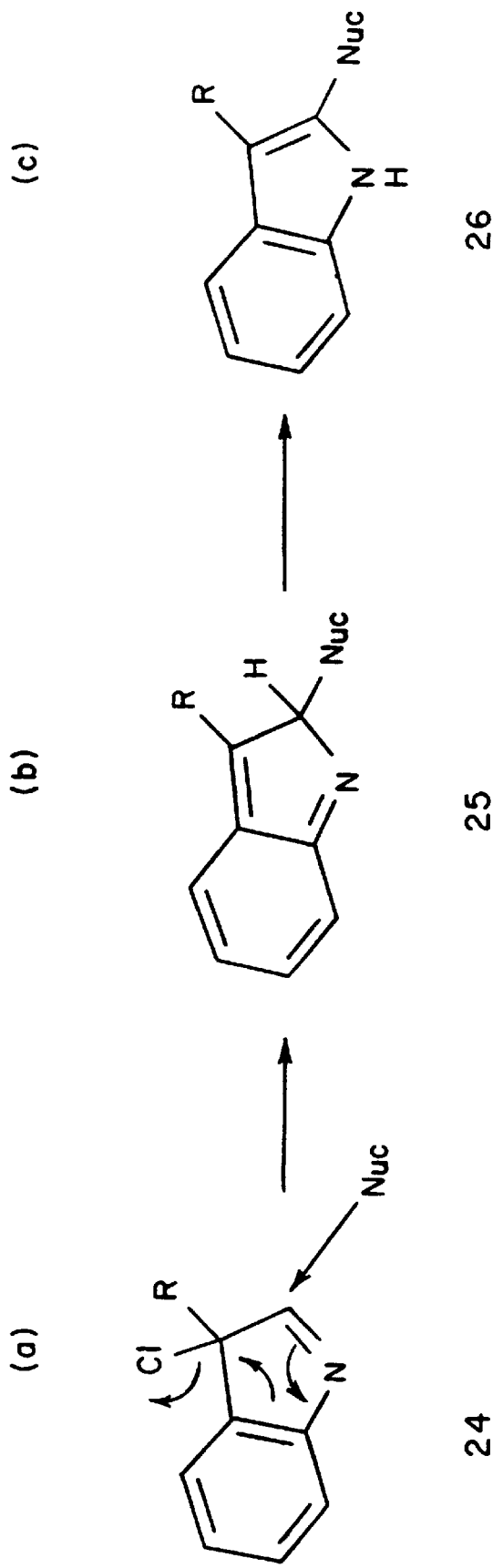
FIG. 8 shows the preparation of 2,3-disubstituted indoles 26 by addition of nucleophiles to chloroindolenines.

The present invention provides a simple method to introduce the "reverse prenyl" function at $C_2$ of the indole in the presence of a suitably protected amino acid side chain. The oxidative conversion of 2,3-disubstituted indoles to chloroindolenines and the use of such chloroindolenines for functionalization of the carbon benzylic to $C_2$ was known. (Godtfredsen, W. O.; Vangedal S., *Acta Chem. Scand.,* 1956, 10, 1414; Buchi, G.; Manning, R. E., *J. Am. Chem. Soc.,* 1966, 88, 2532; Owellen, R. J., *J. Org. Chem.,* 1974, 39, 69; Kutney, J. P.; Beck, J.; Bylsma, F.; Cook, J.; Cretney, W. J.; Fuji, K.; Imhof, R.; Treasurywala, A. M., *Helv. Chim. Acta,* 1975, 58, 1690; Kuehne, M. E.; Hafter, R., *J. Org. Chem.,* 1978, 43, 3702 and references therein) A key issue was whether an intermediate such as 24 would have transient viability even if $C_2$ were unsubstituted. (For the only previously disclosed example of a carbon-based nucleophilic addition to a $C_2$-unsubstituted chloroindolenine, see: Parsons, R. L.; Berk, J. D.; Kuehne, M. E., *J. Org. Chem.,* 1993, 58, 7482.) The mechanism for the conversion 24 to 25 could involve a two-step sequence (i.e., addition to the imine and loss of HCl). Compound 24 suffers nucleophilic attack at $C_2$ leading to 25 and thereafter tautomerizes to 26 (FIG. 8). Application of this protocol allows for a rapid preparation of 2,3-disubstituted indoles.

Figure 9:
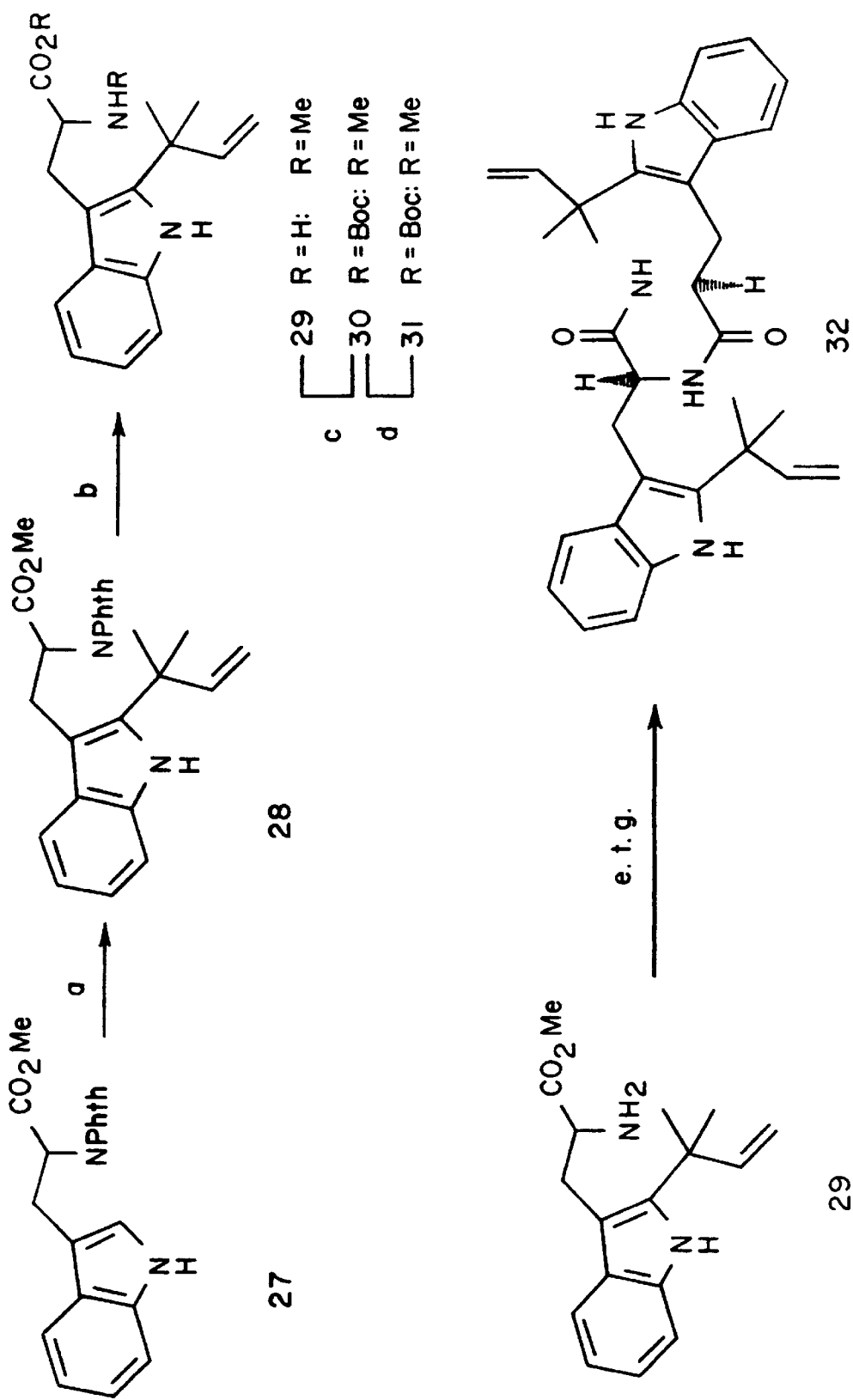
FIG. 9 shows the preparation of intermediate 32.

The synthesis of gypsetin began with N-phthaloyltryptophan methyl ester (27; prepared from L-tryptophan methyl ester by modification of a known method: Bodansky, M.; Bodansky, A., *The Practice of Peptide Synthesis*; Springer-Verlag: Berlin, 1984, p 10; FIG. 9), which was converted in 95% yield to 28, following the approach described above, with prenyl-9-BBN as the nucleophile. (Kramer, G. W.; Brown, H. C., *J. Organomet. Chem.,* 1977, 132, 9. The reaction of prenyl-9-BBN on the chloroindolenine (24) does not require the use of a catalyst; with other nucleophiles, catalysis is needed.; Hydrazinolysis led to the $C_2$-reverse prenylated tryptophan derivative 29.

In addition, oxidative cyclization of a pre-constructed diketopiperazine (32), stereochemically uncommitted with respect to the syn-anti issue, would be advantageous in the absence of diastereofacial control in the conversion of a system such as 30 to 22 or 23. Therefore, compound 29 was converted to 31 by first protecting the amine function with a BOC group and saponifying with LiOH/THF/MeOH/$H_2O$. Coupling of 29 and 31 led, as shown, to diketopiperazine 32.

Figure 10:
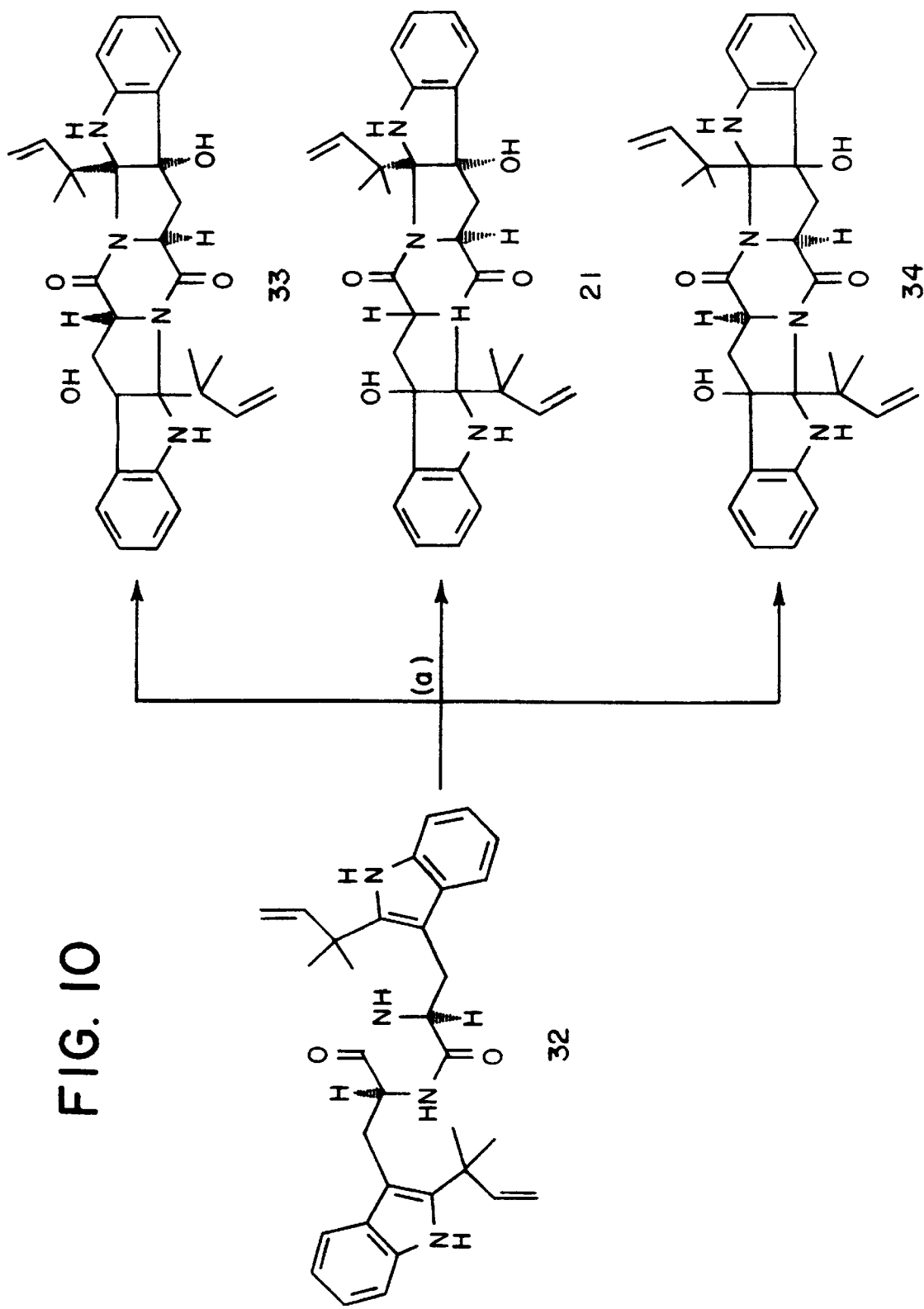
FIG. 10 shows the preparation of gypsetin and gypsetin diastereoisomers.
Figure 11:
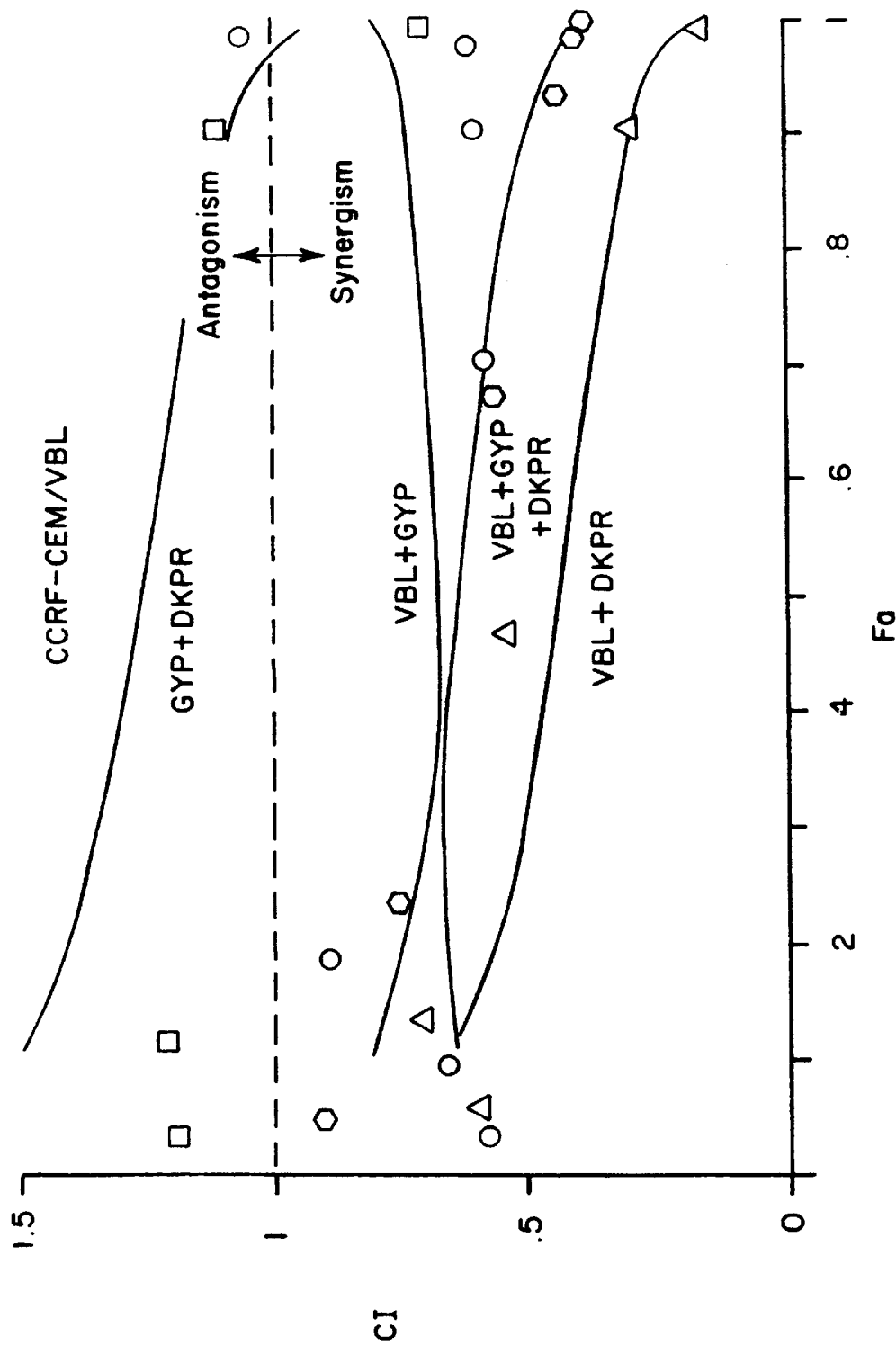
FIG. 11 shows a plot of combination index (CI) as a function of fractional effect ($F_a$) for two- or three-drug combinations of diketopiperazine 14, gypsetin and vinblastine on vinblastine-resistant CCRF-CEM leukemia cells.
Figure 12:
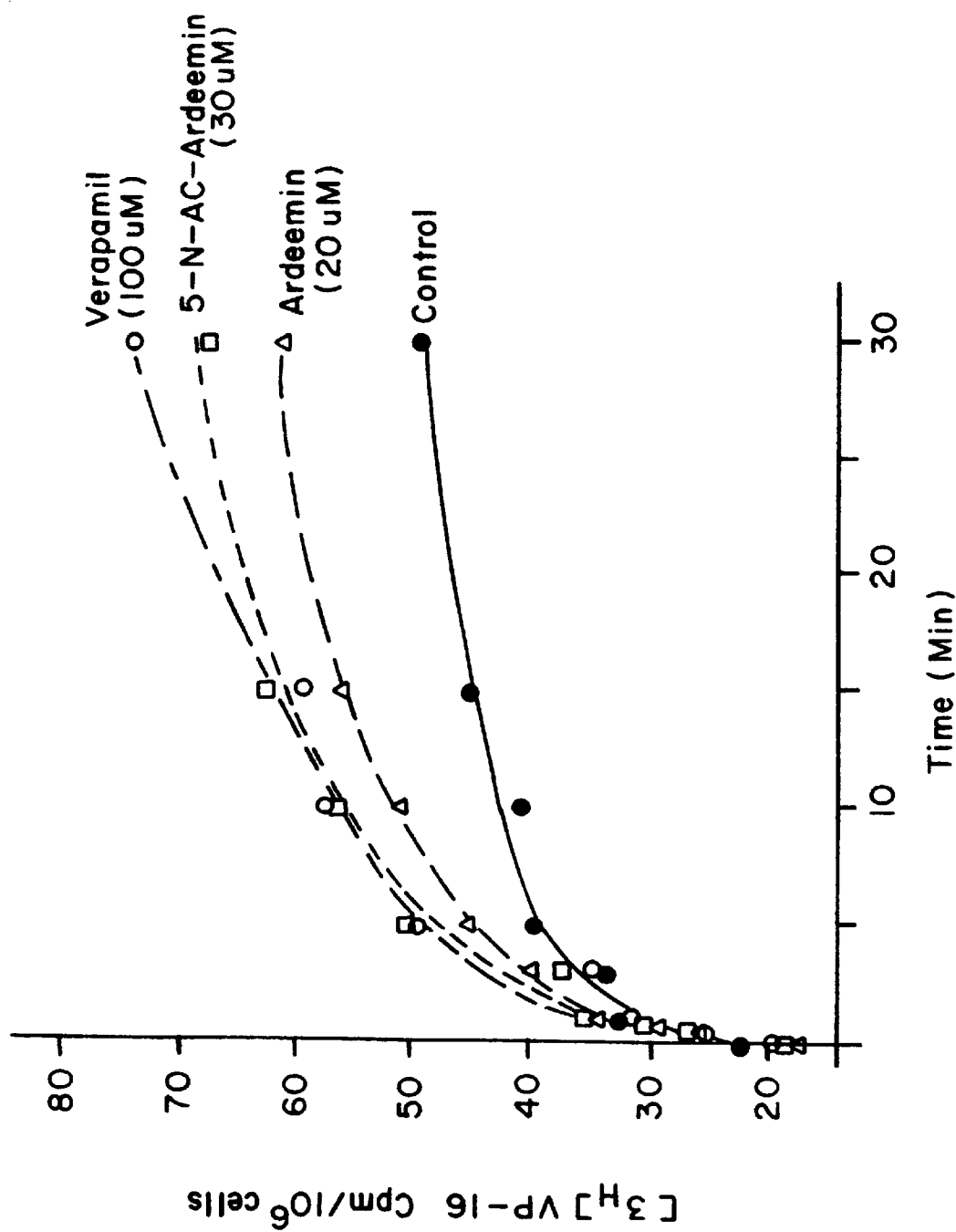
FIG. 12 shows increased intracellular accumulation of [$^3$H]VP-16 due to administration of ardeemin, N-acetylardeemin and verapamil in CCRF-CEM leukemia cells (influx assay); single drug case.
Figure 13:
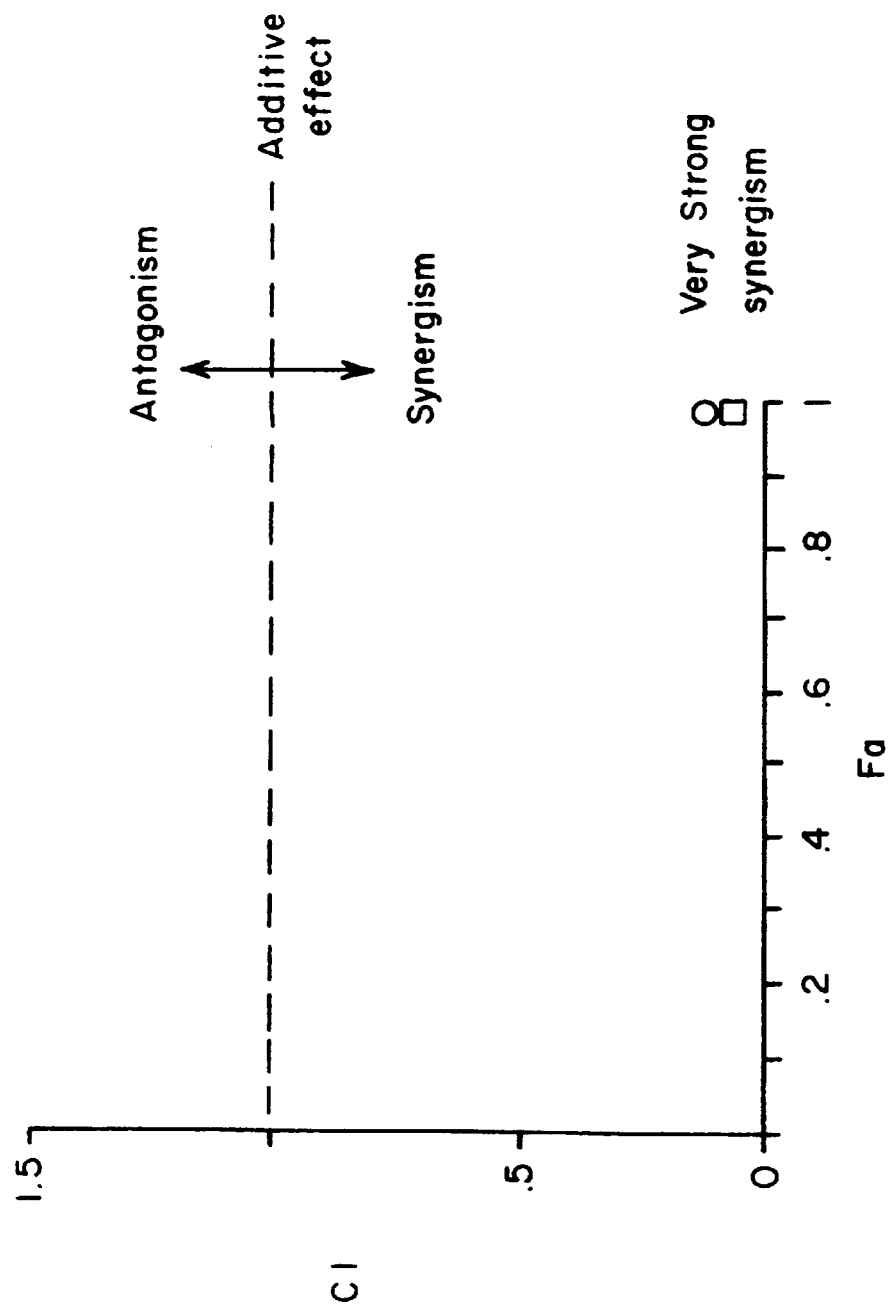
FIG. 13 shows a plot of combination index (CI) as a function of fractional effect ($F_a$) for two-drug combinations of 5-N-Ac-ardeemin and vinblastine on vinblastine-resistant CCRF-CEM/VBL leukemia cells; open circle, 1:40; open square, 1:100, open triangle, 1:200; mutually exclusive case.
Figure 14:
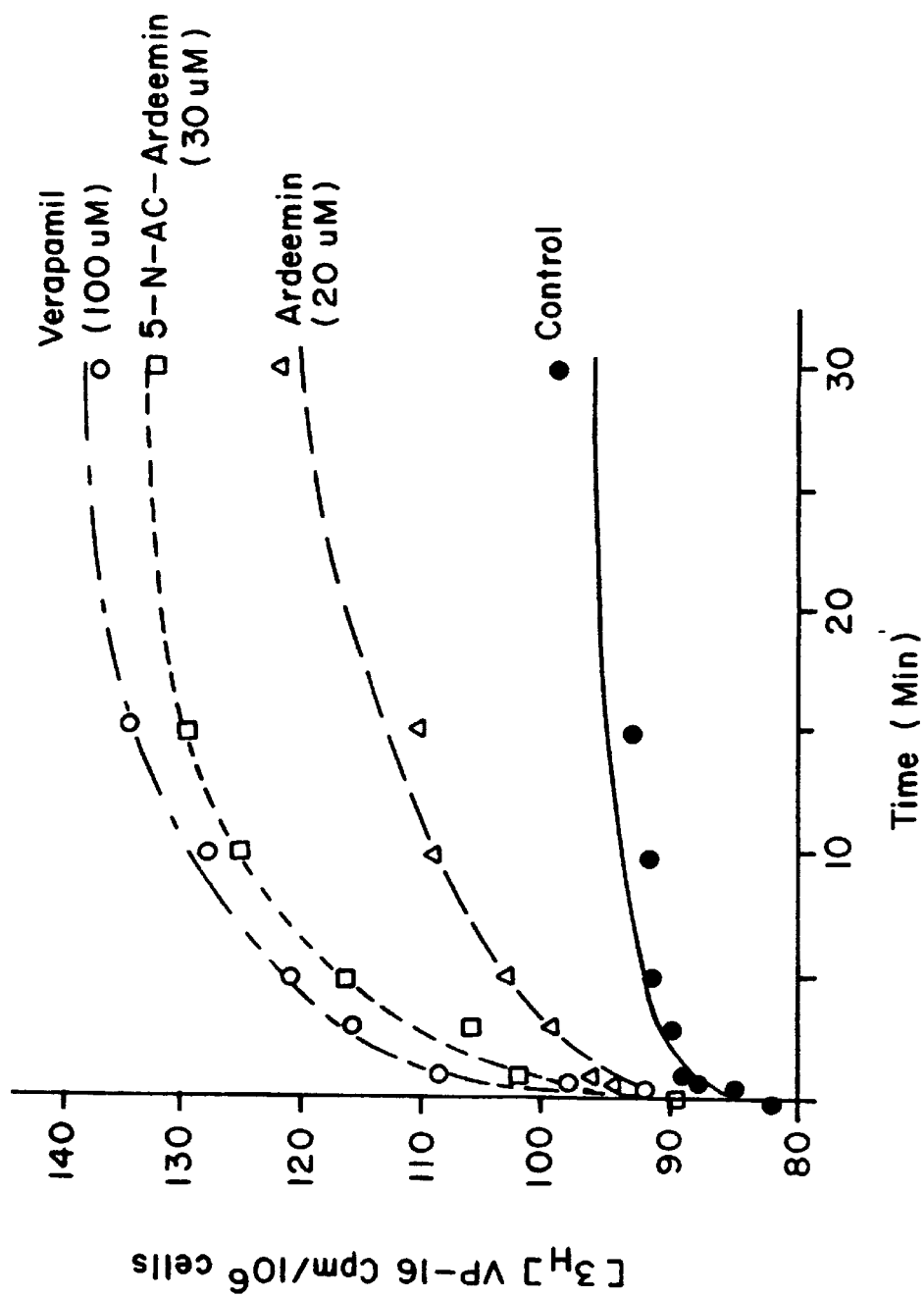
FIG. 14 shows increased intracellular accumulation of [$^3$H]VP-16 due to administration of ardeemin, N-acetylardeemin and verapamil in CCRF-CEM leukemia cells (efflux assay); pre-loaded drug.
Figure 15A:
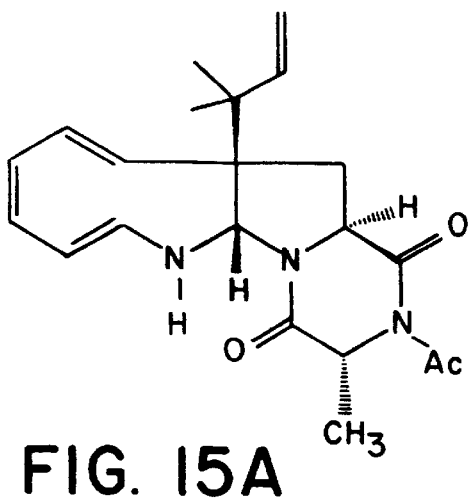
FIGS. 15A–15E shows structures for diketopiperazine analogues of N-acetylardeemin: 15(A), imide acetate diketopiperazine; 15(B), diketopiperazine; 15(C), imide-BOC diketopiperazine; 15(D), imide diacetate diketopiperazine; 15(E), N-acetyldiketopiperazine.
Figure 15B:
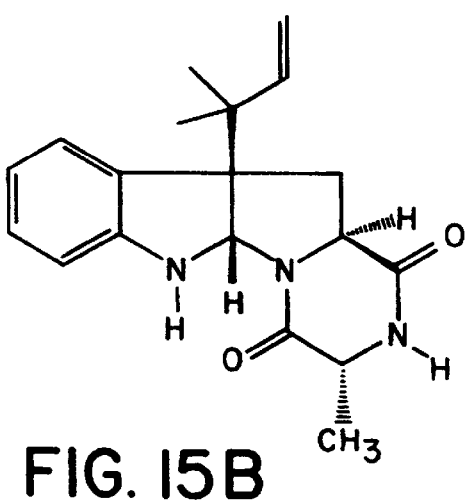
Figure 15C:
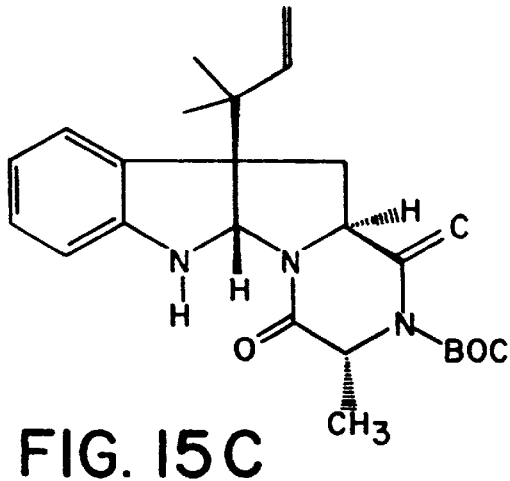
Figure 15D:
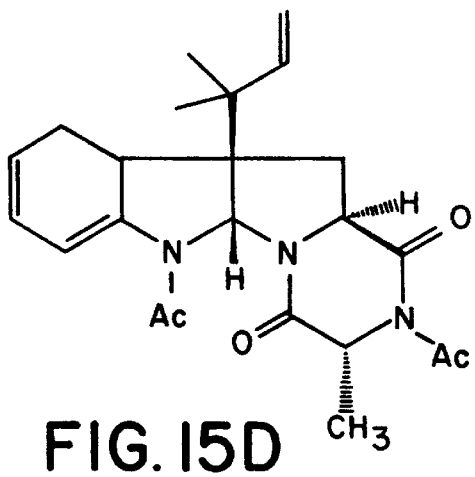
Figure 15E:
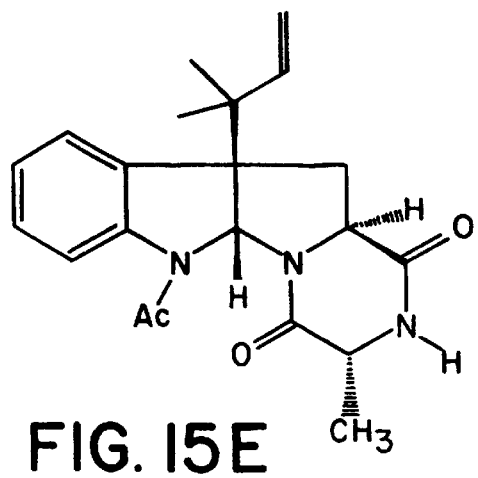
Figure 16A:
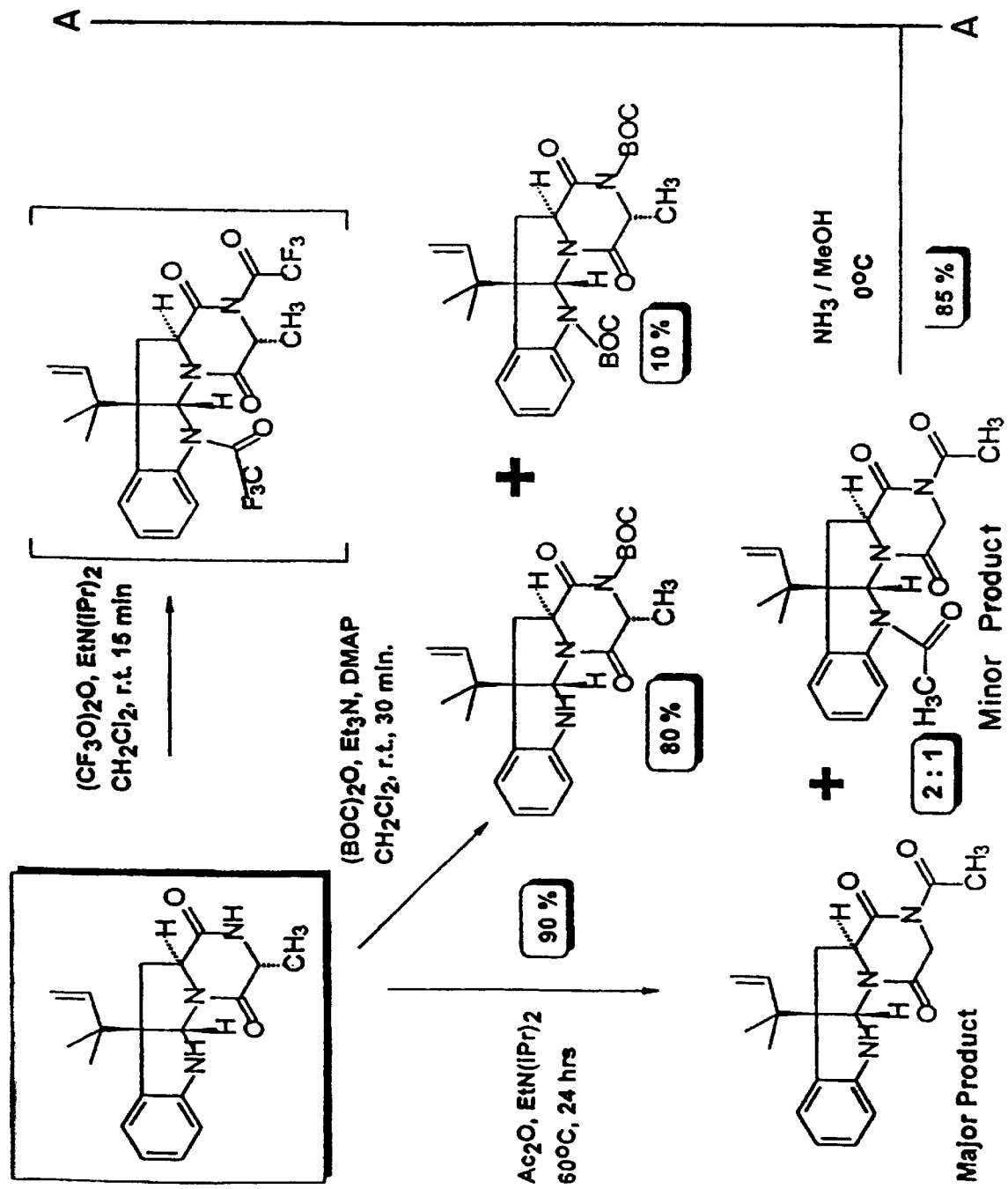
FIGS. 16A–16B illustrates preparative routes providing diketopiperazine analogues of N-acetyl-8-desmethyl-ardeemin: imide acetate diketopiperazine; N-acetyl imideacetate diketopiperazine; 5N-acetyl diketopiperazine; 5N-trifluoroacetyl diketopiperazine; 5N-trifluoroacetyl imideacetate diketopiperazine; 5N-BOC imide-BOC diketopiperazine; imide-BOC diketopiperazine.
Figure 16B:
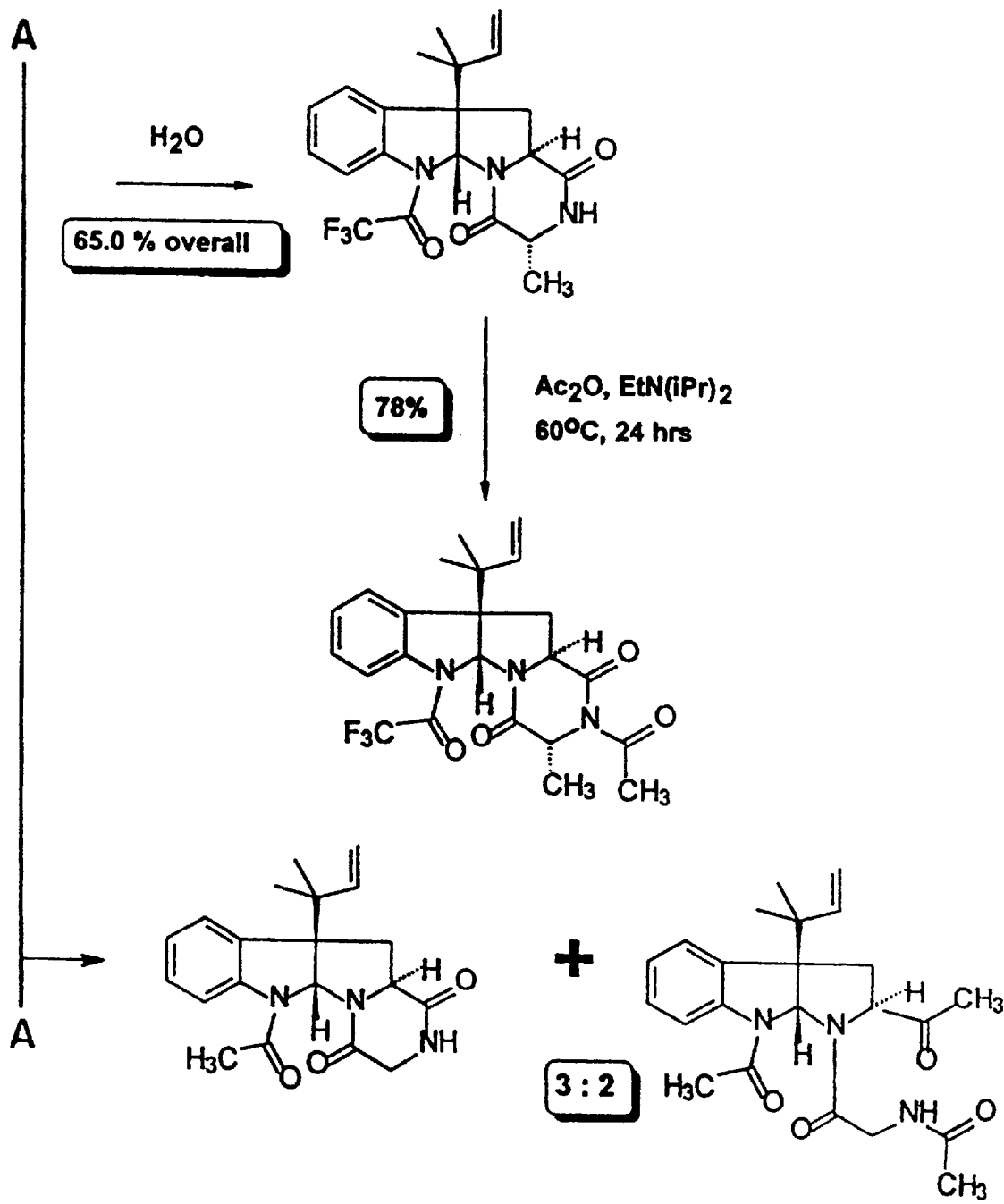
Figure 17A:
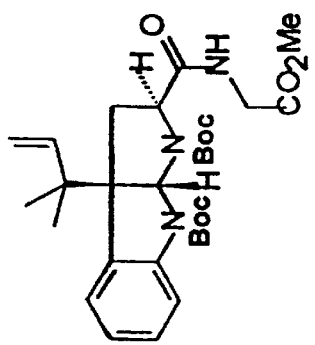
FIGS. 17A–17B shows a synthetic scheme for the preparation of N-Acetyl-8-desmethyl-ardeemin.
Figure 17A:
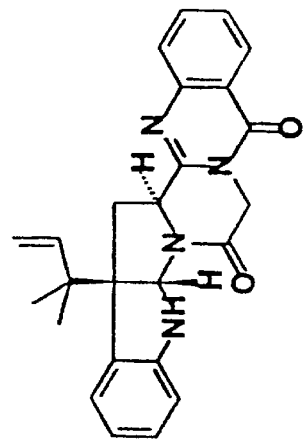
Figure 17A:
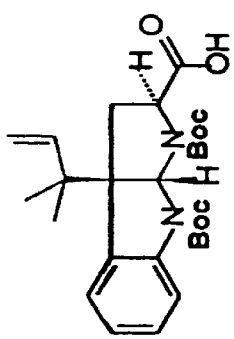
Figure 17A:
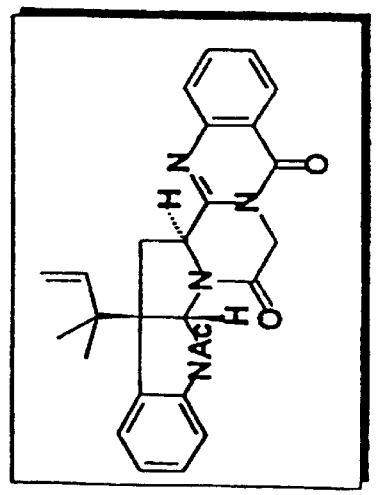
Figure 17B:
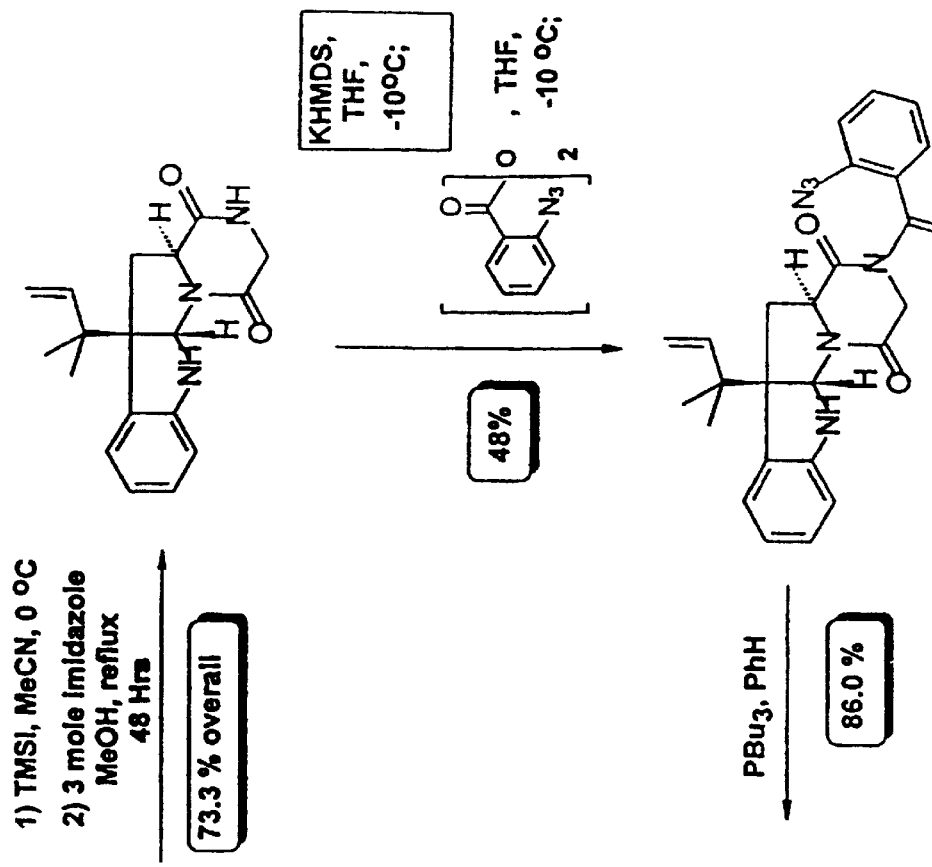
Figure 18:
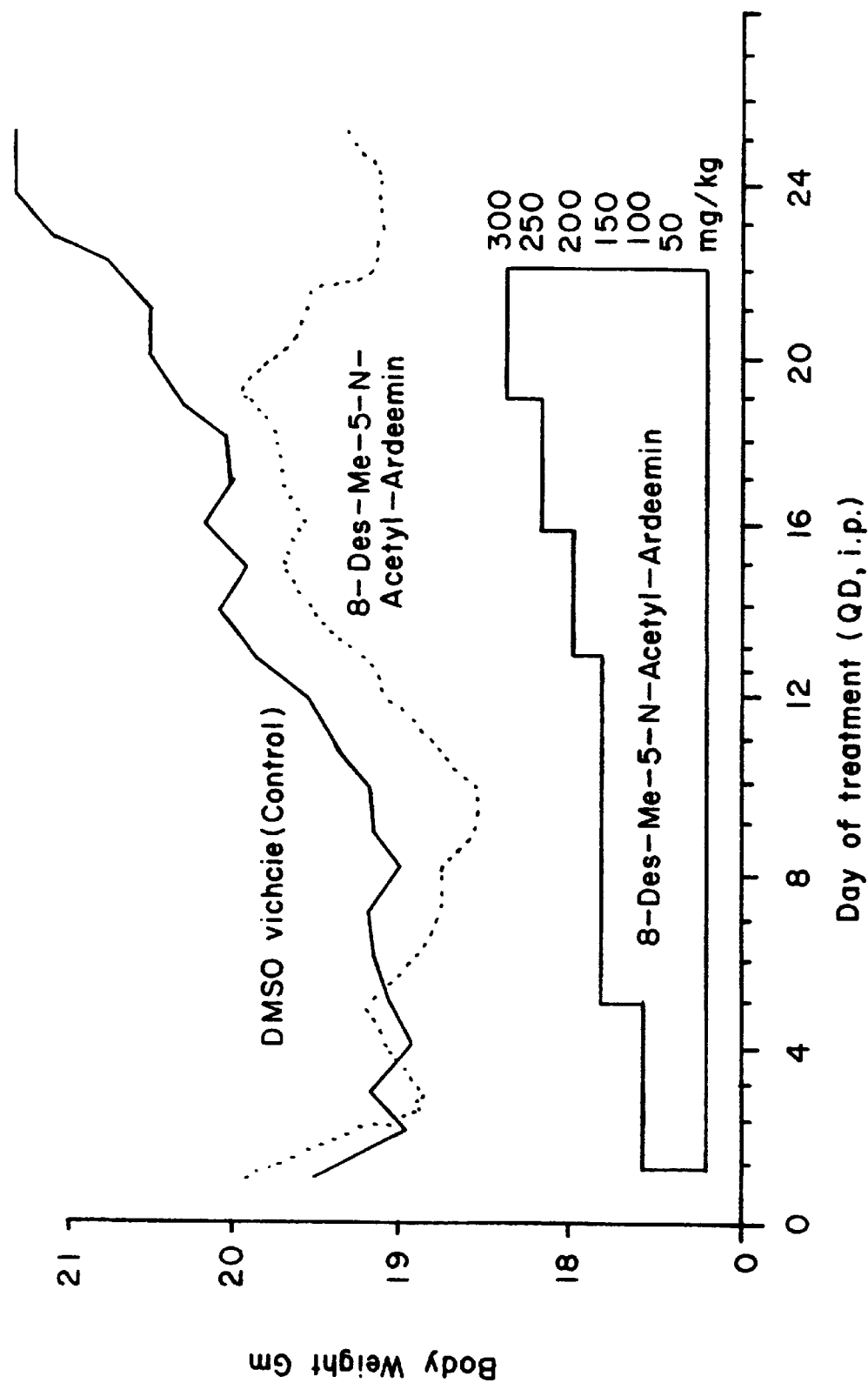
FIG. 18 shows the toxicity of N-acetyl-desmethyl-ardeemin in BDF mice.
Figure 19B:
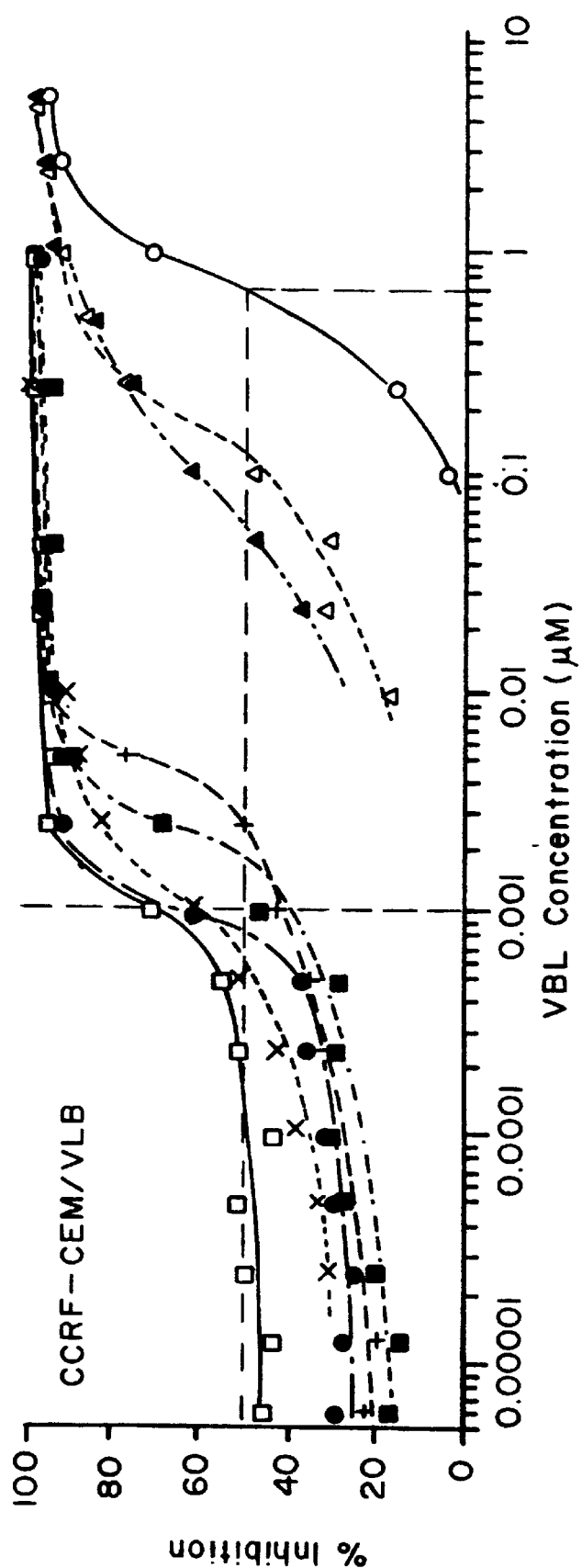
Figure 20:
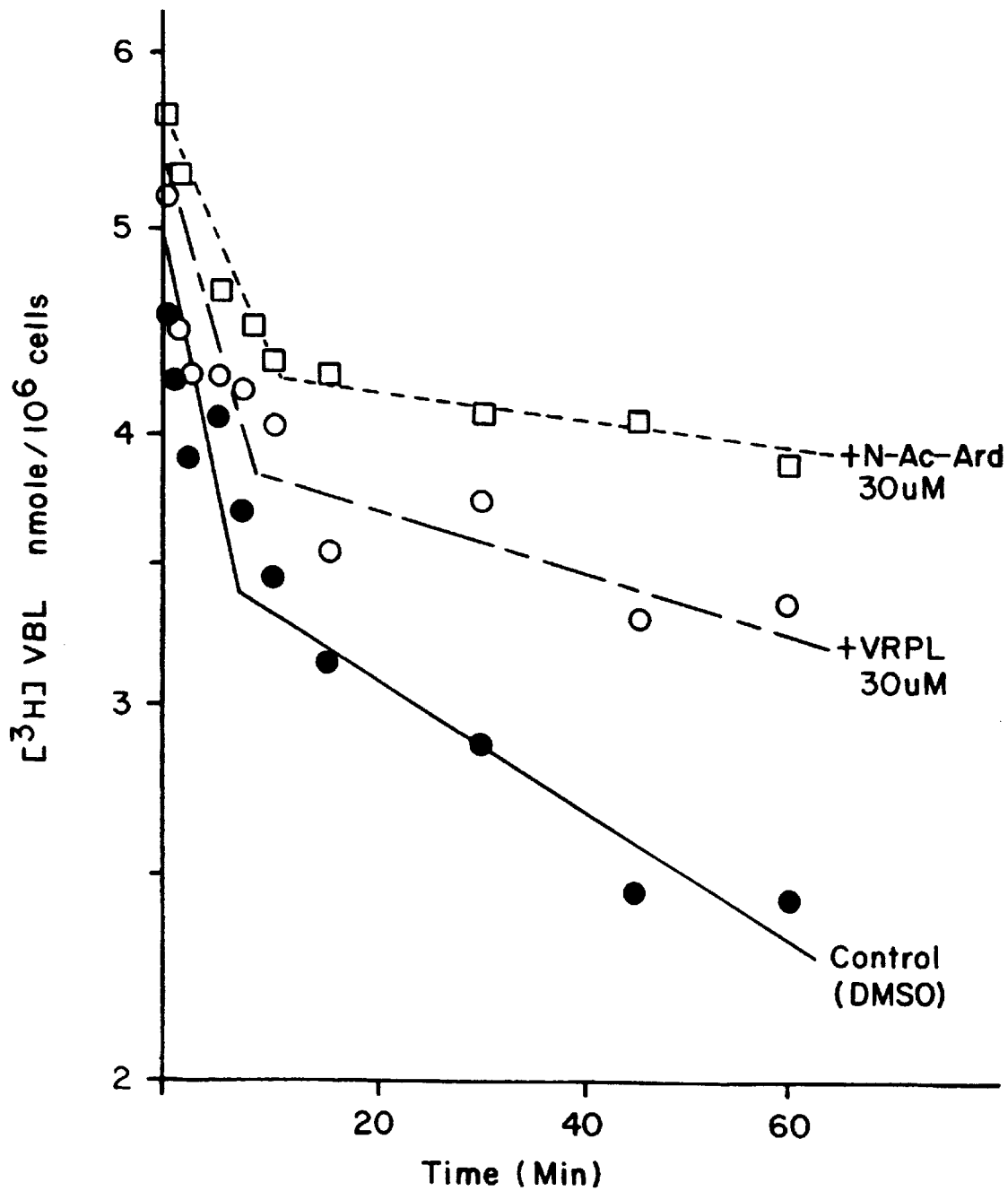
FIG. 20 illustrates efflux kinetics for CCRF-CEM/VBL-100 cells preloaded with tritiated vinblastine for 30 min at 37° C. Cells were washed twice at 4° C., MDR agent added at 0 min, and incubated at 37° C.

A one-step conversion of diketopiperazine 32 to gypsetin (21) was attempted. A stereochemically random oxidative cyclization process would benefit from the concept that the hypothetical ratio of gypsetin to "syn"—"syn" product 33 and "anti"—"anti" product 34 would be 2:1:1. Many oxidants have been surveyed, but only one has proven to be successful. Thus, reaction of 32 with 4 equiv of dimethyldioxirane afforded a 40% isolated yield of fully synthetic gypsetin (21) along with double syn product 33 (ca. 18%) and double anti product 34 (ca. 20%) (FIG. 10). (For the reaction of Na-acylated indoles with dimethyldioxirane, see Zhang, X., and Foote, C. S., *J. Am. Chem. Soc.,* 1993, 115, 8867; Adam, W., Ahreweiler, M., Peters, K., and Schmiedeskamp, B., *J. Org. Chem.,* 1994, 59, 2733.) The spectral properties ($^1$H NMR, $^{13}$C NMR, MS, and IR) of synthetic gypsetin (21) were consistent with those of natural material. In addition, the chromatographic properties were identical, and the mel-ing point (159° C.) was in accord with that reported for naturally derived material. The optical rotation of synthetic gypsetin was $[\alpha]^{24}_D$=−113.4° (c 0.20, $CHCl_3$) which was in good agreement with that of natural gypsetin, $[\alpha]^{24}_D$=−116.9° (c 0.14, $CHCl_3$)

Accordingly, the total synthesis of gypsetin has been achieved. This synthesis can be conducted in as few as four steps from N-phthaloyltryptophan methyl ester (27), and is concise given the apparent complexity. (Diketopiperazine 32 can be prepared directly, albeit in 3506 yield, by heating tryptophan methyl ester (29) at 140° C. for 3 h, thereby saving four steps in the synthetic sequence described above.) Thus, chemistry developed here also serves to enhance methods for the synthesis of other complex indoles. (There are relatively few direct methods for the preparation of 2,3-disubstituted indoles. For some methods, see Saulnier, M. G.; Gribble, G. W., *J. Org. Chem.,* 1982, 47, 2810; Fukuyama, T. F.; Chen, X.; Peng, G., *J. Am. Chem. Soc.,* 1994, 116, 3127.)

TABLE 7

Cytotoxicity of Gypsetin Isomers and 5-N-Acetylardeemin in Hamster Lung Cells Sensitive and Resistant to Actinomycin D

| Compound growth | IC$_{50}$ for inhibiting cell ($\mu$M) | |
|---|---|---|
| | DC-3F | DC-3F/SDII |
| Gypsetin | 3.78 | 2.25 |
| Gypsetin, cis/cis | 36.5 | 15.6 |
| Gypsetin, trans/trans | 13.8 | 11.3 |
| N-Acetylardeemin | 3.74 | 1.07 |
| | 5.06 | 1.59 |
| Adriamycin | 0.03 | 0.38 |

TABLE 8

Survival Time Evaluation for BDF Mice Bearing P388/0[a]

| CAGE | DOSE (mg/Kg)[b] | | AWC (g) | | | | SURVIVAL TIME[e] | | | | | | MST[c] | % ILS[d] |
|---|---|---|---|---|---|---|---|---|---|---|---|---|---|---|
| | DRUG A | DRUG B | DAY 0 | DAY 4 | DAY 6 | DAY 8 | DAY 11 | No. 1 | No. 2 | No. 3 | No. 4 | No. 5 | No. 6 | MST | % ILS |
| 1 | | | 19.0 | +0.2 | +2.5 | +4.2 | | 6.0 | 7.0 | 7.5 | 7.5 | 8.25 | 8.25 | 7.42 | 0 |
| 2 | | 3.33 | 19.4 | +0.9 | +3.3 | | | 6.0 | 7.0 | 8.0 | 8.0 | | | 7.25 | -2 |
| 3 | | 10 | 19.0 | +1.7 | +4.8 | | | 60. | 6.5 | 7.5 | | | | 6.67 | -10 |
| 4 | | 30 | 19.0 | +1.6 | +3.8 | | | 6.0 | 6.5 | | | | | 6.25 | -16 |
| 5 | 0.333 | | 19.5 | -0.1 | +0.5 | +1.4 | +3.5 | 12.25 | 13.0 | 14.25 | 15.5 | | | 13.75 | 85 |
| 6 | 1.0 | | 18.3 | -0.6 | -0.3 | +0.5 | +1.8 | 14.25 | 15.5 | 18.0 | 20.25 | | | 17.0 | 129 |
| 7 | 3.0 | | 18.5 | -1.2 | -1.0 | -0.8 | 0 | 16.0 | 17.25 | 19.25 | 20.25 | | | 18.19 | 145 |
| 8 | 0.333 | 3.33 | 19.0 | -2.0 | -1.0 | +0.3 | +2.0 | 14.0 | 15.0 | 15.5 | 17.25 | | | 15.43 | 108 |
| 9 | 1.0 | 10 | 19.0 | -2.0 | -1.1 | 0 | +1.7 | 16.0 | 16.0 | 18.0 | | | | 16.67 | 125 |
| 10 | 3.0 | 30 | 20.0 | -2.7 | -2.5 | -2.0 | -1.8 | 18.0 | 21.0 | | | | | 19.5 | 163 |

[a]Male BDF mice were inoculated with p388/0, 10E6 cells/mouse, I.P. at Day 0, treated by adriamycin and 5-N-acetylardeemin, starting Day 1 through Day 4, I.P. daily.
[b]Drug A = adriamycin; Drug B = 5-N-acetylardeemin.
[c]MST = mean survival time.
[d]% ILS = percent increase in lifespan.
[e]Survival times were recorded based on the time of death with the following decimal values: 8AM (0.0), 1PM (0.25), 5PM (0.5).

TABLE 9

Survival Time Evaluation for BDF Mice Bearing P388/DX[a]

| CAGE | DOSE (mg/Kg)[b] | | AWC (g) | | | | SURVIVAL TIME[e] | | | | | | MST[c] | % ILS[d] |
|---|---|---|---|---|---|---|---|---|---|---|---|---|---|---|
| | DRUG A | DRUG B | DAY 0 | DAY 4 | DAY 6 | DAY 8 | DAY 11 | No. 1 | No. 2 | No. 3 | No. 4 | No. 5 | No. 6 | MST | % ILS |
| 11 | | | 19.0 | -1.5 | +3.8 | +2.5 | | 6.0 | 7.0 | 7.0 | 7.0 | 8.25 | 8.25 | 7.25 | 0 |
| 12 | | 3.33 | 19.4 | +1.0 | +1.3 | +1.7 | | 6.5 | 7.0 | 8.0 | 9.0 | | | 7.63 | 5 |
| 13 | | 10 | 18.8 | +2.2 | +3.4 | | | 7.0 | 7.25 | 8.0 | | | | 7.42 | 2 |
| 14 | | 30 | 19.1 | +1.2 | +1.4 | | | 6.5 | 7.0 | | | | | 6.75 | -7 |
| 15 | 0.333 | | 19.5 | +1.0 | +3.8 | +5.2 | | 8.0 | 8.5 | 9.5 | 10.0 | | | 9.0 | 24 |
| 16 | 1.0 | | 19.3 | 0 | +1.2 | +3.7 | | 9.0 | 10.0 | 10.25 | 10.5 | | | 9.75 | 37 |
| 17 | 3.0 | | 20.0 | -0.5 | +1.0 | +1.7 | +4.5 | 10.0 | 10.0 | 11.5 | 12.25 | | | 10.75 | 48 |
| 18 | 0.333 | 3.33 | 19.0 | -1.4 | +1.0 | +3.1 | +6.0 | 9.0 | 10.0 | 11.5 | 12.25 | | | 10.69 | 47 |
| 19 | 1.0 | 10 | 18.7 | -0.7 | +1.6 | +3.6 | +4.9 | 9.25 | 11.5 | 13.0 | | | | 11.25 | 55 |
| 20 | 3.0 | 30 | 18.5 | +0.5 | +1.0 | +1.0 | +2.8 | 12.25 | 14.0 | | | | | 13.13 | 81 |

[a]Male BDF mice were inoculated with p388/0, 10E6 cells/mouse, I.P. at Day 0, treated by adriamycin and 5-N-acetylardeemin, starting Day 1 through Day 4, I.P. daily.
[b]Drug A = adriamycin; Drug B = 5-N-acetylardeemin.
[c]MST = mean survival time.
[d]% ILS = percent increase in lifespan.
[e]Survival times were recorded based on the time of death with the following decimal values: 8AM (0.0), 1PM (0.25), 5PM (0.5).

What is claimed is:

1. A compound having the structure:

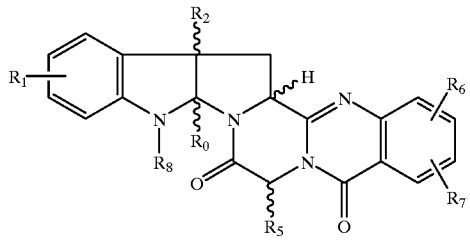

wherein $R_0$, $R_1$, $R_3$, $R_4$, $R_6$ and $R_7$ are hydrogen; wherein $R_2$ is —$CR_3R_3$—CH=$CHR_4$; wherein $R_5$ is $CH_3$; and wherein $R_8$ is —(C=O)$CH_3$.

2. A process for synthesizing an N-acylardeemin having the structure:

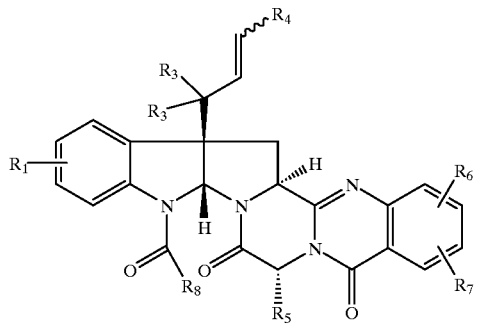

wherein $R_1$ is hydrogen or $C_1$–$C_9$ linear or branched chain alkyl; wherein $R_3$ and $R_4$ are independently hydrogen or $C_1$–$C_9$ linear or branched chain alkyl; wherein $R_5$ is hydrogen or $C_1$–$C_9$ linear or branched chain alkyl; and wherein $R_6$ and $R_7$ are independently hydrogen or $C_1$–$C_9$, linear or branched chain alkyl; and wherein $R_8$ is $C_1$–$C_9$ linear or branched chain alkyl; which comprises:

(a) (i) reacting a compound having the structure:

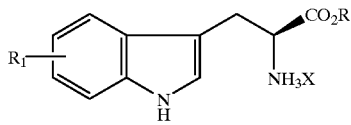

wherein X is Br, Cl,

F, I, mesylate, triflate, tosylate, perchlorate, hydrogensulfate, carbonate, bicarbonate or tetrafluoroborate; and R is $C_1$–$C_9$ linear or branched chain alkyl, phenyl, alkylphenyl, alkylphenyl, alkoxyphenyl, benzyl or alkoxybenzyl, with an acyl halide having the structure $R_0(C=O)$—Z, wherein Z is F, Cl, Br or I, or an acyl anhydride having the structure $\{R_0O(C=O)\}_2O$, wherein $R_0$ is $C_1$–$C_9$ linear or branched chain alkyl, phenyl, $C_1$–$C_9$ linear or branched chain alkylphenyl, $C_1$–$C_9$ linear or branched chain dialkylphenyl, $C_1$–$C_9$ linear or branched chain alkoxyphenyl, benzyl or 9-fluorenemethyl, to form a dicarbamate having the structure:

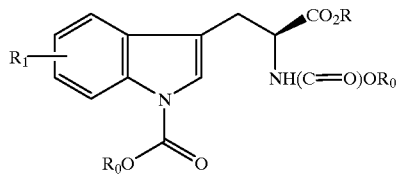

(ii) treating the dicarbamate formed in step (a)(i) with a suitable phenylselenenide reagent to form a mixture of phenylselenide dicarbamates having the structures:

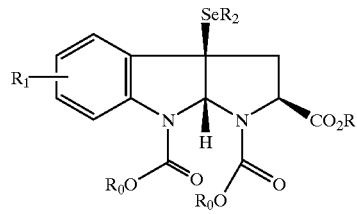

and

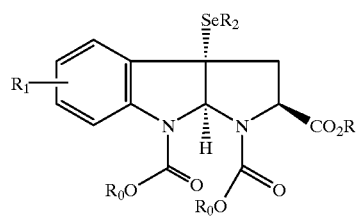

wherein $R_2$ is phenyl, $C_1$–$C_9$ linear or branched chain alkylphenyl, $C_1$–$C_9$ linear or branched chain alkylphenyl or $C_1$–$C_9$ linear or branched chain trialkylphenyl; and (iii) cross-coupling the mixture of phenyl-selenide dicarbamates formed in step (a)(ii) with (1) an organostannane having the structure $R_3R_3C=CHCHR_4SnR'R''R'''$ wherein $R_3$ and $R_4$ are independently hydrogen, $C_1$–$C_9$ linear or branched chain alkyl; and wherein R', R" and R''' are independently a $C_1$–$C_9$ linear or branched chain alkyl, phenyl, $C_1$–$C_9$ linear or branched chain alkylphenyl, $C_1$–$C_9$ linear or branched chain alkylphenyl, $C_1$–$C_9$ linear or branched chain alkoxyphenyl or benzyl, or (2) a Grignard reagent having the structure $Z_0MgR_3R_3C$—CH=$CHR_4$ and an organometallic catalyst having the structure $NiQ_2(PR^{iv}_3)_2$ where Q and $Z_0$ are independently F, Cl, Br or I and $R^{iv}$ is $C_1$–$C_9$ linear or branched chain alkyl, phenyl, $C_1$–$C_9$ linear or branched chain alkylphenyl, $C_1$–$C_9$ linear or branched chain dialkylphenyl, $C_1$–$C_9$ linear or branched chain alkoxyphenyl or benzyl, to form a mixture of cross-coupled dicarbamates respectively having the structure:

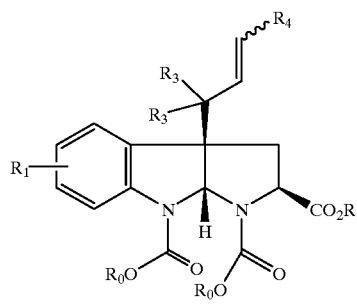

and

-continued

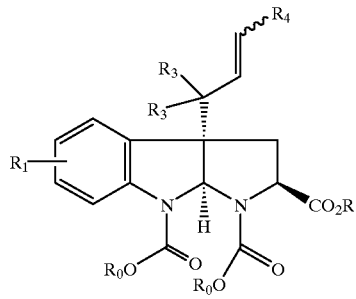

(b) (i) hydrolzying the mixture of cross-coupled dicarbamates formed in step (a)(iii) to form a mixture of dicarbamate acids;
(ii) purifying the mixture of dicarbamate acids formed in step (b)(1); and
(iii) isolating the dicarbamate acid having the structure:

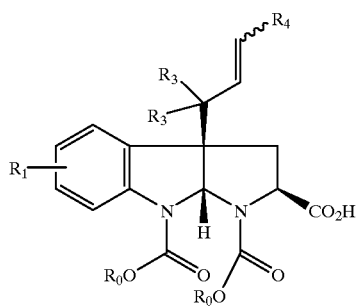

(c) coupling the dicarbamate acid with an amino acid ester having the structure:

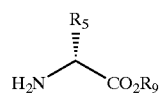

wherein wherein $R_5$ is as defined above and $R_9$ is $C_1$–$C_9$ linear or branched chain alkyl, phenyl, $C_1$–$C_9$ linear or branched chain alkylphenyl, $C_1$–$C_9$ linear or branched chain dialkylphenyl, $C_1$–$C_9$ linear or branched chain alkoxyphenyl or benzyl; to form a peptide dicarbamate having the structure:

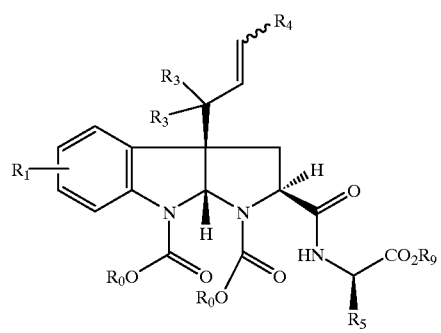

(d) (i) deprotecting and lactamizing the peptide dicarbamate, formed in step (c) to form a diketopiperazine having the structure:

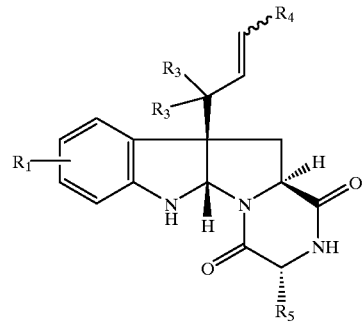

(ii) acylating the diketopiperazine formed in step (d)(i) with a compound having the structure:

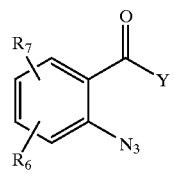

wherein Y is Cl Br, F or I, to form an N-benzoylated diketopiperazine having the structure:

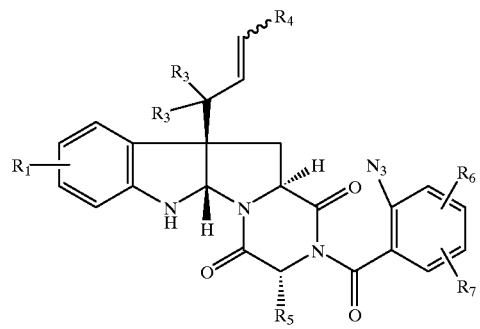

(iii) cyclizing the compound formed in step (d)(ii) to form an ardeemin having the structure:

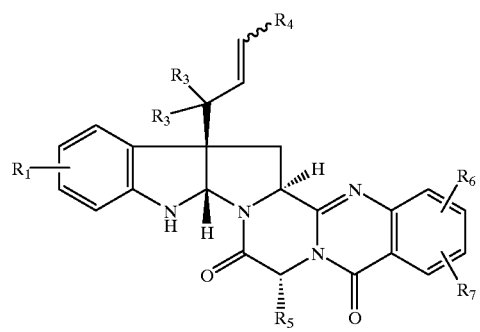

and
(iv) acylating the ardeemin formed in step (d)(iii) with (A) an acyl halide having the structure $R_8(C=O)$—Z' wherein $R_8$ is $C_1$–$C_9$ linear or branched chain alkyl, and Z' is Cl, Br, F, I, or where R is a $C_1$–$C_9$ linear or branched chain alkyl, phenyl, $C_1$–$C_9$ linear or branched chain alkylphenyl, $C_1$–$C_9$ linear or branched chain dialkylphenyl, $C_1$–$C_9$ linear or branched chain alkoxyphenyl, hydroxyphenyl or benzyl; or with (B) an acyl anhydride having the structure $[R_8(C=O)]_2O$, wherein $R_8$ is $C_1$–$C_9$ linear or branched chain alkyl, to form an N-acylardeemin.

3. The process of claim 2, wherein $R_1$, $R_6$ and $R_7$ are hydrogen.

4. The process of claim 2, wherein $R_0$ is t-Bu, R and $R_5$ are $CH_3$, and X, Y and Z are Cl.

5. The process of claim 2, wherein $R_8$ is $CH_3$.

6. The process of claim 2, wherein $R_3$ is $CH_3$ and $R_4$ is hydrogen.

7. The process of claim 2, wherein $R_2$ is phenyl.

8. The process of claim 2, wherein R', R'' and R''' are n-Bu.

9. A compound having the structure:

[chemical structure]

wherein $R_0$ is hydrogen; wherein $R_4$ and $R_5$ are independently hydrogen or methyl; wherein $R_2$ is —$CR_3R_3$—CH=$CHR_4$; wherein $R_8$ is acetyl; and wherein $R_3$ is hydrogen or methyl; with the proviso that when $R_4$ is methyl, $R_8$ is acetyl and $R_5$ is hydrogen, then $R_3$ is hydrogen.

10. A composition comprising an amount of the compound of claim 9 effective to inhibit the growth of P-glycoprotein-mediated multidrug resistant cancer cells and a pharmaceutically acceptable carrier.

11. The composition of claim 10, further comprising a cytotoxic agent, wherein the cytotoxic agent is an anticancer agent.

12. The composition of claim 11, wherein the anticancer agent is adriamycin.

13. The composition of claim 11, wherein the anticancer agent is vinblastine.

14. The composition of claim 11, wherein the anticancer agent is paclitaxel.

15. The composition of claim 10, wherein the effective amount of the compound is between about 0.01 mg/kg to about 25 mg/kg of body weight.

16. The composition of claim 10, wherein the effective amount of the compound is between about 0.1 mg/kg to about 10 mg/kg of body weight.

17. A method of inhibiting the growth of P-glycoprotein-mediated multidrug resistant cancer cells comprising contacting the multidrug resistant cells with an amount of an ardeemin effective to inhibit the growth of multidrug resistant cells in combination with a pharmaceutically acceptable carrier wherein said cells are collaterally sensitive and wherein the ardeemin has the structure:

[chemical structure]

wherein $R_0$ is hydrogen; wherein $R_4$ and $R_5$ are independently hydrogen or methyl; wherein $R_2$ is —$CR_3R_3$—CH=$CHR_4$; wherein $R_8$ is acetyl; and wherein $R_3$ is hydrogen or methyl; with the proviso that when $R_4$ is methyl, $R_8$ is acetyl and $R_5$ is hydrogen, then $R_3$ is hydrogen.

18. The method of claim 17, further comprising administering an amount of a cytotoxic agent, wherein the cytotoxic agent is an anticancer agent.

19. The method of claim 18, wherein the anticancer agent is adriamycin.

20. The method of claim 18, wherein the anticancer agent is vinblastine.

21. The method of claim 18, wherein the anticancer agent is paclitaxel.

22. The method of claim 17, wherein the effective amount of the compound is between about 0.01 mg/kg to about 25 mg/kg of body weight.

23. The method of claim 17, wherein the effective amount of the compound is between about 0.1 mg/kg to about 10 mg/kg of body weight.

24. A compound having the structure:

[chemical structure]

wherein $R_0$ is hydrogen; wherein $R_4$ is hydrogen and $R_5$ methyl;

wherein $R_2$ is —$CR_3R_3$—CH=$CHR_4$; wherein $R_8$ is trifluoroacetyl; and wherein $R_3$ is methyl.

25. A composition comprising an amount of the compound of claim 24 effective to inhibit the growth of P-glycoprotein-mediated multidrug resistant cancer cells and a pharmaceutically acceptable carrier.

26. The composition of claim 25, further comprising a cytotoxic agent, wherein the cytotoxic agent is an anticancer agent.

27. The composition of claim 26, wherein the anticancer agent is adriamycin.

28. The composition of claim 26, wherein the anticancer agent is vinblastine.

29. The composition of claim 26, wherein the anticancer agent is paclitaxel.

30. The composition of claim 25, wherein the effective amount of the compound is between about 0.01 mg/kg to about 25 mg/kg of body weight.

31. The composition of claim 25, wherein the effective amount of the compound is between about 0.1 mg/kg to about 10 mg/kg of body weight.

32. A method of inhibiting the growth of P-glycoprotein-mediated multidrug resistant cancer cells comprising contacting the multidrug resistant cells with an amount of an ardeemin effective to inhibit the growth of multidrug resistant cells in combination with a pharmaceutically acceptable carrier wherein said cells are collaterally sensitive and wherein the ardeemin has the structure:

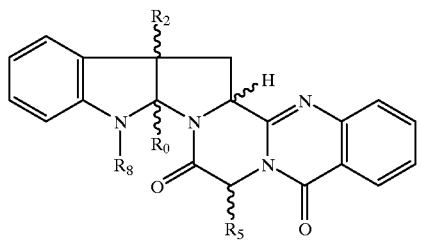

wherein $R_4$ is hydrogen and $R_5$ is methyl;

wherein $R_2$ is —$CR_3R_3$—CH=$CHR_4$; wherein $R_8$ is trifluoroacetyl; and wherein $R_3$ is methyl.

33. The method of claim 32, further comprising administering an amount of a cytotoxic agent, wherein the cytotoxic agent is an anticancer agent.

34. The method of claim 33, wherein the anticancer agent is adriamycin.

35. The method of claim 33, wherein the anticancer agent is vinblastine.

36. The method of claim 33, wherein the anticancer agent is paclitaxel.

37. The method of claim 32, wherein the effective amount of the compound is between about 0.01 mg/kg to about 25 mg/kg of body weight.

38. The method of claim 32, wherein the effective amount of the compound is between about 0.1 mg/kg to about 10 mg/kg of body weight.

* * * * *